United States Patent
Wacker et al.

(10) Patent No.: US 12,398,380 B2
(45) Date of Patent: *Aug. 26, 2025

(54) METHODS OF HOST CELL MODIFICATION

(71) Applicant: GLAXOSMITHKLINE BIOLOGICALS S.A., Rixensart (BE)

(72) Inventors: Michael Wacker, Unterengstringen (CH); Michael Kowarik, Zurich (CH); Fabiana Fernandez, Unterengstringen (CH)

(73) Assignee: GlaxoSmithKline Biologicals SA, Rixensart (BE)

( * ) Notice: Subject to any disclaimer, the term of this patent is extended or adjusted under 35 U.S.C. 154(b) by 109 days.

This patent is subject to a terminal disclaimer.

(21) Appl. No.: 17/541,454

(22) Filed: Dec. 3, 2021

(65) Prior Publication Data

US 2022/0186196 A1 Jun. 16, 2022

Related U.S. Application Data

(63) Continuation of application No. 15/028,483, filed as application No. PCT/EP2014/071889 on Oct. 13, 2014, now Pat. No. 11,220,676.

(60) Provisional application No. 61/889,672, filed on Oct. 11, 2013.

(51) Int. Cl.
| | |
|---|---|
| C12N 5/00 | (2006.01) |
| A61K 39/104 | (2006.01) |
| A61K 39/108 | (2006.01) |
| A61K 39/112 | (2006.01) |
| C12N 9/10 | (2006.01) |
| C12N 15/70 | (2006.01) |
| C12N 15/90 | (2006.01) |
| C12P 21/00 | (2006.01) |
| A61K 39/00 | (2006.01) |

(52) U.S. Cl.
CPC ........ *C12N 9/1051* (2013.01); *A61K 39/0258* (2013.01); *A61K 39/0283* (2013.01); *A61K 39/104* (2013.01); *C12N 15/70* (2013.01); *C12N 15/902* (2013.01); *C12P 21/00* (2013.01); *A61K 2039/6037* (2013.01); *C12N 2795/00041* (2013.01); *C12N 2800/30* (2013.01); *Y02A 50/30* (2018.01)

(58) Field of Classification Search
CPC .... C12N 9/1051; C12N 15/70; C12N 15/902; C12N 2795/00041; C12N 2800/30; A61K 39/0258; A61K 39/0283; A61K 39/104; A61K 2039/6037; C12P 21/00; Y02A 50/30

See application file for complete search history.

(56) References Cited

U.S. PATENT DOCUMENTS

2017/0121691 A1 5/2017 Wacker et al.

FOREIGN PATENT DOCUMENTS

| EP | 3055416 B1 | 1/2020 | |
|---|---|---|---|
| WO | 2006119987 A2 | 11/2006 | |
| WO | 2009104074 A2 | 8/2009 | |
| WO | 2011027116 A1 | 3/2011 | |
| WO | WO-2011062615 A1 * | 5/2011 | ......... A61K 39/0258 |
| WO | 2011138361 A1 | 11/2011 | |
| WO | 2013034664 A1 | 3/2013 | |
| WO | 2013062939 A2 | 5/2013 | |
| WO | 2014037585 A1 | 3/2014 | |
| WO | 2014057109 A1 | 4/2014 | |
| WO | 2014072405 A1 | 5/2014 | |
| WO | 2015052344 A1 | 4/2015 | |

OTHER PUBLICATIONS

The Wood Dissertation (University of Manchester, 2012). (Year: 2012).*
Bastin & Reeves in "Sequence and analysis of the O antigen (rfb) cluster of *Escherichia coli* ) O111" (Gene 1995 vol. 164 pp. 17-23). (Year: 1995).*
Guarino_Dissertion_Cornell_Univ_Jan_2013 (Year: 2013).*
Waegeman_et_al_2011 (Year: 2011).*
Bastin & Reeves in "Sequence and analysis of the O antigen (rib) cluster of *Escherichia coli* O111" (Gene 1995 vol. 164 pp. 17-23). (Year: 1995).
Miyazaki et al., Appl. Environ. Microbial., 79 (14): 4440-4447, (Year: 2013).
Martinez-Morales, J. Bacteriol., 181 (22): 7143-7148, 1999.
Feldman, et al., "Engineering N-linked protein glycosylation with diverse 0 antigen lipopolysaccharide stuctures in *Escherichia coli*", Proceedings of the National Academy of Sciences, National Academy of Sciences, US; Feb. 22, 2005; vol. 102 {8); pp. 3016-3021.
Kuhlman, et al., "Site-specific chromosal integration of large synthetic constructs", Nucleic Acids Research, Apr. 1, 2010; vol. 38 {6); pp. E92-E91.
Lee, et al., "Gene doctoring: a method for recombineering in Laboratory and pathogenic *Escherichia coli* strains" BMC Microbiology; Dec. 9, 2009; vol. 9 (1 ); pp. 252.
Ihssen, et al., "Production of glycoprotein vaccines in *Escherichia coli*" Microbial Cell Factories; Aug. 11, 2010; vol. 9 (1); pp. 61.
Wacker, et al., "Prevention of *Staphylococcus aureus* Infections by Glycoprotein Vaccines Synthesized in *Escherichia coli*." Journal of Infectious Diseases; May 15, 2014; vol. 209 (10); pp. 1551-1561.

* cited by examiner

*Primary Examiner* — Catherine S Hibbert

(57) ABSTRACT

Described herein are methods of inserting nucleic acid sequences into host cells. Also described herein are genetically stable host cells comprising inserted nucleic acid sequences and methods of using such host cells in the generation of proteins.

5 Claims, 37 Drawing Sheets

Specification includes a Sequence Listing.

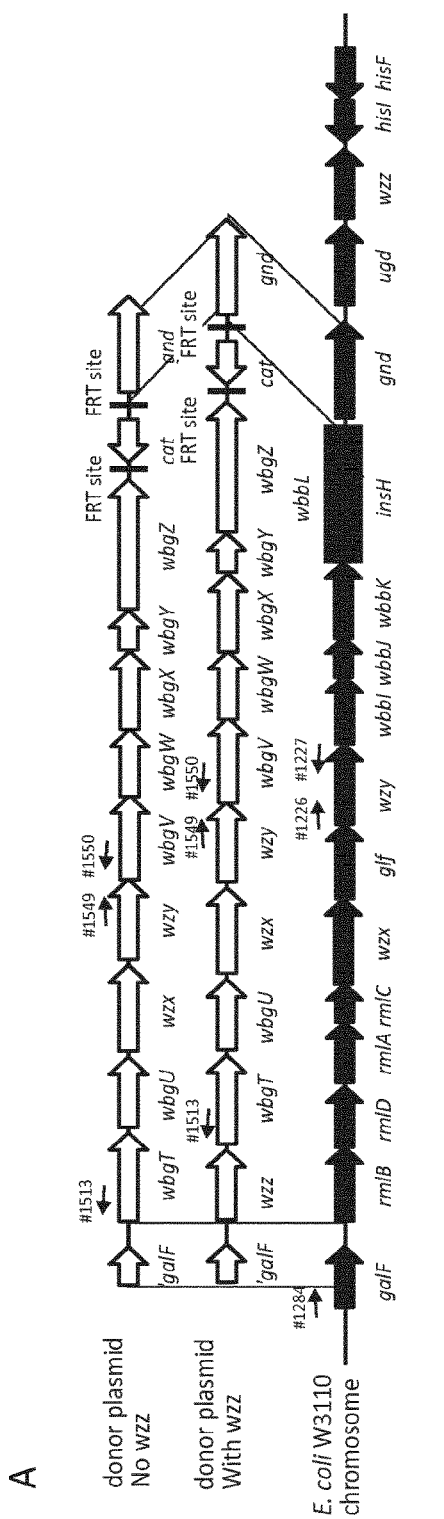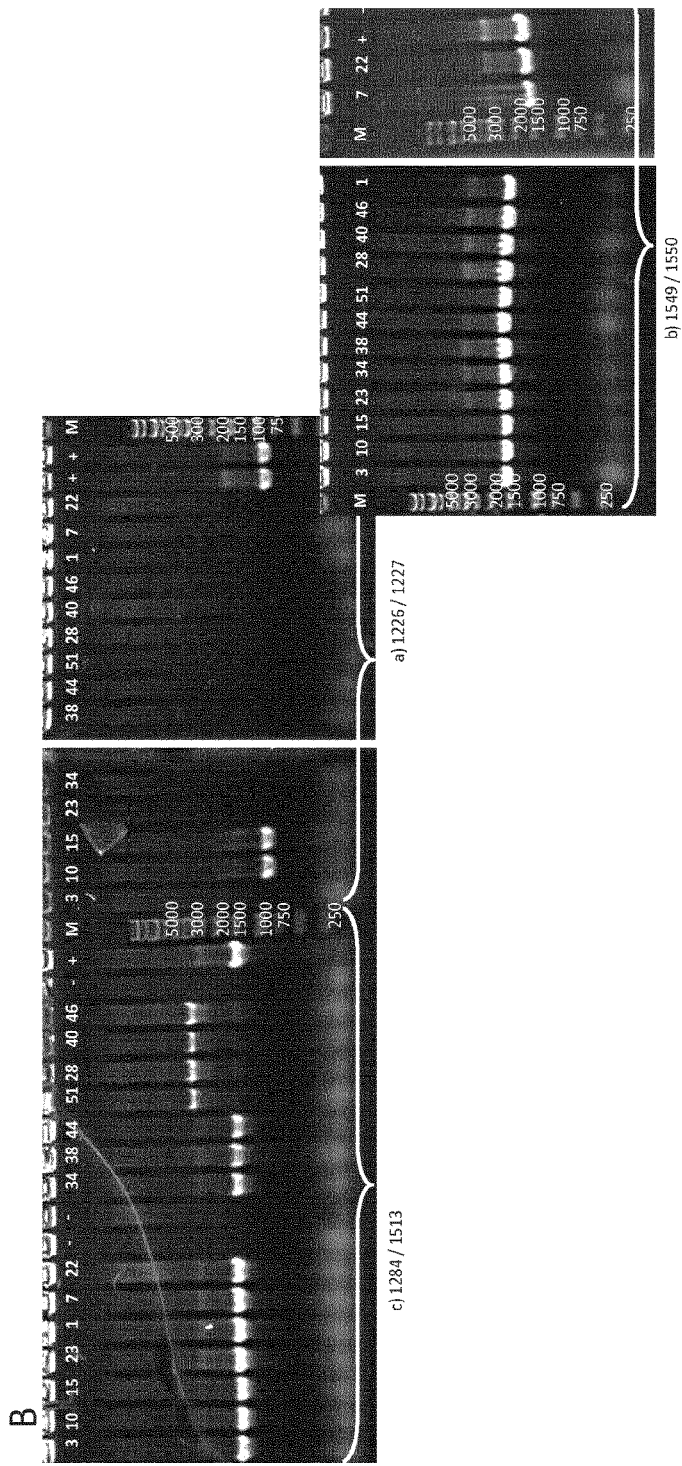
FIG. 15

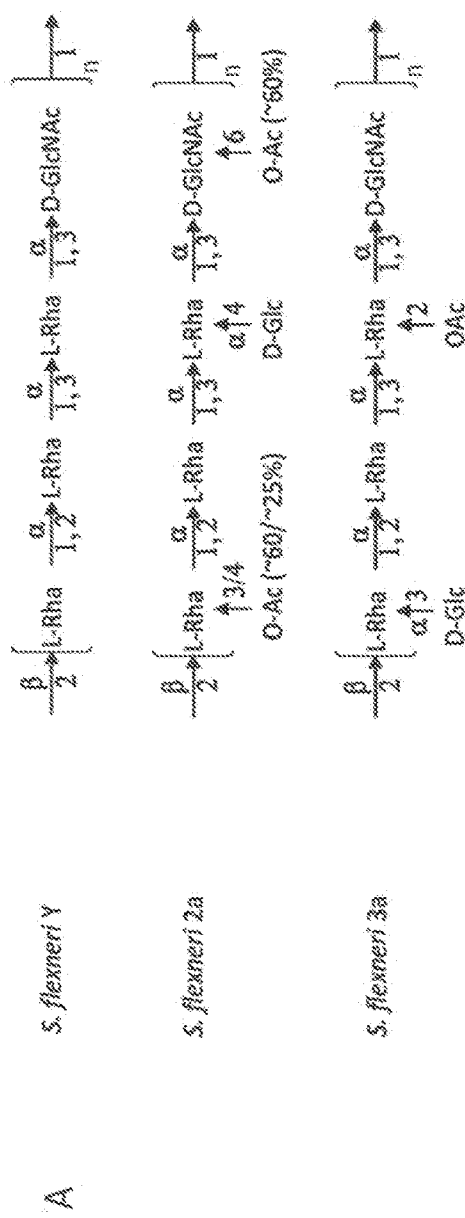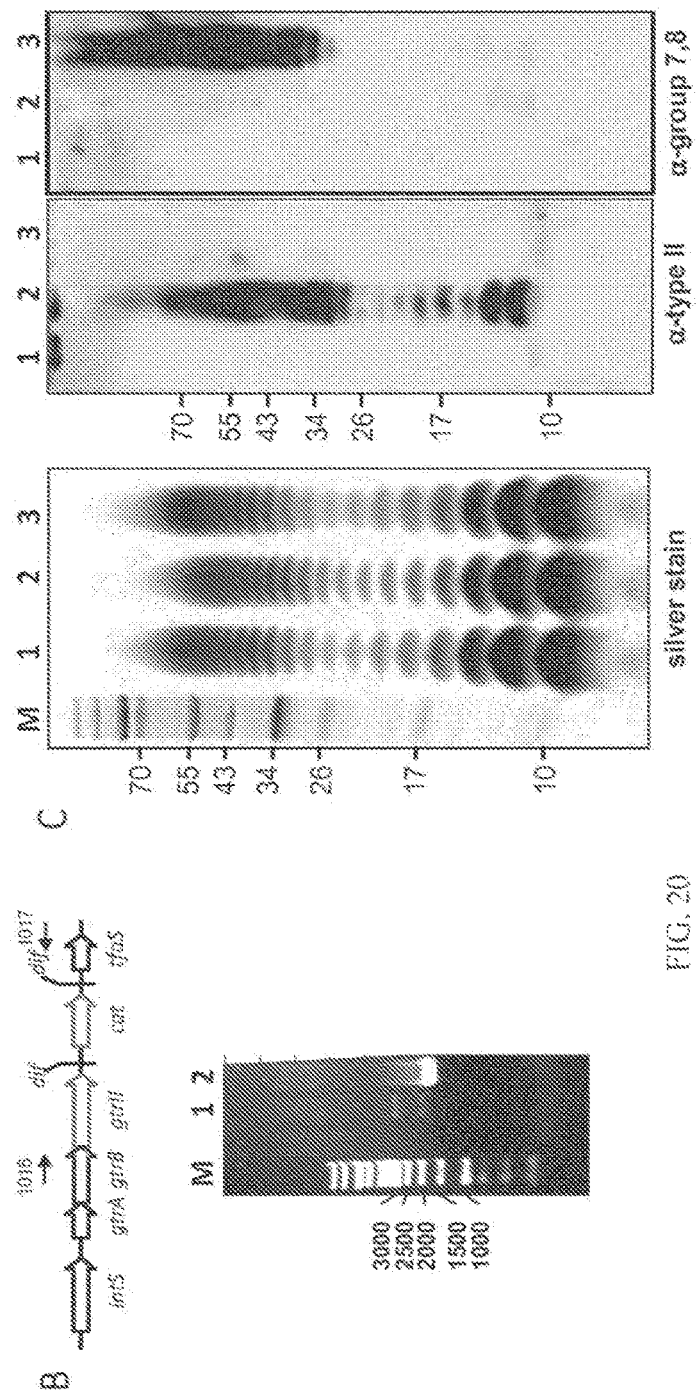
FIG. 20

SEQUENCE LISTING

```
<160> NUMBER OF SEQ ID NOS: 72

<210> SEQ ID NO 1
<211> LENGTH: 9
<212> TYPE: PRT
<213> ORGANISM: Artificial Sequence
<220> FEATURE:
<223> OTHER INFORMATION: structural group found in homing endonuclease

<400> SEQUENCE: 1

Leu Ala Gly Leu Ile Asp Ala Asp Gly
1               5
```

```
<210> SEQ ID NO 2
<211> LENGTH: 6
<212> TYPE: PRT
<213> ORGANISM: Artificial Sequence
<220> FEATURE:
<223> OTHER INFORMATION: structural group found in homing endonuclease

<400> SEQUENCE: 2

Gly Ile Tyr Tyr Ile Gly
1               5

<210> SEQ ID NO 3
<211> LENGTH: 18
<212> TYPE: DNA
<213> ORGANISM: Artificial Sequence
<220> FEATURE:
<223> OTHER INFORMATION: sequence recognized by SceI

<400> SEQUENCE: 3
tagggataac agggtaat                                                        18

<210> SEQ ID NO 4
<211> LENGTH: 24
<212> TYPE: DNA
<213> ORGANISM: Aspergillus nidulans
<220> FEATURE:
<223> OTHER INFORMATION: recognition site of homing endonuclease AniI

<400> SEQUENCE: 4
ttgaggaggt ttctctgtaa ataa                                                 24

<210> SEQ ID NO 5
<211> LENGTH: 24
<212> TYPE: DNA
<213> ORGANISM: Aspergillus nidulans
<220> FEATURE:
<223> OTHER INFORMATION: recognition site of homing endonuclease AniI

<400> SEQUENCE: 5
ttatttacag agaaacctcc tcaa                                                 24

<210> SEQ ID NO 6
<211> LENGTH: 26
<212> TYPE: DNA
<213> ORGANISM: Chlamydomonas eugametos
<220> FEATURE:
<223> OTHER INFORMATION: recognition site of homing endonuclease CeuI

<400> SEQUENCE: 6
taactataac ggtcctaagg tagcga                                               26

<210> SEQ ID NO 7
<211> LENGTH: 26
<212> TYPE: DNA
<213> ORGANISM: Chlamydomonas eugametos
<220> FEATURE:
<223> OTHER INFORMATION: recognition site of homing endonuclease CeuI

<400> SEQUENCE: 7
tcgctacctt aggaccgtta tagtta                                               26

<210> SEQ ID NO 8
<211> LENGTH: 30
<212> TYPE: DNA
<213> ORGANISM: Chlamydomonas humicola
```

```
<220> FEATURE:
<223> OTHER INFORMATION: 5-prime recognition site of homing endonuclease
      ChuI

<400> SEQUENCE: 8
gaaggtttgg cacctcgatg tcggctcatc                                              30

<210> SEQ ID NO 9
<211> LENGTH: 30
<212> TYPE: DNA
<213> ORGANISM: Chlamydomonas humicola
<220> FEATURE:
<223> OTHER INFORMATION: 5-prime recognition site of homing endonuclease
      ChuI

<400> SEQUENCE: 9
gatgagccga catcgaggtg ccaaaccttc                                              30

<210> SEQ ID NO 10
<211> LENGTH: 23
<212> TYPE: DNA
<213> ORGANISM: Chlamydomonas pallidostigmata
<220> FEATURE:
<223> OTHER INFORMATION: recognition site of homing endonuclease CpaI

<400> SEQUENCE: 10
cgatcctaag gtagcgaaat tca                                                     23

<210> SEQ ID NO 11
<211> LENGTH: 23
<212> TYPE: DNA
<213> ORGANISM: Chlamydomonas pallidostigmata
<220> FEATURE:
<223> OTHER INFORMATION: recognition site of homing endonuclease CpaI

<400> SEQUENCE: 11
tgaatttcgc taccttagga tcg                                                     23

<210> SEQ ID NO 12
<211> LENGTH: 20
<212> TYPE: DNA
<213> ORGANISM: Chlamydomonas pallidostigmata
<220> FEATURE:
<223> OTHER INFORMATION: recognition site of homing endonuclease CpaII

<400> SEQUENCE: 12
cccggctaac tctgtgccag                                                         20

<210> SEQ ID NO 13
<211> LENGTH: 20
<212> TYPE: DNA
<213> ORGANISM: Chlamydomonas pallidostigmata
<220> FEATURE:
<223> OTHER INFORMATION: recognition site of homing endonuclease CpaII

<400> SEQUENCE: 13
ctggcacaga gttagccggg                                                         20

<210> SEQ ID NO 14
<211> LENGTH: 30
<212> TYPE: DNA
<213> ORGANISM: Chlamydomonas reinhardtii
<220> FEATURE:
<223> OTHER INFORMATION: recognition site of homing endonuclease CreI

<400> SEQUENCE: 14
```

```
ctgggttcaa aacgtcgtga gacagtttgg                                          30

<210> SEQ ID NO 15
<211> LENGTH: 30
<212> TYPE: DNA
<213> ORGANISM: Chlamydomonas reinhardtii
<220> FEATURE:
<223> OTHER INFORMATION: recognition site of homing endonuclease CreI

<400> SEQUENCE: 15
ccaaactgtc tcacgacgtt ttgaacccag                                          30

<210> SEQ ID NO 16
<211> LENGTH: 30
<212> TYPE: DNA
<213> ORGANISM: Desulfurococcus mobilis
<220> FEATURE:
<223> OTHER INFORMATION: recognition site of homing endonuclease DmoI

<400> SEQUENCE: 16
atgccttgcc gggtaagttc cggcgcgcat                                          30

<210> SEQ ID NO 17
<211> LENGTH: 30
<212> TYPE: DNA
<213> ORGANISM: Desulfurococcus mobilis
<220> FEATURE:
<223> OTHER INFORMATION: recognition site of homing endonuclease DmoI

<400> SEQUENCE: 17
atgcgcgccg gaacttaccc ggcaaggcat                                          30

<210> SEQ ID NO 18
<211> LENGTH: 24
<212> TYPE: DNA
<213> ORGANISM: Escherichia coli pI-DreI
<220> FEATURE:
<223> OTHER INFORMATION: recognition site of homing endonuclease DreI

<400> SEQUENCE: 18
caaaacgtcg taagttccgg cgcg                                                24

<210> SEQ ID NO 19
<211> LENGTH: 24
<212> TYPE: DNA
<213> ORGANISM: Escherichia coli pI-DreI
<220> FEATURE:
<223> OTHER INFORMATION: recognition site of homing endonuclease DreI

<400> SEQUENCE: 19
cgcgccggaa cttacgacgt tttg                                                24

<210> SEQ ID NO 20
<211> LENGTH: 24
<212> TYPE: DNA
<213> ORGANISM: Bacillus subtilis phage SPO1
<220> FEATURE:
<223> OTHER INFORMATION: recognition site of homing endonuclease HmuI

<400> SEQUENCE: 20
agtaatgagc ctaacgctca gcaa                                                24

<210> SEQ ID NO 21
<211> LENGTH: 24
<212> TYPE: DNA
<213> ORGANISM: Bacillus subtilis phage SPO1
```

```
<220> FEATURE:
<223> OTHER INFORMATION: recognition site of homing endonuclease HmuI

<400> SEQUENCE: 21
ttgctgagcg ttaggctcat tact                                              24

<210> SEQ ID NO 22
<211> LENGTH: 24
<212> TYPE: DNA
<213> ORGANISM: Bacillus subtilis phage SP82
<220> FEATURE:
<223> OTHER INFORMATION: recognition site of homing endonuclease HmuII

<400> SEQUENCE: 22
agtaatgagc ctaacgctca acaa                                              24

<210> SEQ ID NO 23
<211> LENGTH: 24
<212> TYPE: DNA
<213> ORGANISM: Bacillus subtilis phage SP82
<220> FEATURE:
<223> OTHER INFORMATION: recognition site of homing endonuclease HmuII

<400> SEQUENCE: 23
ttgttgagcg ttaggctcat tact                                              24

<210> SEQ ID NO 24
<211> LENGTH: 24
<212> TYPE: DNA
<213> ORGANISM: Lactococcus lactis
<220> FEATURE:
<223> OTHER INFORMATION: recognition site of homing endonuclease LlaI

<400> SEQUENCE: 24
cacatccata accatatcat tttt                                              24

<210> SEQ ID NO 25
<211> LENGTH: 24
<212> TYPE: DNA
<213> ORGANISM: Lactococcus lactis
<220> FEATURE:
<223> OTHER INFORMATION: recognition site of homing endonuclease LlaI

<400> SEQUENCE: 25
aaaaatgata tggttatgga tgtg                                              24

<210> SEQ ID NO 26
<211> LENGTH: 30
<212> TYPE: DNA
<213> ORGANISM: Monomastix sp.
<220> FEATURE:
<223> OTHER INFORMATION: recognition site of homing endonuclease MsoI

<400> SEQUENCE: 26
ctgggttcaa aacgtcgtga gacagtttgg                                        30

<210> SEQ ID NO 27
<211> LENGTH: 30
<212> TYPE: DNA
<213> ORGANISM: Monomastix sp.
<220> FEATURE:
<223> OTHER INFORMATION: recognition site of homing endonuclease MsoI

<400> SEQUENCE: 27
ccaaactgtc tcacgacgtt ttgaacccag                                        30
```

<210> SEQ ID NO 28
<211> LENGTH: 30
<212> TYPE: DNA
<213> ORGANISM: Pyrococcus furiosus Vc1
<220> FEATURE:
<223> OTHER INFORMATION: recognition site of homing endonuclease PI-PfuI

<400> SEQUENCE: 28
gaagatggga ggagggaccg gactcaactt                          30

<210> SEQ ID NO 29
<211> LENGTH: 30
<212> TYPE: DNA
<213> ORGANISM: Pyrococcus furiosus Vc1
<220> FEATURE:
<223> OTHER INFORMATION: recognition site of homing endonuclease PI-PfuI

<400> SEQUENCE: 29
aagttgagtc cggtccctcc tcccatcttc                          30

<210> SEQ ID NO 30
<211> LENGTH: 15
<212> TYPE: DNA
<213> ORGANISM: Pyrococcus kodakaraensis KOD1
<220> FEATURE:
<223> OTHER INFORMATION: recognition site of homing endonuclease
      PI-PkoII

<400> SEQUENCE: 30
cagtactacg gttac                                          15

<210> SEQ ID NO 31
<211> LENGTH: 15
<212> TYPE: DNA
<213> ORGANISM: Pyrococcus kodakaraensis KOD1
<220> FEATURE:
<223> OTHER INFORMATION: recognition site of homing endonuclease
      PI-PkoII

<400> SEQUENCE: 31
gtaaccgtag tactg                                          15

<210> SEQ ID NO 32
<211> LENGTH: 25
<212> TYPE: DNA
<213> ORGANISM: Pyrobaculum organotrophum
<220> FEATURE:
<223> OTHER INFORMATION: recognition site of homing endonuclease PorI

<400> SEQUENCE: 32
gcgagcccgt aagggtgtgt acggg                               25

<210> SEQ ID NO 33
<211> LENGTH: 25
<212> TYPE: DNA
<213> ORGANISM: Pyrobaculum organotrophum
<220> FEATURE:
<223> OTHER INFORMATION: recognition site of homing endonuclease PorI

<400> SEQUENCE: 33
cccgtacaca cccttacggg ctcgc                               25

<210> SEQ ID NO 34
<211> LENGTH: 29
<212> TYPE: DNA
<213> ORGANISM: Physarum polycephalum

```
<220> FEATURE:
<223> OTHER INFORMATION: recognition site of homing endonuclease PpoI

<400> SEQUENCE: 34
taactatgac tctcttaagg tagccaaat                                    29

<210> SEQ ID NO 35
<211> LENGTH: 29
<212> TYPE: DNA
<213> ORGANISM: Physarum polycephalum
<220> FEATURE:
<223> OTHER INFORMATION: recognition site of homing endonuclease PpoI

<400> SEQUENCE: 35
atttggctac cttaagagag tcatagtta                                    29

<210> SEQ ID NO 36
<211> LENGTH: 30
<212> TYPE: DNA
<213> ORGANISM: Pyrococcus sp.
<220> FEATURE:
<223> OTHER INFORMATION: recognition site of homing endonuclease PI-PspI

<400> SEQUENCE: 36
tggcaaacag ctattatggg tattatgggt                                   30

<210> SEQ ID NO 37
<211> LENGTH: 30
<212> TYPE: DNA
<213> ORGANISM: Pyrococcus sp.
<220> FEATURE:
<223> OTHER INFORMATION: recognition site of homing endonuclease PI-PspI

<400> SEQUENCE: 37
acccataata cccataatag ctgtttgcca                                   30

<210> SEQ ID NO 38
<211> LENGTH: 28
<212> TYPE: DNA
<213> ORGANISM: Saccharomyces capensis
<220> FEATURE:
<223> OTHER INFORMATION: recognition site of homing endonuclease ScaI

<400> SEQUENCE: 38
tgtcacattg aggtgcacta gttattac                                     28

<210> SEQ ID NO 39
<211> LENGTH: 28
<212> TYPE: DNA
<213> ORGANISM: Saccharomyces capensis
<220> FEATURE:
<223> OTHER INFORMATION: recognition site of homing endonuclease ScaI

<400> SEQUENCE: 39
gtaataacta gtgcacctca atgtgaca                                     28

<210> SEQ ID NO 40
<211> LENGTH: 30
<212> TYPE: DNA
<213> ORGANISM: Saccharomyces cerevisiae
<220> FEATURE:
<223> OTHER INFORMATION: recognition site of homing endonuclease SceI

<400> SEQUENCE: 40
agttacgcta gggataacag ggtaatatag                                   30
```

```
<210> SEQ ID NO 41
<211> LENGTH: 30
<212> TYPE: DNA
<213> ORGANISM: Saccharomyces cerevisiae
<220> FEATURE:
<223> OTHER INFORMATION: recognition site of homing endonuclease SceI

<400> SEQUENCE: 41
ctatattacc ctgttatccc tagcgtaact                                    30

<210> SEQ ID NO 42
<211> LENGTH: 39
<212> TYPE: DNA
<213> ORGANISM: Saccharomyces cerevisiae
<220> FEATURE:
<223> OTHER INFORMATION: recognition site of homing endonuclease PI-SceI

<400> SEQUENCE: 42
atctatgtcg ggtgcggaga aagaggtaat gaaatggca                           39

<210> SEQ ID NO 43
<211> LENGTH: 39
<212> TYPE: DNA
<213> ORGANISM: Saccharomyces cerevisiae
<220> FEATURE:
<223> OTHER INFORMATION: recognition site of homing endonuclease PI-SceI

<400> SEQUENCE: 43
tgccatttca ttacctcttt ctccgcaccc gacatagat                           39

<210> SEQ ID NO 44
<211> LENGTH: 29
<212> TYPE: DNA
<213> ORGANISM: Saccharomyces cerevisiae
<220> FEATURE:
<223> OTHER INFORMATION: recognition site of homing endonuclease SceII

<400> SEQUENCE: 44
ttttgattct ttggtcaccc tgaagtata                                     29

<210> SEQ ID NO 45
<211> LENGTH: 29
<212> TYPE: DNA
<213> ORGANISM: Saccharomyces cerevisiae
<220> FEATURE:
<223> OTHER INFORMATION: recognition site of homing endonuclease SceII

<400> SEQUENCE: 45
tatacttcag ggtgaccaaa gaatcaaaa                                     29

<210> SEQ ID NO 46
<211> LENGTH: 29
<212> TYPE: DNA
<213> ORGANISM: Saccharomyces cerevisiae
<220> FEATURE:
<223> OTHER INFORMATION: recognition site of homing endonuclease SceIII

<400> SEQUENCE: 46
attggaggtt ttggtaacta tttattacc                                     29

<210> SEQ ID NO 47
<211> LENGTH: 29
<212> TYPE: DNA
<213> ORGANISM: Saccharomyces cerevisiae
<220> FEATURE:
<223> OTHER INFORMATION: recognition site of homing endonuclease SceIII
```

-continued

<400> SEQUENCE: 47
ggtaataaat agttaccaaa acctccaat                                29

<210> SEQ ID NO 48
<211> LENGTH: 29
<212> TYPE: DNA
<213> ORGANISM: Saccharomyces cerevisiae
<220> FEATURE:
<223> OTHER INFORMATION: recognition site of homing endonuclease SceIV

<400> SEQUENCE: 48
tcttttctct tgattagccc taatctacg                                29

<210> SEQ ID NO 49
<211> LENGTH: 29
<212> TYPE: DNA
<213> ORGANISM: Saccharomyces cerevisiae
<220> FEATURE:
<223> OTHER INFORMATION: recognition site of homing endonuclease SceIV

<400> SEQUENCE: 49
cgtagattag ggctaatcaa gagaaaaga                                29

<210> SEQ ID NO 50
<211> LENGTH: 24
<212> TYPE: DNA
<213> ORGANISM: Saccharomyces cerevisiae
<220> FEATURE:
<223> OTHER INFORMATION: recognition site of homing endonuclease SceV

<400> SEQUENCE: 50
aataattttc ttcttagtaa tgcc                                     24

<210> SEQ ID NO 51
<211> LENGTH: 24
<212> TYPE: DNA
<213> ORGANISM: Saccharomyces cerevisiae
<220> FEATURE:
<223> OTHER INFORMATION: recognition site of homing endonuclease SceV

<400> SEQUENCE: 51
ggcattacta agaagaaaat tatt                                     24

<210> SEQ ID NO 52
<211> LENGTH: 24
<212> TYPE: DNA
<213> ORGANISM: Saccharomyces cerevisiae
<220> FEATURE:
<223> OTHER INFORMATION: recognition site of homing endonuclease SceVI

<400> SEQUENCE: 52
gttatttaat gttttagtag ttgg                                     24

<210> SEQ ID NO 53
<211> LENGTH: 24
<212> TYPE: DNA
<213> ORGANISM: Saccharomyces cerevisiae
<220> FEATURE:
<223> OTHER INFORMATION: recognition site of homing endonuclease SceVI

<400> SEQUENCE: 53
ccaactacta aaacattaaa taac                                     24

<210> SEQ ID NO 54

```
<211> LENGTH: 28
<212> TYPE: DNA
<213> ORGANISM: Saccharomyces cerevisiae
<220> FEATURE:
<223> OTHER INFORMATION: recognition site of homing endonuclease SceVII

<400> SEQUENCE: 54
tgtcacattg aggtgcacta gttattac                                           28

<210> SEQ ID NO 55
<211> LENGTH: 28
<212> TYPE: DNA
<213> ORGANISM: Saccharomyces cerevisiae
<220> FEATURE:
<223> OTHER INFORMATION: recognition site of homing endonuclease SceVII

<400> SEQUENCE: 55
gtaataacta gtgcacctca atgtgaca                                           28

<210> SEQ ID NO 56
<211> LENGTH: 19
<212> TYPE: DNA
<213> ORGANISM: Synechocystis sp. PCC 6803
<220> FEATURE:
<223> OTHER INFORMATION: recognition site of homing endonuclease
     Ssp6803I

<400> SEQUENCE: 56
gtcgggctca tacccgaa                                                      19

<210> SEQ ID NO 57
<211> LENGTH: 19
<212> TYPE: DNA
<213> ORGANISM: Synechocystis sp. PCC 6803
<220> FEATURE:
<223> OTHER INFORMATION: recognition site of homing endonuclease
     Ssp6803I

<400> SEQUENCE: 57
ttcgggttat gagcccgac                                                     19

<210> SEQ ID NO 58
<211> LENGTH: 24
<212> TYPE: DNA
<213> ORGANISM: Escherichia coli phage T4
<220> FEATURE:
<223> OTHER INFORMATION: recognition site of homing endonuclease TevI

<400> SEQUENCE: 58
agtggtatca acgctcagta gatg                                               24

<210> SEQ ID NO 59
<211> LENGTH: 24
<212> TYPE: DNA
<213> ORGANISM: Escherichia coli phage T4
<220> FEATURE:
<223> OTHER INFORMATION: recognition site of homing endonuclease TevI

<400> SEQUENCE: 59
catctactga gcgttgatac cact                                               24

<210> SEQ ID NO 60
<211> LENGTH: 30
<212> TYPE: DNA
<213> ORGANISM: Escherichia coli phage T4
<220> FEATURE:
<223> OTHER INFORMATION: recognition site of homing endonuclease TevII
```

<210> SEQ ID NO 61
<211> LENGTH: 30
<212> TYPE: DNA
<213> ORGANISM: Escherichia coli phage T4
<220> FEATURE:
<223> OTHER INFORMATION: recognition site of homing endonuclease TevII

<400> SEQUENCE: 61
gaataacgtg ttcacttcat actcataagc     30

<210> SEQ ID NO 62
<211> LENGTH: 30
<212> TYPE: DNA
<213> ORGANISM: Escherichia coli phage RB3
<220> FEATURE:
<223> OTHER INFORMATION: recognition site of homing endonuclease TevIII

<400> SEQUENCE: 62
tatgtatctt ttgcgtgtac ctttaacttc     30

<210> SEQ ID NO 63
<211> LENGTH: 30
<212> TYPE: DNA
<213> ORGANISM: Escherichia coli phage RB3
<220> FEATURE:
<223> OTHER INFORMATION: recognition site of homing endonuclease TevIII

<400> SEQUENCE: 63
gaagttaaag gtacacgcaa aagatacata     30

<210> SEQ ID NO 64
<211> LENGTH: 22
<212> TYPE: DNA
<213> ORGANISM: Artificial Sequence
<220> FEATURE:
<223> OTHER INFORMATION: recognition site of homing endonuclease PI-TliI
<220> FEATURE:
<221> NAME/KEY: misc_feature
<222> LOCATION: 6, 12
<223> OTHER INFORMATION: n = A,T,C or G

<400> SEQUENCE: 64
taygcngaya cngacggytt yt     22

<210> SEQ ID NO 65
<211> LENGTH: 22
<212> TYPE: DNA
<213> ORGANISM: Thermococcus litoralis
<220> FEATURE:
<223> OTHER INFORMATION: recognition site of homing endonuclease PI-TliI
<220> FEATURE:
<221> NAME/KEY: misc_feature
<222> LOCATION: 11, 17
<223> OTHER INFORMATION: n = A,T,C or G

<400> SEQUENCE: 65
araatccgtc ngtrtcngcr ta     22

<210> SEQ ID NO 66
<211> LENGTH: 30
<212> TYPE: DNA
<213> ORGANISM: Thermococcus litoralis
<220> FEATURE:

```
<223> OTHER INFORMATION: recognition site of homing endonuclease
      PI-TliII

<400> SEQUENCE: 66
aaattgcttg caaacagcta ttacggctat                                    30

<210> SEQ ID NO 67
<211> LENGTH: 30
<212> TYPE: DNA
<213> ORGANISM: Thermococcus litoralis
<220> FEATURE:
<223> OTHER INFORMATION: recognition site of homing endonuclease
      PI-TliII

<400> SEQUENCE: 67
atagccgtaa tagctgtttg caagcaattt                                    30

<210> SEQ ID NO 68
<211> LENGTH: 19
<212> TYPE: DNA
<213> ORGANISM: Thermoproteus sp. IC-061
<220> FEATURE:
<223> OTHER INFORMATION: recognition site of homing endonuclease Tsp061I

<400> SEQUENCE: 68
cttcagtatg ccccgaaac                                                19

<210> SEQ ID NO 69
<211> LENGTH: 19
<212> TYPE: DNA
<213> ORGANISM: Thermoproteus sp. IC-061
<220> FEATURE:
<223> OTHER INFORMATION: recognition site of homing endonuclease Tsp061I

<400> SEQUENCE: 69
gtttcggggc atactgaag                                                19

<210> SEQ ID NO 70
<211> LENGTH: 24
<212> TYPE: DNA
<213> ORGANISM: Vulcanisaeta distributa IC-141
<220> FEATURE:
<223> OTHER INFORMATION: recognition site of homing endonuclease Vdi141I

<400> SEQUENCE: 70
cctgactctc ttaaggtagc caaa                                          24

<210> SEQ ID NO 71
<211> LENGTH: 24
<212> TYPE: DNA
<213> ORGANISM: Vulcanisaeta distributa IC-141
<220> FEATURE:
<223> OTHER INFORMATION: recognition site of homing endonuclease Vdi141I

<400> SEQUENCE: 71
tttggctacc ttaagagagt cagg                                          24

<210> SEQ ID NO 72
<211> LENGTH: 5
<212> TYPE: PRT
<213> ORGANISM: Artificial Sequence
<220> FEATURE:
<223> OTHER INFORMATION: synthetic - N-Glycosylation Consensus Sequence
<220> FEATURE:
<221> NAME/KEY: MISC_FEATURE
<222> LOCATION: (1)..(1)
<223> OTHER INFORMATION: Xaa = Asp or Glu
```

```
<220> FEATURE:
<221> NAME/KEY: MISC_FEATURE
<222> LOCATION: (2)..(2)
<223> OTHER INFORMATION: Xaa = any natural amino acid except Pro
<220> FEATURE:
<221> NAME/KEY: MISC_FEATURE
<222> LOCATION: (4)..(4)
<223> OTHER INFORMATION: Xaa = any natural amino acid except Pro
<220> FEATURE:
<221> NAME/KEY: MISC_FEATURE
<222> LOCATION: (5)..(5)
<223> OTHER INFORMATION: Xaa = Ser or Thr

<400> SEQUENCE: 72

Xaa Xaa Asn Xaa Xaa
1               5
```

METHODS OF HOST CELL MODIFICATION

The instant application contains a Sequence Listing which has been submitted electronically in ASCII format and is hereby incorporated by reference in its entirety. Said ASCII copy is named LB65502_US_SEQLST.txt and is 47.8 kilobytes in size.

1 INTRODUCTION

Described herein are methods of inserting nucleic acid sequences into host cells. Also described herein are genetically stable host cells comprising inserted nucleic acid sequences and methods of using such host cells in the generation of proteins, and the use of such host cells for the glycosylation of proteins.

2 BACKGROUND

Recombinant expression of single genes or small DNA fragments is most often performed by providing the recombinant gene on a plasmid. Plasmids can be efficiently produced and manipulated by molecular biology techniques [1]. They are quickly inserted in a host cell and maintained by antibiotic selection conferred to the plasmid bearing host cell by a resistance cassette which is also encoded on the circular plasmid molecule. Typically, recombinant proteins are expressed using plasmids that contain the genes encoding the proteins.

The recombinant expression of large DNA fragments has various limitations. For example standard expression plasmids are often genetically unstable following insertion of large DNA fragments. Often, cosmids and/or fosmids are used, which contain elements that stabilize the inserted DNA by several mechanisms, in attempts to overcome plasmid instability. Further, copy numbers of plasmids range over different orders of magnitude, depending on the origin of replication, and they can be additionally influenced by growth state [2], medium composition, and individual cell to cell differences [3]. In addition, there is only a limited number of cosmids and fosmids available. Thus, it is generally difficult to combine multiple large DNA fragments in a single cell.

An additional drawback of plasmids in general, may they be large or small, is the need for selection pressure to maintain the episomal elements in the cell. The selection pressure requires the use of antibiotics, which is undesirable for the production of medicinal products due to the danger of allergic reactions against antibiotics and the additional costs for manufacturing. Furthermore, selection pressure is often not complete, resulting in inhomogeneous bacterial cultures in which some clones have lost the plasmid and are thus not producing recombinant product any longer [4].

Further, chromosomal insertion of large DNA fragments into host cells is difficult. While strategies have been used to insert large DNA fragments into the *E. coli* genome [5], currently existing methods do not allow for the insertion of DNA fragments larger than 8 kb at desired sites in host cell genomes.

3 SUMMARY

In one aspect, provided herein are methods for inserting contiguous sequences of DNA, including large, contiguous sequences of DNA, into host cell genomes. Such DNA sequences may comprise multiple components, e.g., genes, promoters, terminators, etc., and can be selectively inserted at desired positions in host cell genomes. In certain embodiments, the DNA sequences, e.g., large DNA sequences, can be selectively inserted into regions of the host cell genome such that one or more components present in the fragments (e.g., genes) are expressed by the host cell, e.g., the host cell expresses one or more components (e.g., genes) that are not normally expressed by the host cell and/or the host cell expresses a component (e.g., a gene) that is naturally expressed by the host cell, but expresses more of such component. Methods of insertion of DNA are described in Section 5.1, below.

In a specific embodiment, provided herein is a method for inserting a large sequence of DNA into a host cell genome, wherein said large DNA sequence comprises one, two, three, four, five, or more genes. In certain embodiments, the genes present in the DNA sequences inserted into host cells in accordance with the methods described herein are under the control of one or multiple regulatory sequences or promoters that also are present in the DNA sequences. In certain embodiments, the DNA sequences inserted into host cells in accordance with the methods described herein may comprise additional elements essential to or beneficial to expression of the genes present in the large DNA sequence, e.g., enhancers, terminators.

In another specific embodiment, provided herein is a method for inserting a large sequence of DNA into a host cell genome, wherein said large DNA sequence comprises one or more operons, e.g., a cluster of genes under the control of a common regulatory signal or promoter.

In another specific embodiment, provided herein is a method for inserting a large sequence of DNA into a host cell genome, wherein said host cell genome further has a deletion of DNA that is normally associated with the host cell genome, i.e., the method results in both an insertion of heterologous DNA into the host cell genome and removal of normally present DNA from the host cell genome. In specific embodiments, the insertion of a large sequence of DNA is made at the site of the removal of a sequence of DNA from the host cell genome of the equivalent size, i.e., the DNA of the host cell genome is replaced by the inserted DNA sequence.

In certain embodiments, the methods described herein comprise the introduction of a helper plasmid and a donor plasmid into a host cell. As used herein, helper plasmids are meant to encompass plasmids that comprise elements (e.g., encode genes) that are required for the insertion of a large DNA sequence into the genome of a host cell. In accordance with the methods described herein, the helper plasmids do not incorporate any DNA into the host cell genome themselves, but rather facilitate the incorporation of insert DNA that is present in the donor plasmids described herein. Helper plasmids are described in greater detail in Section 5.1.1, below. As used herein, donor plasmids are meant to encompass plasmids that comprise the large DNA sequence to be inserted into a host cell genome, i.e., the donor plasmid "donates" part of itself to the host cell genome (i.e., the large DNA sequence to be inserted into the host cell genome is donated). In certain embodiments, the donor plasmids provided herein comprise other elements that are required or useful for insertion of the large DNA sequence into the host cell genome. Donor plasmids are described in greater detail in Section 5.1.2, below.

In another aspect, provided herein are host cells (e.g., prokaryotic host cells, e.g., *E. coli*) comprising genomes into which sequences of DNA, such as large sequences of DNA, have been inserted in accordance with a method described herein. Without being bound by theory, the methods described herein can be used to generate genetically stable host cells that are capable of producing proteins of interest, e.g., proteins for use as vaccines, glycosylated proteins, proteins for use in cosmetics, etc. As a result of the insertion methods provided herein, such host cells need not be maintained and/or propagated in the presence of certain markers, e.g., antibiotic selection markers, due to the fact that the DNA comprising genes of interest are inserted directly into the genome of the host cells.

In certain embodiments, the host cells described herein comprise a genome into which one or more DNA sequences has been inserted, wherein said DNA sequences encode a protein or comprise an operon/gene cluster involved in the glycosylation of proteins, e.g., N-glycosylation of proteins. For example, in certain embodiments, a host cell described herein comprises a genome into which one or more of the following has been inserted: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase.

In a specific embodiment, a host cell provided herein comprises a genome into which a DNA sequence has been inserted, wherein the inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a second DNA sequence, wherein said second inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a fourth DNA sequence, wherein said fourth DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is E. coli.

In another specific embodiment, a host cell provided herein comprises a genome into which a DNA sequence has been inserted, wherein the inserted DNA sequence comprises two or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the genome of the host cell additionally has inserted into it a second DNA sequence, wherein said second inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is E. coli.

In another specific embodiment, provided herein is a host cell comprising a donor plasmid and a helper plasmid, (a) wherein the helper plasmid comprises: (i) under control of a first promoter, an open reading frame encoding lambda red recombinase; and (ii) under control of a second promoter, an open reading frame encoding a restriction endonuclease that has a recognition sequence that is not present in the host cell genome; and (b) wherein the donor plasmid comprises: (i) from 5' to 3': (1) the recognition sequence of the restriction endonuclease; (2) a first homology region of at least 0.5 kilobases (kb), (3) a heterologous insert DNA of at least 8 kb; and (4) a second homology region of at least 0.5 kb; and (ii) a counterselection marker. In a specific embodiment, the recognition sequence comprises at least 18 base pairs. In another specific embodiment, the restriction endonuclease is SceI. In a specific embodiment, the heterologous insert DNA comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is E. coli.

Nucleic acid sequences encoding oligosaccharyl transferases that can be inserted into the host cells described herein are known in the art. In a specific embodiment, the oligosaccharyl transferase nucleic acid sequence inserted into the genome of a host cell described herein is an oligosaccharyl transferase nucleic acid sequence derived from a prokaryotic organism. In another specific embodiment, the oligosaccharyl transferase nucleic acid sequence inserted into the genome of a host cell described herein is an oligosaccharyl transferase nucleic acid sequence from the genus Campylobacter. In another specific embodiment, the oligosaccharyl transferase nucleic acid sequence inserted into the genome of a host cell described herein is an oligosaccharyl transferase nucleic acid sequence from Campylobacter jejuni (e.g., the pglB gene from C. jejuni). In another specific embodiment, the oligosaccharyl transferase nucleic acid sequence inserted into the genome of a host cell described herein is an oligosaccharyl transferase nucleic acid sequence derived from a eukaryotic organism.

Nucleic acid sequences encoding glycosyltransferases that can be inserted into the host cells described herein are known in the art. In certain embodiments, the glycosyltransferase nucleic acid sequence inserted into a host cell described herein is the nucleic acid sequence of a glycosyltransferase described in International Patent Application Publication No. WO 2011/138361, the disclosure of which is incorporated by reference herein in its entirety. In a specific embodiment, the glycosyltransferase nucleic acid sequence inserted into the genome of a host cell described herein is derived from a Gram-positive bacterium, e.g., the glycosyltransferase nucleic acid sequence is derived from S. aureus. In another specific embodiment, the glycosyltransferase nucleic acid sequence inserted into the genome of a host cell described herein is the glycosyltransferase nucleic acid sequence of capsular polysaccharide 5 from S. aureus.

In another specific embodiment, the glycosyltransferase nucleic acid sequence inserted into the genome of a host cell described herein is the glycosyltransferase nucleic acid sequence of capsular polysaccharide 8 from *S. aureus*. In another specific embodiment, the glycosyltransferase nucleic acid sequence inserted into the genome of a host cell described herein is derived from a Gram-negative bacterium, e.g., *E. coli*. In another specific embodiment, the glycosyltransferase nucleic acid sequence inserted into the genome of a host cell described herein is derived from a eukaryote.

Nucleic acid sequences encoding epimerases that can be inserted into the host cells described herein are known in the art. In certain embodiments, the epimerase nucleic acid sequence inserted into a host cell described herein is an epimerase nucleic acid sequence described in International Patent Application Publication No. WO 2011/062615, the disclosure of which is incorporated by reference herein in its entirety. In a specific embodiment, the epimerase nucleic acid sequence inserted into the genome of a host cell described herein is the epimerase nucleic acid sequence represented by the Z3206 gene of *E. coli* strain O157. See, e.g., WO 2011/062615 and Rush et al., 2009, The Journal of Biological Chemistry 285:1671-1680, which is incorporated by reference herein in its entirety.

Nucleic acid sequences comprising rfb gene clusters that can be inserted into the host cells described herein are known in the art. In a specific embodiment, the rfb gene cluster inserted into a host cell described herein is an rfb gene cluster from *E. coli*, e.g., an *E. coli* rfb cluster from any O serogroup/O antigen known in the art, e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, or O187, and subserotypes thereof. In another specific embodiment, the rfb gene cluster inserted into a host cell described herein is an rfb gene cluster from a *Pseudomonas* strain (e.g., a *P. aeruginosa* strain), a *Salmonella* strain (e.g., a *S. enterica* strain), a *Yersinia* strain, a *Klebsiella pneumoniae* strain, a *Francisella* strain (e.g., *F. tularensis*), an *Acinetobacter baumannii* strain, a *Burkholderia* strain, or a *Shigella* strain.

Nucleic acid sequences comprising capsular polysaccharide gene clusters that can be inserted into the host cells described herein are known in the art. In a specific embodiment, the capsular polysaccharide gene cluster inserted into a host cell described herein is a capsular polysaccharide gene cluster from an *E. coli* strain, a *Streptococcus* strain (e.g., *S. pneumoniae*, *S. pyrogenes*, *S. agalacticae*), a *Staphylococcus* strain (e.g. *S. aureus*), or a *Burkholderia* strain (e.g. *B mallei*, *B. pseudomallei*, *B. thailandensis*).

Nucleic acid sequences encoding carrier proteins that can be inserted into the host cells described herein are known in the art. The carrier proteins produced by the host cells described herein comprise at least one N-glycosylation consensus sequence, e.g., either the consensus sequence (i) Asn-X-Ser(Thr), wherein X is are independently selected from any amino acid except Pro; or (ii) D/E-X-N-Z-S/T, wherein X and Z are independently selected from any amino acid except Pro. Accordingly, the DNA sequences encoding carrier proteins inserted into the host cells described herein comprise at least one nucleic acid sequence within the carrier protein nucleic acid sequence that encodes an N-glycosylation consensus sequence. The DNA sequence encoding a carrier protein inserted into the host cells described herein can encode any carrier protein known in the art, including the carrier proteins described in Section 5.2.1.2, below. In a specific embodiment, the carrier protein nucleic acid sequence inserted into the genome of a host cell described herein is a nucleic acid sequence that encodes Exotoxin A of *P. aeruginosa* (EPA), including EPA that has been genetically modified to comprise at least one N-glycosylation consensus sequence. In another specific embodiment, the carrier protein nucleic acid sequence inserted into the genome of a host cell described herein is a nucleic acid sequence that encodes cholera toxin B. In another specific embodiment, the carrier protein nucleic acid sequence inserted into the genome of a host cell described herein is a nucleic acid sequence that encodes AcrA. In another specific embodiment, the carrier protein nucleic acid sequence inserted into the genome of a host cell described herein is a nucleic acid sequence that encodes HlA. In another specific embodiment, the carrier protein nucleic acid sequence inserted into the genome of a host cell described herein is a nucleic acid sequence that encodes ClfA.

In certain embodiments, the copy number of genes within the inserted DNA in a host cell described herein, e.g., heterologous insert DNA, is 1, 2, 3, 4, 5, 6, 7, 8, 9, or 10. In a specific embodiment, the copy number of genes within the inserted DNA in a host cell described herein, e.g., heterologous insert DNA is 1 or 2. In another specific embodiment, the copy number of genes within the inserted DNA in a host cell described herein, e.g., heterologous insert DNA is 1.

Exemplary prokaryotic host cells that can be used in accordance with the methods described herein include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

The DNA, e.g., heterologous insert DNA, inserted into the host cell genomes in accordance with the methods described herein may comprise a selection marker. In certain embodiments, when the inserted DNA, e.g., heterologous insert DNA, comprises a selection marker, the selection marker is flanked by flippase recognition target (FRT) sites. In certain embodiments, the first and second homology regions are homologous to adjacent regions of the host cell genome.

The first and second homology regions of the donor plasmids described herein can be of any size necessary or desired for the insertion of the heterologous insert DNA. For example, the homology regions can be about or at least 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2.0 kb, or greater than 2.0 kb. In certain embodiments, the first and second homology regions can be of the same size. In certain embodiments, the first and second homology regions can be different sizes.

In certain embodiments, the DNA, e.g., heterologous insert DNA, inserted into the host cells described herein using the methods provided herein is large in size, e.g., the DNA, e.g., heterologous insert DNA is of a size not able to be inserted into host cell genomes using standard methods known in the art. For example, in certain embodiments, the DNA, e.g., heterologous insert DNA, inserted into the host cells described herein using the methods provided herein is about or at least 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, or 25 kb.

3.1 Abbreviations and Terminology

As used herein, homology regions, abbreviated HR, refer to regions of DNA present on the donor plasmids described herein. HR are regions of DNA that are homologous to regions of DNA present on the genome of host cells into which DNA is meant to be inserted. In certain embodiments, the HR are at least 80%, 85%, 90%, 91%, 92%, 93%, 94%, 95%, 96%, 07%, 98%, 99%, or 99.5% homologous to regions of DNA present on the genome of host cells into which DNA is meant to be inserted. In certain embodiments, the HR are 100% homologous to regions of DNA present on the genome of host cells into which DNA is meant to be inserted. In certain preferred embodiments, the HR are at least 99.5% homologous to regions of DNA present on the genome of host cells into which DNA is meant to be inserted.

As used herein, target sites refer to sites present on the host cell genomes that are complementary to the homology regions of the donor plasmids described herein.

As used herein, heterologous insert DNA refers to sequences of DNA present in the donor plasmids described herein which are inserted into target host cell genomes using the methods described herein.

As used herein, in the context of DNA, insertion refers to the process of introducing heterologous insert DNA into another piece of DNA (e.g., a host cell genome), resulting in a DNA molecule (e.g., a modified host cell genome) that comprises the heterologous insert DNA.

As used herein, acceptor cells refer to host cells which are modified in accordance with the methods provided herein, e.g., acceptor cells comprise genomes which are modified to comprise heterologous insert DNA.

As used herein, cassette refers to a DNA sequence which contains a gene and its regulatory sequences required for phenotypic expression of the gene function, e.g., antibiotic resistance. Cassettes may also contain flanking sequences that facilitate removal of the cassette from the genome of an acceptor cell or from another DNA sequence (e.g., a plasmid).

Exemplary flanking sequences that may be associated with cassettes include flippase recognition target (FRT) sites. In accordance with the methods described herein, antibiotic selection (e.g., selection of host cells that express specific antibiotic resistance markers) may be performed using selection cassettes and antibiotics in the growth media. Cassettes can be abbreviated by the antibiotic abbreviation followed by a capital R for resistance, e.g., ampR refers cassette that confers resistance to ampicillin (amp). This nomenclature thus describes a phenotype rather than a genotype. Abbreviations for the antibiotics used in accordance with the methods described herein are provided in Table 6, below.

As used herein, O antigen cluster and rfb cluster refer to gene clusters responsible for the biosynthesis of O antigens [6].

As used herein, Undecaprenol phosphate is abbreviated as Und-P; and undecaprenol pyrophosphate is abbreviated as Und-PP.

As used herein, detoxified Exotoxin A of *Pseudomonas aeruginosa* is abbreviated as EPA. EPA described herein can be detoxified using methods known in the art [7].

*E. coli* strains from different collections are referenced herein. In such references, upecGVXN "number", CCUG "number", and StGVXN "number" denote strains from an epidemiology study collecting uropathogenic *E. coli*, the culture collection of Goteborg, Sweden, and the Glyco-Vaxyn strain collection, where "number" refers to the particular number assigned to the strain.

4 BRIEF DESCRIPTION OF THE DRAWINGS

FIG. 1. Schematic map of the donor plasmid pDOC-C and relevant elements. ampR: DNA cassette encoding the gene conferring beta lactam resistance; sacB: expression cassette conferring sensitivity to sucrose; oriT: origin of replication; MCS: multiple cloning site; SceI: homing endonuclease restriction site for mobilizing the DNA from the donor plasmid; DNA insert: DNA stretch replacing the acceptor cell DNA between HR1 and H1R2; HR1, HR2: homology regions 1 and 2, these are the DNA regions present in the host cell at which crossing over and homologous recombination occurs; selection cassette: selectable marker gene to screen for integrated clones, this cassette can be flanked by site specific homologous recombination sites which allow removal of the cassette; DNA of Interest: foreign DNA remaining in the target strain in place of the target strain DNA after selection cassette removal.

FIG. 2. Scheme of integration procedure. Different steps of the procedure are labeled by numbers in brackets. The target cell (rectangle) containing helper plasmid, donor plasmid (circles labeled pTKRED and pDOC) and chromosome (scribble) are grown (1) and induced with IPTG and arabinose (2) to induce expression of the homologous recombinase lambda red and the homing endonuclease SceI (scissors). The latter cuts the pDOC donor plasmid and thereby mobilizes the insert DNA resulting in the linearized insert DNA inside the cell (3). The linearized insert DNA is the optimal substrate for the lambda red recombinase which facilitates crossing over and homologous recombination at the homologous recombination sites HR1 and 2 (bold black bars). The enzymatic recombination is indicated by crossed over, thin black lines (4). The resulting strain contains the insert DNA in place of the DNA formerly present between HR1 and 2. Helper and donor plasmids are then lost ('cured') from the target cell by different procedures as indicated in the text.

FIG. 3. (A) The top panel shows the *E. coli* O1 rfb cluster of a donor plasmid and the flanking HRs are indicated with thin lines that connect to the target sites (sites homologous to the HR regions in the Insert DNA) in the acceptor genome of strain W3110; italics show the gene names, empty arrows indicate genes from donor plasmids, filled arrows the acceptor rfb cluster from W3110, which is removed after integration. Black, narrow, filled boxes indicate the site specific recombination sites for clmR removal by FLP mediated site specific recombination. The large filled rectangle indicates the wbbL gene of W3110 including the disrupting insertion element which renders the strain W3110 O antigen negative. Thin arrows and numbers indicate the annealing regions and numbers of oligonucleotides used for PCR tests and the donor plasmid cloning. (B) depicts the results of colony PCR to confirm the presence of the O1 rfb cluster in cells. The bottom panels are PCR test reactions separated on agarose gels by electrophoresis, stained with Gel Red DNA stain, and illuminated with UV light to visualize DNA. PCR reactions contained the oligonucleotides 2241 and 2242 (see A), and resuspended colonies of control strains and strains after rfb cluster insertion, waaL deletion, and selection cassettes removal: 1, W3110 ΔO16::O1-clmR; 2, W3110 ΔO16::rfbO1; 3, W3110 ΔO16::rfbO1 ΔwaaL::clmR; 4, W3110 ΔO16::rfbO1 ΔwaaL, 5, W3110 ΔwaaL; 6, W3110.

FIG. 4. Test of O1-sugar expression at different stages of strain construction. Proteinase K treated whole cell extracts from *E. coli* cells after integration of the rfb cluster (W3110 ΔrfbO16::rfbO1-clmR, panel A), removal of the clmR cassette (W3110 ΔrfbO16::rfbO1, panel B), waaL disruption (W3110 ΔrfbO16::rfbO1 ΔwaaL::clmR, panel C), and clmR cassette removal from the waaL deletion (W3110 Δrfb016:: rfbO1 ΔwaaL, panel D). Cultures were grown in LB medium, incubated overnight at 37° C., and cell lysates were treated by dissolving in SDS Lämmli sample buffer and incubating with proteinase K at 65° C. for 1 h. Extracts were separated by SDS PAGE, and either directly developed using silver staining (to visualize LPS, A, C, D top panels), or transferred to nitrocellulose membranes by electrotransfer followed by immunodetection with anti-O1 antiserum (αO1; A, B, C, D bottom panels). Controls were analyzed in parallel (Panels A, B: upecGVXN140, it is a clinical isolate which was used to amplify the O1 rfb cluster for subsequent integration). Lane numbers are indicated and strain designations are given in the black boxes. M: marker lane, molecular weights are indicated in kDa. Rows labeled "Clone" indicate different analyzed clones from an experiment.

FIG. 5A and FIG. 5B. *E. coli* O1 O antigen analysis from strain W3110 ΔrfbO16::rfbO1 ΔwaaL by 2 AB labelling and MS/MS. FIG. 5A HPLC analysis of *E. coli* O1 recombinant O antigen. Cellular extracts were processed as described: dried organic extracts from cells were hydrolyzed and purified. Resulting Und-PP linked polysaccharides were released from lipid, further purified, and labeled by reductive amination at the reducing end with 2 AB. Fluorescence emission was measured upon separation of the labeled polysaccharides by normal phase HPLC on a GlycoSepN column. The chromatogram (solid) is the fluorescence trace in dependence of the elution time (strain W3110 ΔrfbO16:: rfbO1 ΔwaaL). The dotted trace is a control sample not expressing O antigen (W3110 ΔwaaL). 1, 2, 3, 4 asterisk indicate peaks that correspond to 1, 2, 3 and 4 O antigen repeat units; 5 asterisk are a fragment of the 6 repeat units molecule. FIG. 5B MALDI-TOF/TOF analysis of the two asterisk HPLC elution fraction from panel A. [m/z]=1849, corresponding to the expected mass of two O1 repeat unit Na+ ion adduct, was selected for MS/MS, and Y fragment ions series confirming the expected monosaccharide sequence are indicated.

FIG. 6. Small scale expression test of EPA-O1 glycoprotein by the inserted strain for O1 glycosylation of EPA 4 sites. *E. coli* cells (W3110 ΔrfbO16::rfbO1 ΔwaaL) were transformed with an EPA expression plasmid (p659) and five different pglB expression plasmids as described in the Examples, below. Cells were grown and induced with arabinose and IPTG, after overnight incubation at 37° C., cells were harvested and periplasmic protein extracts were prepared. Extracts were then separated by SDS PAGE, transferred to nitrocellulose membranes by electroblotting, and immunodetected. Left panel: Western blot using anti-EPA antiserum, right panel: Western blot using anti-O1 antiserum. PglB plasmids are indicated above the lanes (A, p114: expression of non-codon optimized, HA tag containing pglB; B, p939: codon optimized, HA tag containing; C, p970: codon optimized, HA tag removed; D, codon optimized, HA tag containing, natural glycosylation site N534Q removed; and E, codon optimized, HA tag removed, natural glycosylation site N534Q removed); molecular weight marker lane sizes are indicated.

FIG. 7. PCR screening of colonies from strain construction of the *E. coli* O2 O antigen conjugate production strains at different stages of construction. *E. coli* cells from insertion experiments as indicated in the text were tested for genotyping characteristics by PCR using specific oligonucleotides. A. The top panel shows the rfb cluster in the donor plasmid and the flanking HR indicated with thin lines that connect to the target sites in the acceptor genome of strain W3110; italics show the gene names, empty arrows the genes from donor plasmids, filled arrows the acceptor rfb cluster. Black, narrow, filled boxes indicate the site specific recombination sites for clmR removal by FLP mediated site specific recombination. The large filled rectangle indicates the disrupted wbbL gene of W3110 including the insertion element. Thin arrows and numbers indicate the annealing regions of oligonucleotides used for PCR tests and the donor plasmid cloning. B. The bottom panels are Gel Red stained electrophoresed agarose gels illuminated with UV light to visualize products of the PCR test reactions to test deletion of waaL. PCR reactions contained the oligonucleotides 1114 and 1326, and resuspended colonies of control strains and strains after integration, waaL disruption, and selection cassettes removal: 1, St4043=W3110 ΔO16::O2-kanR; 2, St4044=W3110 ΔO16::O2-kanR ΔwaaL::clmR; 3, W3110 ΔrfbO16::rfbO2 ΔwaaL; 4 W3110 ΔwaaL; 5, W3110; 6, W3110 ΔwaaL::clmR. Expected amplicon sizes are 1.7 kb for unmodified sequence, 1.5 kb for clmR insertion, 0.5 kb after clmR cassette removal.

FIG. 8. Test of O2 O antigen expression at different stages of strain construction. Proteinase K treated whole cell extracts from *E. coli* cells after integration of the rfb cluster (W3110 ΔrfbO16::rfbO2-kanR, panel A), and waaL disruption followed by clmR and kanR cassette removal (W3110 ΔrfbO16::rfbO2 ΔwaaL, panel B), were prepared from cultures grown in LB medium, incubated overnight at 37° C. Cell lysates were treated by dissolving in SDS Lämmli sample buffer and incubation with proteinase K at 65° C. for 1 h. Extracts were then separated by SDS PAGE, and either directly developed using silver staining (to visualize LPS, panel B, left), or transferred to nitrocellulose membranes by electroblotting, and immunodetected with anti O2 antiserum (αO2), to detect Und-PP linked O6 polysaccharide (Und-PP linked O antigen, panel A, B right side). Control samples were analyzed in parallel, in most cases the parental ancestor strains. Lane numbers are indicated and strain designations are given in the black boxes. Panel A: lane 2 contains an extract from a clinical isolate which was used for generating the DNA of interest by PCR (upecGVXN116). Panel B: lane 2 contains the inserted strain before waaL deletion.

FIG. 9A and FIG. 9B. *E. coli* O2 O antigen expression from strain W3110 ΔrfbO16::rfbO2 ΔwaaL by 2 AB labelling. Cells were processed as described: dried organic extracts from cells were hydrolyzed and purified. Polysaccharides were labeled by reductive amination at the reducing end with 2 AB and analyzed by normal phase HPLC on a GlycoSepN column. FIG. 9A HPLC analysis of E. coli O2 recombinant O antigen from strain W3110 ΔrfbO16::rfbO2 ΔwaaL.

The chromatogram (solid line) is the fluorescence trace in dependence of the elution time. The dotted trace is a control sample not expressing O antigen. 1, 2, 3 asterisks indicate peaks that correspond to peaks with elution times consistent with 1, 2, and 3 O antigen repeat units. FIG. 9B MALDI-TOF/TOF analysis of the peak fraction labeled by two asterisks in panel A. [m/z]=1817, corresponding to the expected mass of two O2 O antigen repeat units with an Na$^+$ ion attached, was selected for MS/MS, and Y fragment ions series confirming the correct monosaccharide sequence are indicated.

FIG. 10. Small scale test of integrated strains for O2 glycosylation of EPA 4 sites. E. coli cells (W3110 ΔrfbO16::rfbO2 ΔwaaL) were transformed with p659 and two different pglB expression plasmids as described in the text. Cells were grown and induced with arabinose and IPTG, after overnight incubation at 37° C., cells were harvested and periplasmic protein extracts were prepared. Extracts were then separated by SDS PAGE, transferred to nitrocellulose membranes by electroblotting, and immunodetected. Left panel: Western blot using anti EPA antiserum (αEPA), right panel: Western blot using anti O2 antiserum (αO2). Plasmids are indicated above the lanes by capital letters (B, codon optimized, HA tag containing pglB expression plasmid (p939), D, codon optimized, without HA tag (p970)), molecular weight marker lane sizes are indicated. As control, an extract from clinical E. coli isolate upecGVXN124 (StGVXN3947) containing p659 and p939 was analyzed (lane x).

FIG. 11. PCR screening of colonies from strain construction of the E. coli O6 O antigen conjugate production strains at different stages of construction. E. coli cells from integration experiments as indicated in the Examples were tested for genotyping characteristics by PCR using specific oligonucleotides. Panel A shows the rfb cluster in the donor plasmid and the flanking HR indicated with thin lines that connect to the HR regions in the acceptor sites in the W3110 genome; italics show the gene names, empty arrows the genes from donor plasmids, filled arrows the acceptor rfb cluster in W3110. Black, narrow, filled boxes indicate the site specific recombination sites for kanR removal by FLP recombination. The large filled box indicates the disrupted wbbL gene of W3110. Thin arrows and numbers indicate the annealing regions and numbers of oligonucleotides used for PCR tests and the donor plasmid cloning. The bottom panels (B-D) are Gel Red stained agarose gels illuminated with UV light to visualize products of the PCR test reactions. PCR reactions contained the oligonucleotides indicated above the panels, and resuspended colonies of control strains and strains after integration, waaL disruption, and selection cassettes removal: 1, W3110; 2, W3110 ΔwaaL; 3, W3110 ΔrfbO16::rfbO6-kanR ΔwaaL; 4 and 5, two different clones of W3110 ΔrfbO16::rfbO6 ΔwaaL. The oligonucleotide pairs tested are indicated. PCR for testing the 5' HR region transition (panel B) results in a PCR product of 1.697 kb, for the 3' HR transition 3.6 kb or 2.3 kb in presence or absence of the kanR cassette (panel C), and 0.783 kb for the O6 wzy (c2564) PCR (panel D).

FIG. 12. Test of O6 O antigen expression at different stages of strain construction. Proteinase K treated whole cell extracts from E. coli cells after integration of the rfb cluster (W3110 ΔrfbO16::rfbO6-kanR, panel A), waaL disruption (W3110 ΔrfbO16::rfbO6-kanR ΔwaaL::clmR, panel B), and clmR cassette removal (W3110 ΔrfbO16::rfbO6-kanR ΔwaaL, panel C), were prepared from culture grown in LB medium, incubated overnight at 37° C. Cell lysates were prepared by dissolving cell pellets in SDS Lämmli sample buffer and incubation with proteinase K at 65° C. for 1 h. Extracts were then separated by SDS PAGE, and either directly developed using silver staining (to visualize LPS, panel B and C, left), or transferred to nitrocellulose membranes by electroblotting, and immunodetected with anti O6 antiserum (αO6), to detect lipid linked O6 polysaccharide (O antigen, panel A, B right side, C right side). Control samples were analyzed in parallel, in most cases the direct ancestor strains as indicated. Lane numbers are indicated and strain designations are given in the black boxes. Panel A: lane 3 contains an extract from a wild type E. coli O6 strain (CCUG27).

FIG. 13. Small scale test of integrated strains for O6 glycosylation of EPA encoding 4 sites. E. coli cells (W3110 ΔrfbO16::rfbO6-kanR ΔwaaL) were transformed with EPA (p659) and a pglB expression plasmid (codon optimized, HA tag containing pglB expression plasmid, p939) as described in the text. Cells were grown and induced with arabinose and IPTG, after overnight incubation at 37° C., cells were harvested and periplasmic protein extracts were prepared. Extracts were then separated by SDS PAGE, transferred to nitrocellulose membranes by electroblotting, and immunodetected. Left panel: western blot using anti EPA antiserum (αEPA), right panel: western blot using anti O6 antiserum (αO6).

FIG. 14. Comparative analysis of different glycoconjugate production systems. Different E. coli ΔwaaL cells producing O1 (panel A), O2 (panel B), and O6 (panel C) O antigen were transformed with p659 and p939 (codon optimized pglB with C terminal HA tag) and tested for expression of the glycoconjugate. Expression cultures were grown in TB medium supplemented with 10 mM MgCl$_2$ at 37° C. Cultures were induced at OD600 of 0.4-1.2 by 0.2% arabinose and 1 mM IPTG addition. Cells were harvested after overnight induction (20 hrs), and periplasmic extracts were prepared by the lysozyme method. Extracts were then separated by SDS PAGE, transferred to nitrocellulose membranes by electroblotting, and immunodetected using anti EPA antiserum (A, B and C, left panel), and O1, O2, or O6 O antigen specific antisera (A, B, C, right panels). Host cells were either clinical E. coli isolates (lanes 1), inserted W3110 cells as described in this patent application (lanes 2: A, W3110 ΔrfbO16::rfbO1 ΔwaaL, B, W3110 ΔrfbO16::rfbO2 ΔwaaL, C, W3110 ΔrfbO16::rfbO6-kanR ΔwaaL), or W3110 ΔwaaL cells containing the respective rfb cluster on a cosmid (pLAFR) (lanes 3). Molecular size marker masses are indicated, as well as the probing sera used for each Western blot.

FIG. 15. PCR screening of colonies from integration of the P. shigelloides O17 rfb cluster in W3110 strains. E. coli cells from integration experiments as indicated in the text were tested for genotyping characteristics by PCR using specific oligonucleotides. Two different acceptor strains were tested, W3110 and W3110 ΔwecA-wzzE ΔwaaL. The top panel (A) shows the P. shigelloides rfb cluster in the donor plasmids (without and with wzz) and the flanking HR in black boxes, and the target site in the W3110 genome, italics show the gene names, empty arrows the genes from donor plasmids, empty from acceptor sites. Black, narrow, filled boxes indicate the site specific recombination sites for clmR removal by FLP driven, site specific recombination. The large filled box indicates the wbbL gene region of W3110 naturally disrupted by an insertion element. Arrows and numbers indicate the annealing location and names of oligonucleotides used for PCR tests. The following pairs were tested: a) 1226 and 1227 for confirming the deletion of E. coli O16 wzy, resulting in absence of a PCR product when wzy is deleted, and in a 0.9 kb product when wzy is present; b) 1549 and 1550 for presence of P. shigelloides wzy & wbgV, resulting in a 1.522 kb product; c) 1284 and 1513 for the HR1 transition region resulting in a 2.545 kb product with wzz and 1.403 kb by clones without wzz. B: agarose gel electrophoresis of PCR reaction mixtures containing integration colony lysates (white numbers) and the indicated oligonucleotide pairs. Absence of wzy of O16, presence of wzy-wbgV and the HR1 (5') transition regions are indicative for successful integration. DNA marker band sizes are indicated. The following strains were confirmed: W3110 ΔwecA-wzzE ΔwaaL ΔrfbO16::rfbPsO17-clmR without wzz: clone 3, W3110 ΔwecA-wzzE ΔwaaL ΔrfbO16::PsO17-clmR with wzz clone 51, W3110 ΔrfbO16::rfbPsO17-clmR without wzz clone 7, and W3110 ΔrfbO16::rfbPsO17-clmR with wzz clone 46.

FIG. 16. Test of P. shigelloides O antigen expression at different stages of strain construction. E. coli cells from insertion experiments and selected by PCR screening were tested for glycolipid production by silver staining (left panel) and Western blotting using anti S. sonnei antiserum (right panel). W3110 ΔwecA-wzzE ΔwaaL ΔrfbO16::rfbPsO17-clmR without wzz: clone 3 (lane 3), W3110 ΔwecA-wzzE ΔwaaL ΔrfbO16::rfbPsO17-clmR with wzz clones 51 (lane 4), W3110 ΔrfbO16::rfbPsO17-clmR without wzz clones 7 (lane 1), and W3110 ΔrfbO16::rfbPsO17-clmR with wzz clone 46 (lane 2).

FIG. 17. Test of S. dysenteriae type 1 O antigen expression after integration of the rfp and rfb gene cluster replacing the rfb cluster of W3110. As target strains for insertion W3110 as well as W3110 ΔwaaL cells were used. E. coli clones from insertion experiments were screened by colony PCR. glycolipid production was analyzed by silver staining (left panel) and Western blotting against anti S. dysenteriae type 1 antiserum (right panel). Lanes 3, 4: W3110 as well as W3110 ΔwaaL strains after integration; lanes 1, 2: W3110 as well as W3110 ΔwaaL after integration and removal of the clmR cassette.

FIG. 18A and FIG. 18B. *S. dysenteriae* type 1 O antigen expression analysis by 2 AB labelling and HPLC. W3110 ΔrfbO16::rfbSd1 ΔwaaL was processed as described in the Examples. The chromatogram (FIG. 18A) is the fluorescence trace in dependence of the elution time. Asterisks indicate peaks that correspond to peaks with elution times consistent with 2(), 3, (*) and 4 (**) O antigen repeat units as analyzed by MALDI-TOF/TOF MS (FIG. 18**.B) [8, 9].

FIG. 19. *S. dysenteriae* type 1 O antigen glycoconjugates were produced in W3110 ΔrfbO16::rfbSd1 ΔwaaL using p293 and p114. A. SEC HPLC analysis. B. PMP labelling for monosaccharide composition analysis. A monosaccharide mix was used to calibrate for elution times of Glucose, Rhamnose and 2-N-Acetylglucosamine. C.SDS PAGE separation of glycoconjugate and detection by coomassie blue straining and anti *S. dysenteriae* 1 antiserum detection after electrotransfer to nitrocellulose membranes. D. Hydrazinolysis analysis. Polysaccharide in the glycoprotein preparation was detached from the protein by hydrazinolysis, labeled by 2 AB and analyzed by HPLC. Indicated peaks were collected and MS/MS analysis was consistent with 2 or 3 repeat unit O antigen structure.

FIG. 20. Test of *S. flexneri* glycolipid expression after exchange of the branching glucosyltransferase gtrS by gtrII or gtrX. A. The repeat unit structures of the relevant O antigens. The figure shows that *S. flexneri* 2a and 3a differ by the attachment site of the branching glucose residue. Anti group II and anti group 7, 8 antisera are able to discriminate between those attachments sites. B. Colony PCR analysis of gtrIIintegration into the W3110 genome. The gtrS gene was replaced by an amplicon consisting of gtrII fused to a clmR cassette. The cartoon shows the chromosome stretch around the gtr cluster after successful homologous recombination, with the clmR cassette still present. Arrows indicate the annealing positions for oligonucleotides used for colony PCR. Lane 1 (W3110 ΔwbbIJK ΔgtrS::gtrII-clmR) shows the result of a colony PCR with an recombined clone, lane 2 (W3110 ΔwbbIJK) is the control. The clmR cassette is flanked by difsites that induce excision of the cassette by site specific recombination by the Xer recombinase from *E. coli*. This means that in the colony PCR, bands corresponding to the stretch containing and lacking the clmR cassette are observed (expected sizes are 2.8 and 1.8 kb). The control shows a band at 1.6 kb as expected for the mother strain. C. W3110 *E. coli* cells containing the *S. flexneri* 2457T rfb cluster on a plasmid were analyzed by silver strain (left panel), anti group II antiserum and anti group 7,8 antiserum Western blotting (middle and right panels). Lane 1: W3110; lane 2: W3110 ΔgtrS::gtrII; lane 3: W3110 ΔgtrS::gtrX.

FIG. 21. *S. flexneri* type 2a O antigen glycoconjugates were produced in W3110 ΔrfbO16::rfbpSf2a ΔwaaL using p293 and p114. A. SDS PAGE separation of glycoconjugate and detection by coomassie blue straining and anti type II antiserum detection after electrotransfer to nitrocellulose membranes. B. SEC HPLC analysis of purified EPA glycoprotein. C. PMP labelling for monosaccharide composition analysis. Monosaccharides were used to calibrate for elution times of Glucose, Rhamnose and Glucosamine. Elution times are indicated by arrows. D. hydrazinolysis analysis. Polysaccharide in the glycoprotein preparation was detached from the protein by hydrazinolysis, labeled by 2 AB and analyzed by HPLC. Indicated peaks were collected and MS/MS analysis was consistent with 2 or 3 repeat unit O antigen structure and fragments thereof. Importantly, the glucose branch was clearly detected by MSMS (not shown).

FIG. 22. Sera from injected Sprague Dawley rats were analyzed for IgG titers against *S. flexneri* 2a LPS. Log titers are shown from each individual rat serum. Sera were harvested 2 weeks after the third injection. Corresponding level of anti 2a IgG reached 2 weeks after the third injection (post 3) and the statistical difference among groups (according to Mann-Whitney test) is shown. The specific IgG titer of animal sera has been detected using an enzyme-linked immunosorbent assay (ELISA). The 2a LPS, extracted from *S. flexneri* 2a strain ATCC700930, is adsorbed to the wells of a microplate. The 2a antibody titer is then determined by the addition of serial dilutions of the sera to be analyzed. Horseradish-peroxidase coupled to anti-rat/or anti-mouse IgG secondary antibody is used in an enzymatic, colorimetric reaction to determine the titer. End point titer is defined as the highest dilution above the preimmune pool average+3 times the standard deviation of the preimmune sera, and expressed as Log 10.

FIG. 23. Test of *P. aeruginosa* O11 O antigen expression after integration of the PA103 O antigen cluster. *E. coli* cells from integration experiments and selected by PCR screening and phenotypic testing were analyzed for glycolipid production by Western blotting against anti *P. aeruginosa* group E antiserum. Integrated target strains (lanes 1-4) and control extracts originating from DH5α cells containing the donor plasmids p1012 (lane 5) and p1013 (lane 6) were analyzed.

FIG. 24. Integration of a 16 kb chimeric cluster composed of the *P. aeruginosa* O11 rfb cluster containing a cassette (composed of the cap5HIJK genes fused to a clmR cassette) which replaced the O11 wzy and wbjA results in cells that can make recombinant glycoconjugate. Whole cell extracts were prepared from overnight grown cells and lysed in SDS Lämmli buffer and treated with proteinase K for 1 hr. SDS PAGE was used to separate the glycolipids from these samples, and silver staining or Western blotting against anti CP5 antiserum was used to identify CP5 polysaccharide. Lanes 1-3: integrated clones constructed with p471, p477, or p498. p471 contains HR 1 and 2 corresponding to the DNA upstream of the wecA and downstream of wzzE ORF sequences from W3110. Insertion was done into W3110 host cells. Donor plasmids were also used to prepare control extracts in DH5α cells which were analyzed in lanes 5, 6, and 7 (p498, p477, or p471); lane 4 contains a negative control (p473). Lane 8 represents a positive control prepared from extracts of W3110 ΔwecA cells containing plasmid p393, which produces CP5 polysaccharide [10].

Figure 27:
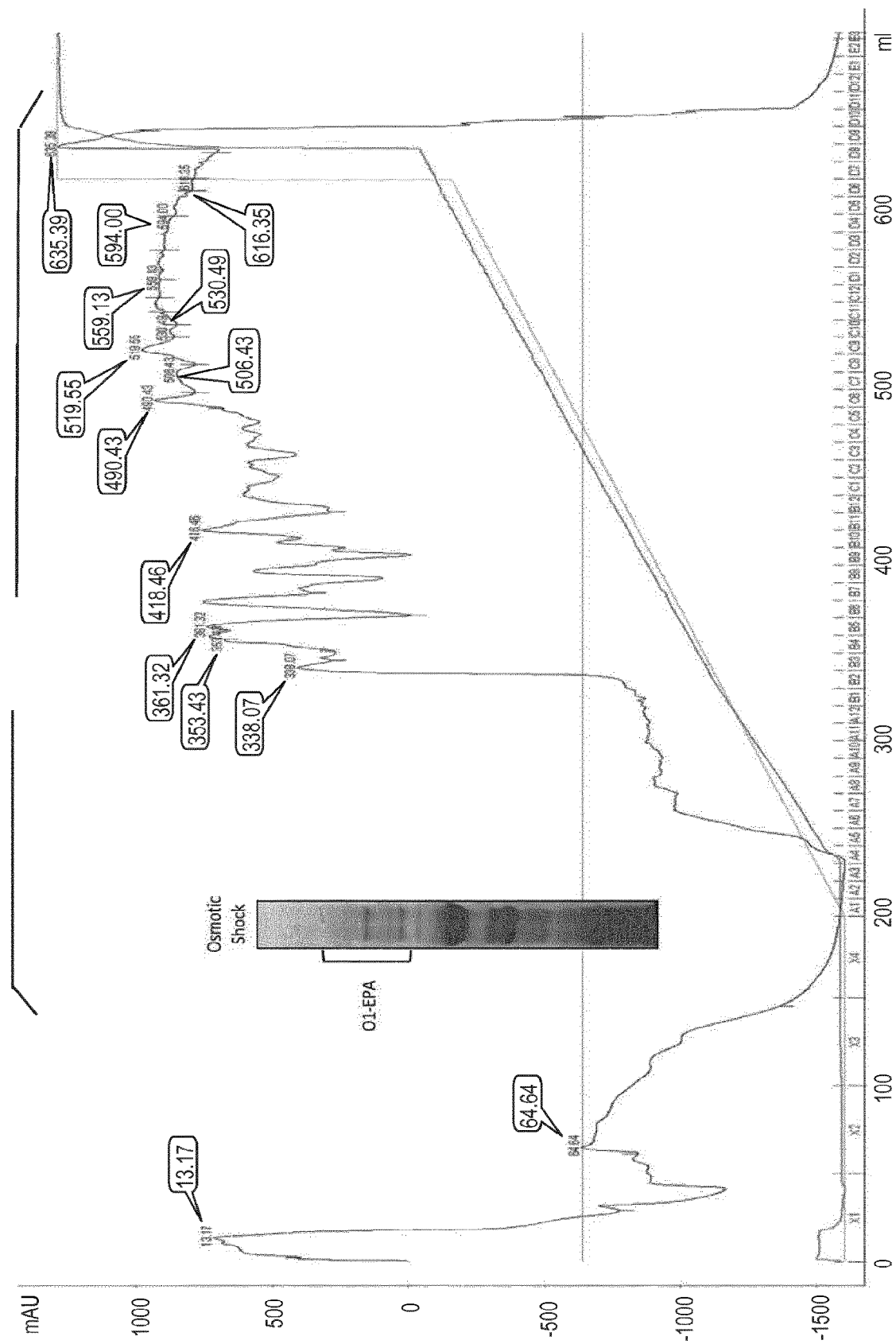

FIG. 27 depicts a chromatogram of the crude extract obtained following osmotic shock of host cells comprising pglB inserted into the host cell genome and harboring plasmids that produce a sugar antigen (*Shigella* O1) and a carrier protein (EPA). The chromatogram depicts results of running the osmotic shock fraction over a first Anionic exchange column (Source Q). O1-EPA identified in pooled fractions A6-A9 of the crude extract is depicted on Coomasie-stained gel (inset).

Figure 28:
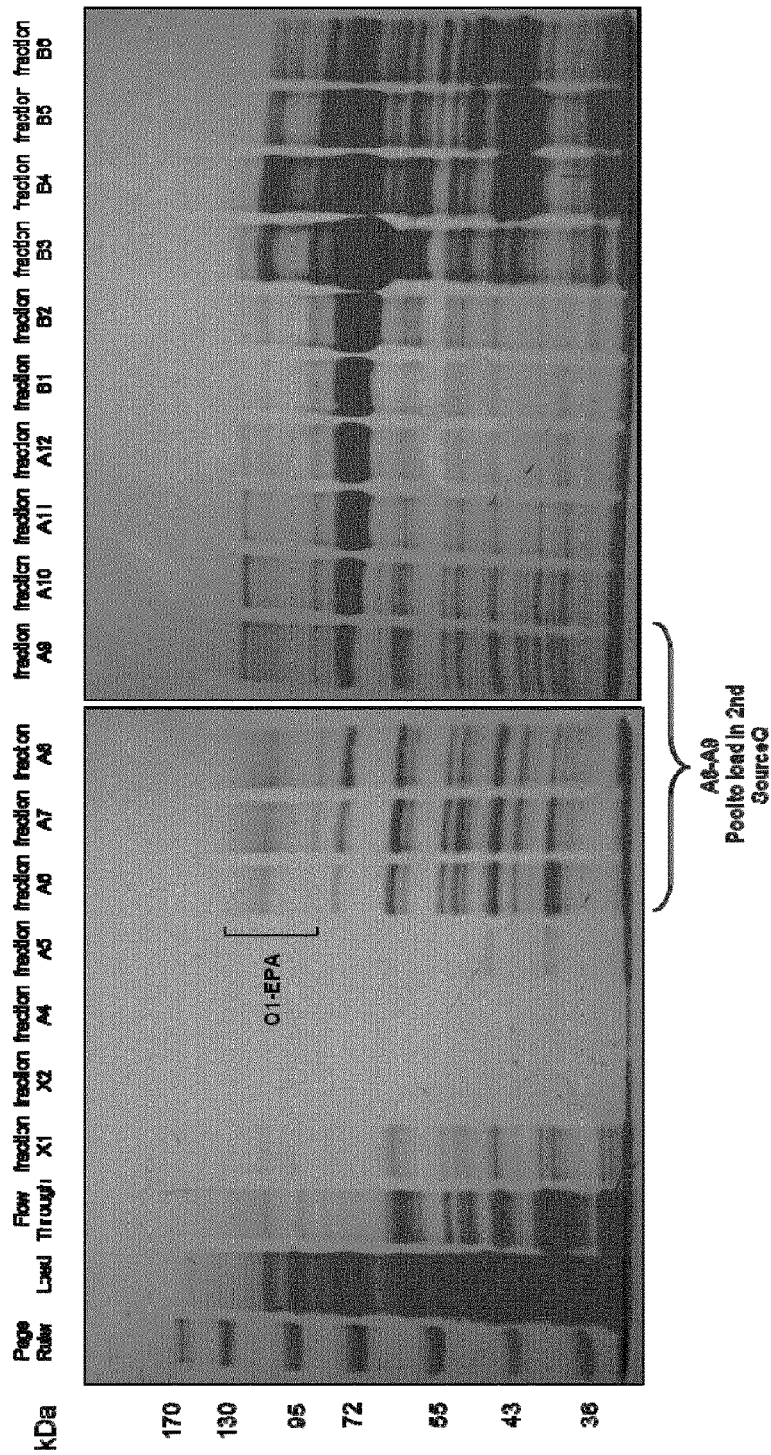

FIG. 28 depicts results of Coomasie staining of proteins present in the fractions obtained from running proteins isolated from the periplasm of cultured MG1655 waaL:: pglB-galK *E. coli* host strain harboring a plasmid that expresses an O1 antigen and a plasmid that expresses EPA over a first Source Q column.

Figure 29:
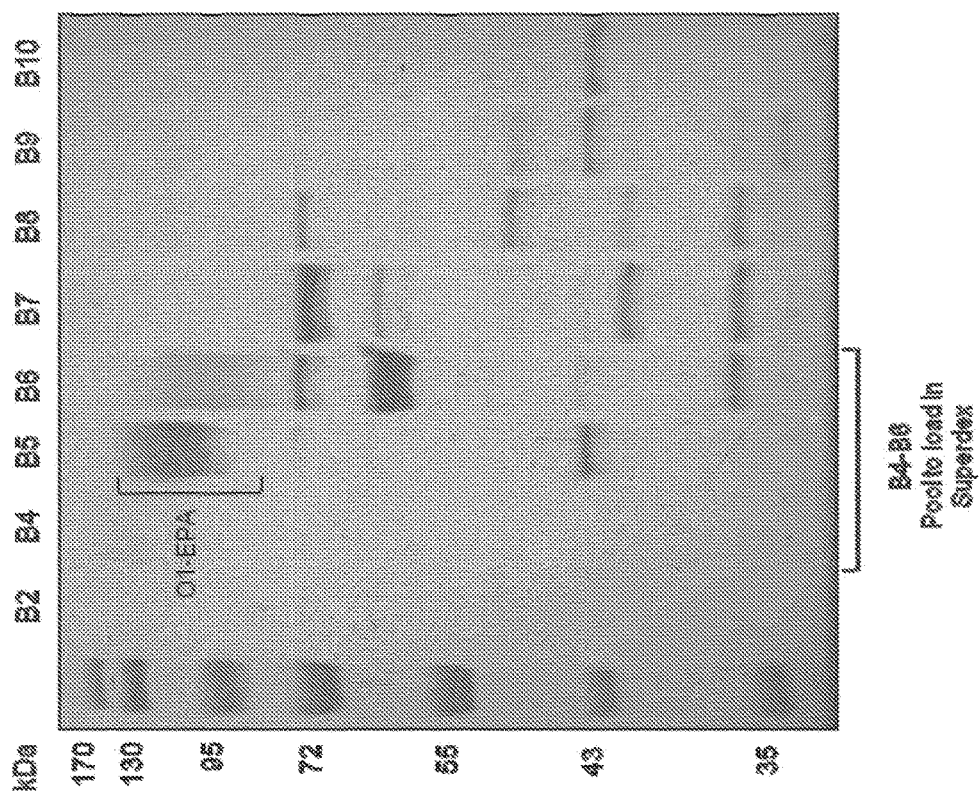

FIG. 29 depicts results of Coomasie staining of proteins present in the fractions obtained from running proteins isolated from the periplasm of cultured MG1655 waaL:: pglB-galK *E. coli* host strain harboring a plasmid that expresses an O1 antigen and a plasmid that expresses EPA over a second Source Q column.

Figure 30:
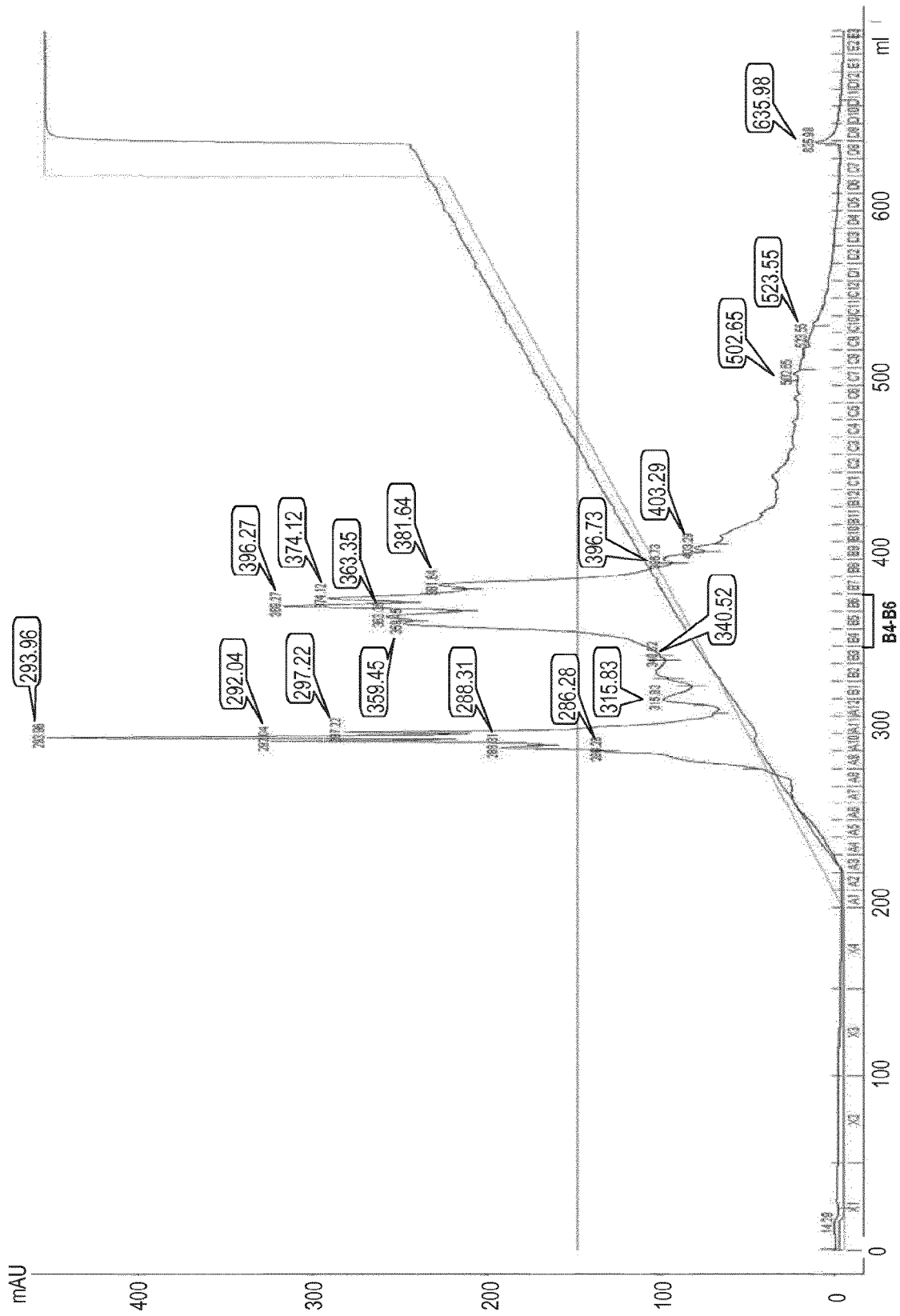

FIG. 30 depicts a chromatogram of the product obtained after host cells comprising pglB inserted into the host cell genome and harboring plasmids that produce a sugar antigen (*Shigella* O1) and a carrier protein (EPA) were subjected to osmotic shock, run over a first Anionic exchange column (Source Q) and run over a second Anionic exchange column (Source Q).

Figure 31:
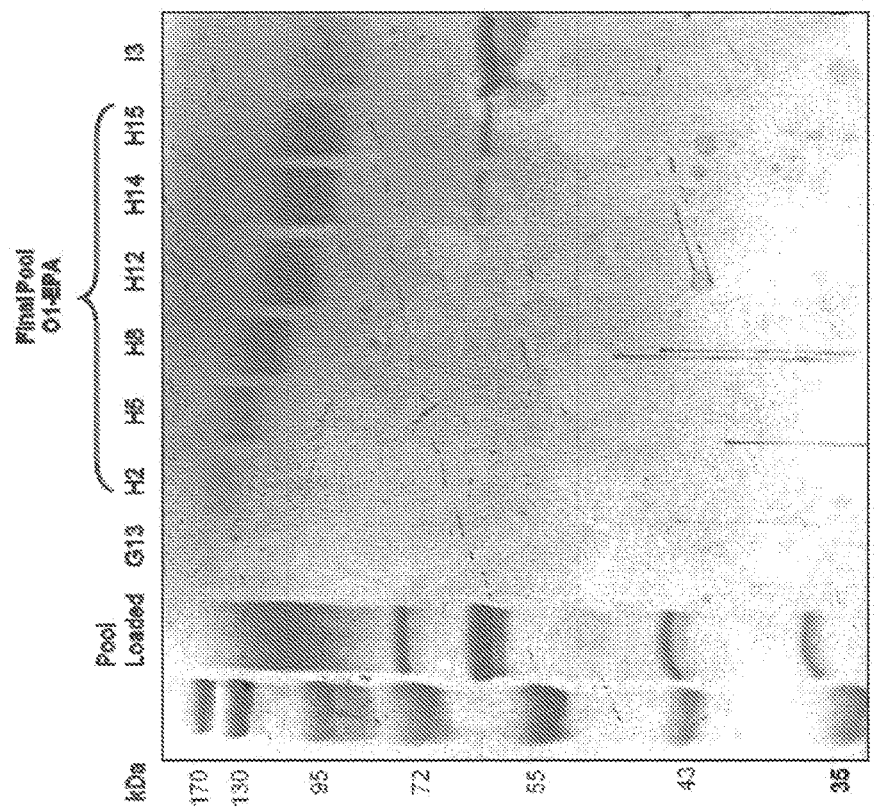

FIG. 31 depicts results of Coomasie staining of proteins present in the fractions obtained from running proteins isolated from the periplasm of cultured MG1655 waaL:: pglB-galK *E. coli* host strain harboring a plasmid that expresses an O1 antigen and a plasmid that expresses EPA over a Superdex 200 column.

Figure 32:
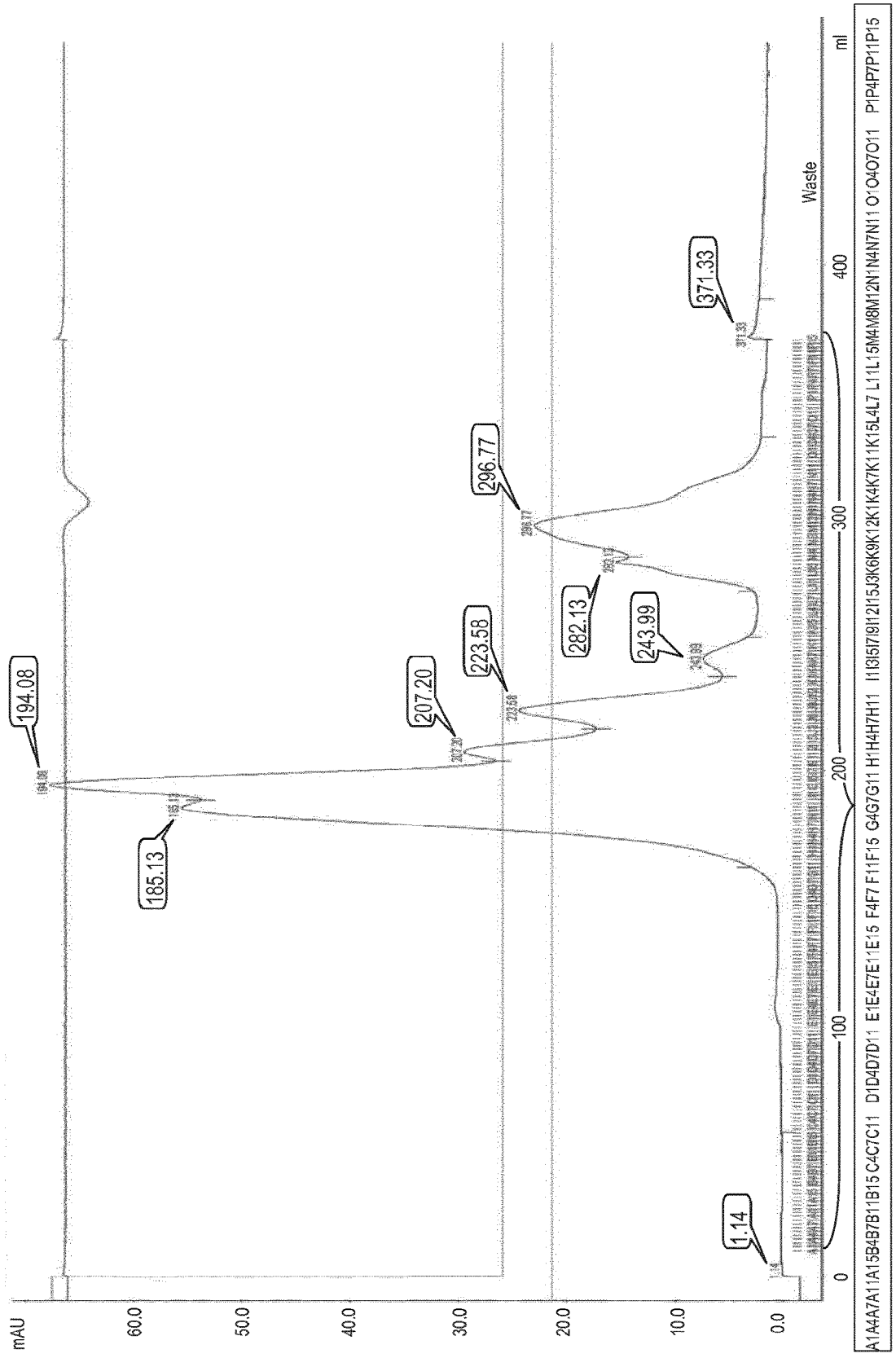

FIG. 32 depicts a chromatogram of the product obtained after host cells comprising pglB inserted into the host cell genome and harboring plasmids that produce a sugar antigen (*Shigella* O1) and a carrier protein (EPA) were subjected to osmotic shock, run over a first Anionic exchange column (Source Q), run over a second Anionic exchange column (Source Q), and run over a Superdex 200 column.

Figure 33:
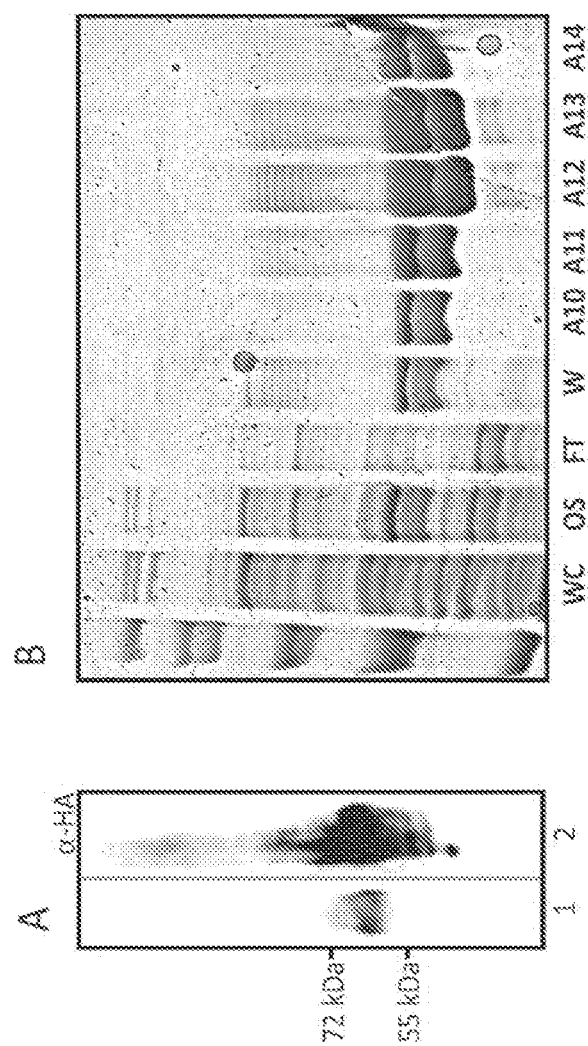

FIG. 33 (A) Whole-cell extracts from *E. coli* strain W3110 ΔrfbO16::rfb2457T, ΔgtrS::gtrII, ΔwaaL, ::$p_{O121}$pglB (lane 1) and *E. coli* strain W3110 ΔrfbO16::rfb2457T, ΔgtrS:: gtrII, ΔwaaL containing p114 (lane 2) were analyzed by SDS-PAGE and HA-tagged PglB was detected by Western blot using an anti-HA antibody. (B) Bioconjugate was produced in *E. coli* strain W3110 ΔrfbO16::rfb2457T, ΔgtrS:: gtrII, ΔwaaL, ::$p_{O121}$pglB transformed with p150. EPA was purified from periplasmic extracts using affinity chromatography. Purification of EPA was analyzed by SDS-PAGE followed by Coomassie blue staining. (WC: whole cell extract; PE: periplasmic extract; FT: flow-through that did not bind to affinity chromatography column; W: wash fraction of affinity column; A10-A14: elution fractions of affinity column.)

Figure 34:
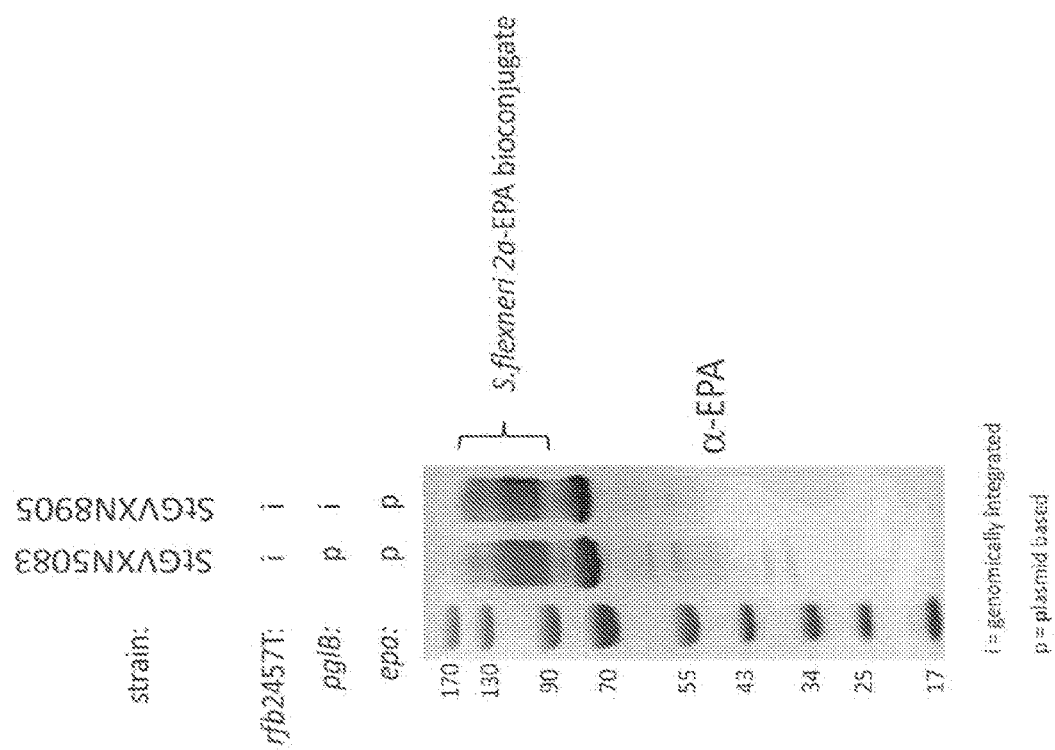

FIG. 34 depicts bioconjugate expression by *E. coli* strains expressing an oligosaccharyl transferase, carrier protein, and *Shigella flexneri* 2a rfb cluster produced bioconjugates (see the signals between molecular wheight markers 90-170 kDa, which correspond to *S. flexneri* 2a-EPA bioconjugate).

5 DETAILED DESCRIPTION

In one aspect, provided herein are methods for inserting contiguous sequences of DNA, including large, contiguous sequences of DNA, into host cell genomes. Such DNA sequences may comprise multiple components, e.g., genes, promoters, terminators, etc, and can be selectively inserted at desired positions in host cell genomes. In certain embodiments, the DNA sequences can be selectively inserted into regions of the host cell genome such that one or more components present in the fragments (e.g., genes) are expressed by the host cell, e.g., the host cell expresses one or more components (e.g., genes) that are not normally expressed by the host cell and/or the host cell expresses a component (e.g., a gene) that is naturally expressed by the host cell, but expresses more of such component. Methods of insertion of DNA are described in Section 5.1, below.

In a specific embodiment, provided herein is a method for inserting a large sequence of DNA into a host cell genome, wherein said large DNA sequence comprises one, two, three, four, five, or more genes. In certain embodiments, the genes present in the DNA sequences inserted into host cells in accordance with the methods described herein are under the control of one or multiple regulatory sequences or promoters that also are present in the DNA sequences. In certain embodiments, the DNA sequences inserted into host cells in accordance with the methods described herein may comprise additional elements essential to or beneficial to expression of the genes present in the large DNA sequence, e.g., enhancers, terminators.

In another specific embodiment, provided herein is a method for inserting a large sequence of DNA into a host cell genome, wherein said large DNA sequence comprises one or more operons, e.g., a cluster of genes under the control of a common regulatory signal or promoter.

In another specific embodiment, provided herein is a method for inserting a large sequence of DNA into a host cell genome, wherein said host cell genome further has a deletion of DNA that is normally associated with the host cell genome, i.e., the method results in both an insertion of heterologous DNA into the host cell genome and removal of normally present DNA from the host cell genome. In specific embodiments, the insertion of a large sequence of DNA is made at the site of the removal of a sequence of DNA from the host cell genome of the equivalent size, i.e., the DNA of the host cell genome is replaced by the inserted DNA sequence.

In certain embodiments, the methods described herein comprise the introduction of a helper plasmid and a donor plasmid into a host cell. As used herein, helper plasmids are meant to encompass plasmids that comprise elements (e.g., encode genes) that are required for the insertion of a large DNA sequence into the genome of a host cell. In accordance with the methods described herein, the helper plasmids do not incorporate any DNA into the host cell genome themselves, but rather facilitate the incorporation of insert DNA that is present in the donor plasmids described herein. Helper plasmids are described in greater detail in Section 5.1.1, below. As used herein, donor plasmids are meant to encompass plasmids that comprise the large DNA sequence to be inserted into a host cell genome, i.e., the donor plasmid "donates" part of itself to the host cell genome (i.e., the large DNA sequence to be inserted into the host cell genome is donated). In certain embodiments, the donor plasmids provided herein comprise other elements that are required or useful for insertion of the large DNA sequence into the host cell genome. Donor plasmids are described in greater detail in Section 5.1.2, below.

In another aspect, provided herein are host cells (e.g., prokaryotic host cells, e.g., *E. coli*) comprising genomes into which sequences of DNA, such as large sequences of DNA, have been inserted in accordance with a method described herein. Without being bound by theory, the methods described herein can be used to generate genetically stable host cells that are capable of producing proteins of interest, e.g., proteins for use as vaccines, glycosylated proteins, proteins for use in cosmetics, etc. As a result of the methods provided herein, such host cells need not be maintained and/or propagated in the presence of certain markers, e.g., antibiotic selection markers, due to the fact that the DNA comprising genes of interest are inserted directly into the genome of the host cells.

In certain embodiments, the host cells described herein comprise a genome into which one or more DNA sequences has been inserted, wherein said DNA sequences encode a protein or comprise an operon/gene cluster involved in the glycosylation of proteins, e.g., N-glycosylation of proteins. For example, in certain embodiments, a host cell described herein comprises a genome into which one or more of the following has been inserted: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase.

In a specific embodiment, a host cell provided herein comprises a genome into which a DNA sequence has been inserted, wherein the inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a second DNA sequence, wherein said second inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a fourth DNA sequence, wherein said fourth DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

In another specific embodiment, a host cell provided herein comprises a genome into which a DNA sequence has been inserted, wherein the inserted DNA sequence comprises two or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the genome of the host cell additionally has inserted into it a second DNA sequence, wherein said second inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

In another specific embodiment, provided herein is a host cell comprising a donor plasmid and a helper plasmid, (a) wherein the helper plasmid comprises: (i) under control of a first promoter, an open reading frame encoding lambda red recombinase; and (ii) under control of a second promoter, an open reading frame encoding a restriction endonuclease that has a recognition sequence that is not present in the host cell genome; and (b) wherein the donor plasmid comprises: (i) from 5' to 3': (1) the recognition sequence of the restriction endonuclease; (2) a first homology region of at least 0.5 kilobases (kb), (3) a heterologous insert DNA of at least 8 kb; and (4) a second homology region of at least 0.5 kb; and (ii) a counterselection marker. In a specific embodiment, the recognition sequence comprises at least 18 base pairs. In another specific embodiment, the restriction endonuclease is SceI. In a specific embodiment, the heterologous insert DNA comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

Nucleic acid sequences encoding oligosaccharyl transferases that can be inserted into the host cells described herein are known in the art. In a specific embodiment, the oligosaccharyl transferase nucleic acid sequence inserted into the genome of a host cell described herein is an oligosaccharyl transferase nucleic acid sequence derived from a prokaryotic organism. In another specific embodiment, the oligosaccharyl transferase nucleic acid sequence inserted into the genome of a host cell described herein is an oligosaccharyl transferase nucleic acid sequence from the genus *Campylobacter*. In another specific embodiment, the oligosaccharyl transferase nucleic acid sequence inserted into the genome of a host cell described herein is an oligosaccharyl transferase nucleic acid sequence from *Campylobacter jejuni* (e.g., the pglB gene from *C. jejuni*). In another specific embodiment, the oligosaccharyl transferase nucleic acid sequence inserted into the genome of a host cell described herein is an oligosaccharyl transferase nucleic acid sequence derived from a eukaryotic organism.

Nucleic acid sequences encoding glycosyltransferases that can be inserted into the host cells described herein are known in the art. In certain embodiments, the glycosyltransferase nucleic acid sequence inserted into a host cell described herein is the nucleic acid sequence of a glycosyltransferase described in International Patent Application Publication No. WO 2011/138361, the disclosure of which is incorporated by reference herein in its entirety. In a specific embodiment, the glycosyltransferase nucleic acid sequence inserted into the genome of a host cell described herein is derived from a Gram-positive bacterium, e.g., the glycosyltransferase nucleic acid sequence is derived from *S. aureus*. In another specific embodiment, the glycosyltransferase nucleic acid sequence inserted into the genome of a host cell described herein is the glycosyltransferase nucleic acid sequence of capsular polysaccharide 5 from *S. aureus*. In another specific embodiment, the glycosyltransferase nucleic acid sequence inserted into the genome of a host cell described herein is the glycosyltransferase nucleic acid sequence of capsular polysaccharide 8 from *S. aureus*. In another specific embodiment, the glycosyltransferase nucleic acid sequence inserted into the genome of a host cell described herein is derived from a Gram-negative bacterium, e.g., *E. coli*. In another specific embodiment, the glycosyltransferase nucleic acid sequence inserted into the genome of a host cell described herein is derived from a eukaryote.

Nucleic acid sequences encoding epimerases that can be inserted into the host cells described herein are known in the art. In certain embodiments, the epimerase nucleic acid sequence inserted into a host cell described herein is an epimerase nucleic acid sequence described in International Patent Application Publication No. WO 2011/062615, the disclosure of which is incorporated by reference herein in its entirety. In a specific embodiment, the epimerase nucleic acid sequence inserted into the genome of a host cell described herein is the epimerase nucleic acid sequence represented by the Z3206 gene of *E. coli* strain O157. See, e.g., WO 2011/062615 and Rush et al., 2009, The Journal of Biological Chemistry 285:1671-1680, which is incorporated by reference herein in its entirety.

Nucleic acid sequences comprising rfb gene clusters that can be inserted into the host cells described herein are known in the art. In a specific embodiment, the rfb gene cluster inserted into a host cell described herein is an rfb gene cluster from *E. coli*, e.g., an *E. coli* rfb cluster from any O serogroup/O antigen known in the art, e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, or O187, and subserotypes thereof. In another specific embodiment, the rfb gene cluster inserted into a host cell described herein is an rfb gene cluster from a *Pseudomonas* strain (e.g., a *P. aeruginosa* strain), a *Salmonella* strain (e.g., a *S. enterica* strain), a *Yersinia* strain, a *Klebsiella pneumoniae* strain, a *Francisella* strain (e.g., *F. tularensis*), an *Acinetobacter baumannii* strain, a *Burkholderia* strain, or a *Shigella* strain.

Nucleic acid sequences comprising capsular polysaccharide gene clusters that can be inserted into the host cells described herein are known in the art. In a specific embodiment, the capsular polysaccharide gene cluster inserted into a host cell described herein is a capsular polysaccharide gene cluster from an *E. coli* strain, a *Streptococcus* strain (e.g., *S. pneumoniae*, *S. pyrogenes*, *S. agalacticae*), a *Staphylococcus* strain (e.g. *S. aureus*), or a *Burkholderia* strain (e.g. *B mallei, B. pseudomallei, B. thailandensis*).

Nucleic acid sequences encoding carrier proteins that can be inserted into the host cells described herein are known in the art. The carrier proteins produced by the host cells described herein comprise at least one N-glycosylation consensus sequence, e.g., either the consensus sequence (i) Asn-X-Ser(Thr), wherein X is are independently selected from any amino acid except Pro; or (ii) D/E-X-N-Z-S/T, wherein X and Z are independently selected from any amino acid except Pro. Accordingly, the DNA sequences encoding carrier proteins inserted into the host cells described herein comprise at least one nucleic acid sequence within the carrier protein nucleic acid sequence that encodes an N-glycosylation consensus sequence. The DNA sequence encoding a carrier protein inserted into the host cells described herein can encode any carrier protein known in the art, including the carrier proteins described in Section 5.2.1.2, below. In a specific embodiment, the carrier protein nucleic acid sequence inserted into the genome of a host cell described herein is a nucleic acid sequence that encodes Exotoxin A of *P. aeruginosa* (EPA), including EPA that has been genetically modified to comprise at least one N-glycosylation consensus sequence. In another specific embodiment, the carrier protein nucleic acid sequence inserted into the genome of a host cell described herein is a nucleic acid sequence that encodes cholera toxin B. In another specific embodiment, the carrier protein nucleic acid sequence inserted into the genome of a host cell described herein is a nucleic acid sequence that encodes AcrA. In another specific embodiment, the carrier protein nucleic acid sequence inserted into the genome of a host cell described herein is a nucleic acid sequence that encodes HlA. In another specific embodiment, the carrier protein nucleic acid sequence inserted into the genome of a host cell described herein is a nucleic acid sequence that encodes ClfA.

In certain embodiments, the copy number of genes within the inserted DNA in a host cell described herein, e.g., heterologous insert DNA, is 1, 2, 3, 4, 5, 6, 7, 8, 9, or 10. In a specific embodiment, the copy number of genes within the inserted DNA in a host cell described herein, e.g., heterologous insert DNA is 1 or 2. In another specific embodiment, the copy number of genes within the inserted DNA in a host cell described herein, e.g., heterologous insert DNA is 1.

In certain embodiments, the host cells provided herein comprise a gene deletion, wherein a DNA sequence of interest has been inserted into the host cell genome at the site of the gene deletion. In a specific embodiment, a host cell provided herein is E. coli bearing a deletion of the waaL gene. In a specific embodiment, a DNA sequence encoding an oligosaccharyl transferase is inserted at the site of the waaL gene deletion in the E. coli host cell. In another specific embodiment, a host cell provided herein is E. coli bearing a deletion of the wecG gene. In a specific embodiment, a DNA sequence encoding a carrier protein is inserted at the site of the wecG gene deletion in the E. coli host cell. In another specific embodiment, a host cell provided herein is E. coli bearing a deletion of the waaL gene and a deletion of the wecG gene, wherein an oligosaccharyl transferase is inserted into the E. coli host cell at the site of the deleted waaL gene and wherein a carrier protein (e.g., EPA comprising an N-glycosylation consensus sequence) is inserted into the E. coli host cell at the site of the deleted wecG gene.

5.1 Methods of DNA Insertion

Described in this section (5.1) are novel methods of inserting DNA sequences, including large sequences of DNA (i.e., heterologous insert DNA), into the genome of host cells. Those skilled in the art will appreciate that the methods described in this section possess several advantages and allow for the generation of host cells (e.g., prokaryotic host cells) that can be used for the biological production of commercial goods, including vaccines. Exemplary advantages that the genetically stable host cells generated in accordance with the methods described herein possess include, without limitation, (i) selection pressure is unnecessary for chromosomally inserted DNA, (ii) the copy number of genes within the heterologous insert DNA is strictly regulated, and (iii) the heterologous insert DNA in the host cell genomes remains stable over multiple generations of host cell propagation. Such stable host cells are useful for, e.g., industrial fermentation.

In certain embodiments, sequences of DNA, e.g., large contiguous sequences of DNA are introduced into a host cell (e.g., E. coli) using the methods described herein (see below). In certain embodiments, sequences of DNA are introduced into a host cell (e.g., E. coli) using one or more methods described in Section 5.1.6, below. Those of skill in the art will readily appreciate that the methods of this invention can be practiced by modifying various components used in the methods. For example, the donor plasmids and helper plasmids described herein may comprise multiple different elements, so long as they remain functional in the methods described herein. Exemplary modifications to the donor plasmids described herein, the helper plasmids described herein, and the host cells described herein are presented in Sections 5.1.1 et seq.

In an exemplary embodiment, a method of inserting a large sequence of DNA (i.e., heterologous insert DNA) into the genome of a host cell comprises the use of (i) a donor plasmid comprising (a) heterologous insert DNA flanked by homology regions (HR), e.g., long homology regions (e.g., HR of any appropriate size, e.g., from 0.4-2.0 kb), which direct the site of recombination in the host cell genome (use of such HR increases efficiency of insertion), and (b) a counter selection marker that represses growth of host cells that comprise the donor plasmid, i.e., the non-integrated donor plasmid following introduction of the donor plasmid into the host cell (use of the counter selection marker eliminates false positive clones [11]); and (ii) a helper plasmid comprising an open reading frame encoding lambda red recombinase and an open reading frame encoding a restriction endonuclease that has a recognition sequence that is not present in the host cell genome (e.g., SceI restriction endonuclease). In the helper plasmid, the open reading frame encoding lambda red recombinase and the open reading frame encoding a restriction endonuclease that has a recognition sequence that is not present in the host cell genome (e.g., SceI restriction endonuclease) may be under control of different promoters (e.g., a first promoter and second promoter) for concerted expression of the proteins produced by the open reading frames [12]. The donor plasmid may also comprise the recognition sequence of the restriction endonuclease present in the helper plasmid.

The methods described herein allow for multiple rounds of insertions one after another, i.e. that first a large DNA insert can be inserted at one position, and afterwards more insertions can be performed using the same methodology. These consecutive insertions may be targeted to any part of the host cell genome, i.e. also to the previously inserted DNA or the original, chromosomal sequences present in the host cell. In addition, the method is compatible with other insertion methods, like homologous recombination according to Datsenko and Wanner (Datsenko K A, Wanner B L: One-step inactivation of chromosomal genes in *Escherichia coli* K-12 using PCR products. *Proc Natl Acad Sci USA* 2000, 97(12):6640-6645.). The insertion step of the methods described herein, i.e., the step of the heterologous insert DNA being inserted into the genome of a host cell, is based on the homologous recombination—or cross over—of homologous DNA stretches in vivo. During homologous recombination, one homolog of the DNA must be in the target site, and one in the donor construct (i.e. the donor plasmid). In accordance with the methods described herein, elements required for insertion may be introduced into the host cell, e.g., introduced on one or more plasmids that are introduced into the host cell. Those of skill in the art will readily appreciate how plasmids can be introduced into host cells, and exemplary methods of doing so are provided in Section 5.1.3, below.

The methods by which heterologous insert DNA can be inserted into the genome of a host cell may comprise multiple steps. For example, donor plasmids and/or helper plasmids may need to be engineered before the method can be performed. Further, modifications to host cells may be performed before or during the method of insertion. Those of skill in the art will readily understand what steps need to be performed based on the heterologous insert DNA that is desired to be inserted into a given host cell. Generally, the methods of insertion of heterologous insert DNA into a host cell described herein may comprise some or all of following steps:

(1) A donor plasmid is made. A desired heterologous insert DNA sequence (i.e., a heterologous insert DNA sequence that comprises one or more genes of interest) is cloned into a cloning site (e.g., a multiple cloning site, abbreviated as MCS) of a plasmid suitable for use as a donor plasmid (see Section 5.1.2). DNA sequences suitable for use as homology regions (i.e., DNA sequences homologous to the insertion location on the host cell genome) also are cloned into the donor plasmid, such that the homology regions flank the heterologous insert DNA. These methods of cloning and assembly of the donor plasmid can be done according to any established and well known technology to modify and synthesize DNA such as, without limitation, molecular cloning using restriction enzymes and ligase, transposases, chemical synthesis, etc. which technologies are known to those of skill in the art [1].

In addition, in certain embodiments, a selection cassette comprising an open reading frame encoding a protein that confers antibiotic resistance is positioned in between the homology arms. Host cells comprising the heterologous insert DNA inserted into their genome can be identified by culturing them on media that comprises the antibiotic to which the antibiotic resistance gene of the selection cassette provides resistance. In certain embodiments, the selection cassette may be flanked by FRT sites [13], which allow for later removal of the cassette by site directed recombination. Incorporating FRT sites in this manner into the donor plasmid thus ensures that the selection cassette does not remain integrated in the host cell genome. In another embodiment, the selection cassette can be removed following integration via dif site mediated site directed homologous recombination [14] or by other, site directed chromosomal mutagenesis technologies.

The donor plasmids described herein also are engineered to comprise an open reading frame encoding a counterselection protein. Any gene encoding a protein known to those of skill in the art suitable for use in counterselection approaches can be incorporated into the donor plasmids described herein. In a specific embodiment, the sacB gene is used for counterselection.

The donor plasmids described herein also are engineered to comprise an origin of replication. Those of skill in the art will readily appreciate that the origin of replication incorporated into the donor plasmid should be suitable for use in the host cell that is undergoing genome modification. For example, an *E. coli* replication origin must be present when cloning is being performed in *E. coli*. In a specific embodiment, the origin of replication is oriT. Those of skill in the art will readily appreciate that shuttle plasmids (i.e., plasmids capable of replication in multiple host cells, e.g., multiple bacterial species) can be generated using methods known in the art, and such plasmids could be used for insertion into numerous types of host cells, e.g., prokaryotic cells, archeal cells, eubacterial cells, or eukaryotic cells. Such shuttle plasmids may comprise organism specific expression control elements and replication origins.

(2) A helper plasmid is made. The helper plasmid is engineered to encode all necessary activities for mediating DNA insertion into host cells as described herein and for maintenance of the helper plasmid within the host cells that undergo recombination. In certain embodiments, the helper plasmids described herein comprise (i) a selection cassette for plasmid maintenance in the host cell, (ii) a regulon for the expression of a recombinase, i.e. an enzyme or enzymes that support and enhance the crossing over efficiency between homologous DNA stretches, (iii) a regulon for expression of a function that linearizes the DNA insert resulting in terminal homologous sequences which can undergo homologous recombination, (iv) a regulon expressing a RecA homolog for host cells that do not have an own recA copy and (v) a conditional origin of replication. These elements are described below in more detail.

In certain embodiments, the helper plasmids used in accordance with the methods described herein comprise components similar to the helper plasmid pTKRED (Gene bank GU327533.1; [12]). In a specific embodiment, the helper plasmid pTKRED (Gene bank GU327533.1; [12]) is used in the methods described herein.

(3) The donor plasmid and the helper plasmid are introduced into the same host cell. Insertion of donor and helper plasmids can be performed by many different technologies known to those of skill in the art including, without limitation, electroporation, use of chemically competent cells, heat shock, and phage transduction. The host cells can then be cultured under selective conditions to enrich for cells carrying the introduced plasmids.

(4) The insertion procedure is initiated. An exemplary insertion procedure comprises the following steps: overnight cultures of positive clones (i.e. host cells comprising both the helper and donor plasmids) can be grown at, e.g., 30° C. in media comprising the proper antibiotics for selection (such antibiotics can readily be selected by those of skill in the art based on the selection cassettes present in the donor/helper plasmids). The cultures then can be diluted and grown at, e.g., 30° C. until exponential phase in the presence of appropriate antibiotics. Under these conditions, the helper and donor plasmids are maintained but silent. Next, the media is replaced by media containing the antibiotics for selection, as well as any inducers of conditional elements (e.g., inducible promoters or conditional origins of replication) present in the plasmids, followed by further incubation of the cells. During this time, the restriction endonuclease (e.g., SceI) in the helper plasmid and the recombinase (e.g., lambda red recombinase) in the helper plasmid are expressed, leading to cleavage of the donor plasmid at the homology arms, and homologous recombination of the homology DNA at the homologous sites in the genome of the host cell (see FIG. 2). Next, the cells are plated on medium containing the component that the counterselection marker of the donor plasmid corresponds to (e.g., sucrose if the counterselection marker is sacB). This step results in counterselection of cells that comprise the donor plasmid, i.e., cells that the donor plasmid exists in an uninserted state. Such medium also comprises the resistance marker present in the insertion cassette of the donor plasmid (i.e., the antibiotic resistance cassette that is present between the HR of the donor plasmid, to select for cells that contain the heterologous insert DNA. After overnight incubation, the cells are then screened for recombined clones showing an antibiotic resistance phenotype consistent with (i) loss of the helper and donor plasmids and (ii) presence of the heterologous DNA insert.

Those of skill in the art will appreciate that the foregoing conditions can be modified using standard experimental approaches. For example, certain conditions can be changed based on the specific host cells used, the selection and counterselection markers used, etc. Exemplary insertion strains are presented in Tables 1 and 2.

Figure 2:
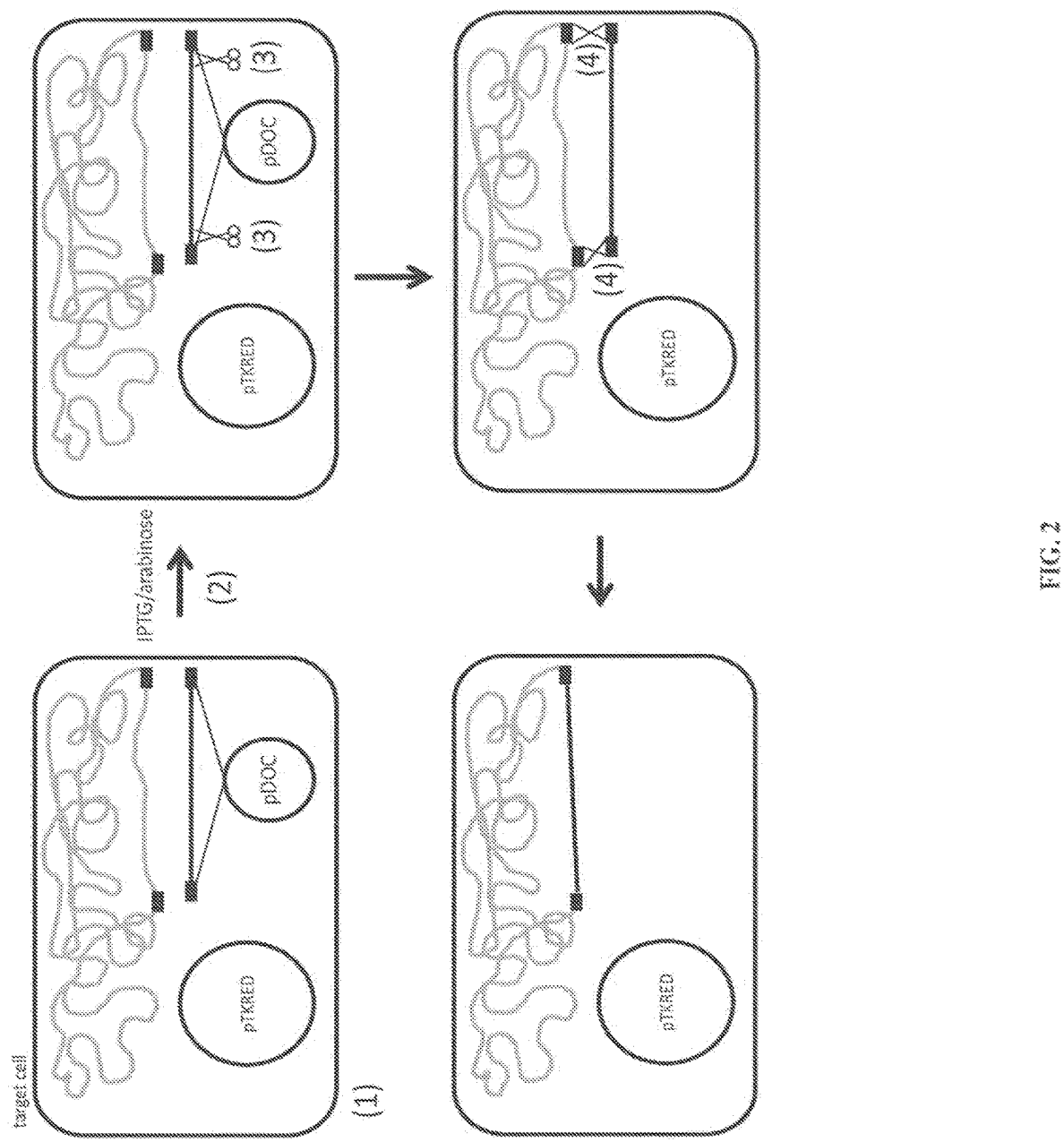

In a specific embodiment, a method of inserting DNA into a host cell comprises the following: Overnight cultures of positive clones (i.e. containing helper and donor plasmid) are grown at 30° C. in liquid LB media containing antibiotics for selection (spec and one or both selectable markers of the donor plasmid), diluted to OD600 of 0.05 and grown at 30° C. until exponential phase in the presence of spectinomycin and the DNA insert selection marker (kanR or clmR). Under these conditions, helper and donor are maintained but silent. Then, the media is replaced by LB media containing the antibiotics for selection, 0.2% arabinose, and 1 mM IPTG, and cells are further incubated at 30° C. for several hours (2, 4, 6, 8 h). During this time, the SceI and the Red recombinase proteins are expressed, leading to cleavage of the donor plasmid at the homology arms, and to homologous recombination of the homology DNA at the homologous sites in the genome (FIG. 2). Then, the cells are plated on LB medium containing 10% sucrose (to counter select for cells that contain the donor plasmid), and the resistance marker present in the insertion cassette (kanR or clmR), to select for the cells that still contain the DNA insert. Other selection and counter selection markers may require the adjustment of the conditions. After overnight incubation at 37-42° C., the cells are screened for recombined clones showing an antibiotic resistance phenotype consistent with i) loss of the helper and ii) donor plasmids and iii) presence of DNA insert. Clones are replica plated on LM supplemented with amp, spec, and kan or clm to screen for sensitive colonies. The combined phenotypes indicating candidate bacterial colonies possibly containing the DNA insert are: Sensitivity to ampicillin (indicative of loss of the donor plasmid); Spectinomycin sensitivity (indicative of loss of the helper plasmid); Clm or kan resistance (indicative of presence of DNA insert).

As demonstrated in the working Examples below, the foregoing methods were used to insert heterologous DNA sequences comprising O antigen and capsular polysaccharide clusters into specific locations of the *E. coli* genome, while simultaneously removing naturally and preexisting O antigen and capsular clusters from the *E. coli* genome in the process. The resultant host cells were used to produce glycoproteins consisting of a carrier protein expressed in the periplasmic space of said host cells that contained covalently linked O antigen polysaccharides at specific sites. Those of skill in the art will readily appreciate that such methods could be applied to insert any desired heterologous DNA sequence into host cells.

5.1.1 Helper Plasmids

The helper plasmids described herein and used in accordance with the methods described herein encode all necessary components for mediating DNA insertion and for maintenance of the helper plasmid within host cells that undergo recombination for the necessary period of time, i.e., the host cells into which heterologous DNA is inserted by the methods described herein. Following are certain components that can be introduced into the helper plasmids described herein.

5.1.1.1 Selectable Markers

Selectable markers are introduced into the helper plasmids described herein to ensure proper introduction of the helper plasmids into the host cells modified as described herein. In particular, selectable markers can be used to select for host cells that have accepted the plasmid after transformation, and to maintain the plasmid during the recombination procedure. Numerous systems for selection are known in the art and available to those of skill in the art. Examples include, without limitation, gene cassettes that confer (i) resistance to antibiotics (e.g., amp, kan, spec, clm, gen, tmp, tet) [15]; (ii) growth on selective media, e.g., auxotrophic marker systems (Regis Sodoyer, Virginie Courtois, Isabelle Peubez and Charlotte Mignon (2012). Antibiotic-Free Selection for Bio-Production: Moving Towards a New "Gold Standard", Antibiotic Resistant Bacteria—A Continuous Challenge in the New Millennium, Marina Pana (Ed.), ISBN: 978-953-51-0472-8, InTech, Available from: http://www.intechopen.com/books/antibiotic-resistant-bacteria-a-continuous-challenge-in-the-new-millennium/antibiotic-free-selection-for-bio-production-moving-towards-a-new-gold-standard), (iii) toxin-antitoxin systems, and (iv) resistance to biocides like e.g. triclosan [16]. Table 6, below, also provides a list of antibiotics that can be used for selection.

In a specific embodiment, a spectinomycin resistance cassette is used for helper plasmid selection, i.e. for maintaining the helper plasmid in the target cell.

5.1.1.2 Recombinase Enzymes

The helper plasmids described herein comprise recombinases to support the crossing over (homologous recombination) and re-ligation of homologous parts of DNA. Exemplary recombinases that can be used in accordance with the methods described herein include, without limitation, lambda red recombinase, RecE/RecT from Rac prophage [17], and RedαβΔ from bacteriophage lambda [18-20].

In a specific embodiment, the recombinase used in the helper plasmids described herein is lambda red recombinase. In another specific embodiment, the lambda red recombinase is under control of the lac promoter. Lambda red recombinase catalyzes the homologous recombination reaction (crossing over) and consists of three functional subunits that are encoded in three open reading frames on the plasmid. The first gene is gam, which is a member of the Host-nuclease inhibitor protein Gam family. The Gam protein inhibits RecBCD nuclease and is found in both bacteria and bacteriophage. The second gene is beta and encodes a protein of the RecT family. RecT proteins are DNA single-strand annealing proteins (SSAPs), such as RecT, Red-beta, ERF and Rad52, and function in RecA-dependent and RecA-independent DNA recombination pathways. The third gene is the exo gene, which encodes an YqaJ-like viral recombinase domain protein. This protein family is found in many different bacterial species but is of viral origin. The protein forms an oligomer and functions as a processive alkaline exonuclease that digests linear double-stranded DNA in a Mg(2+)-dependent reaction. It has a preference for 5'-phosphorylated DNA ends. The three proteins promote homologous recombination events in *E. coli* and other organsims.

In certain embodiments, recombinases present on the helper plasmid are under control of promoters other than the lac promoter. Such other promoters may include, without limitation, the araBAD promoter [21], the rhamnose promoter [22], heat inducible promoters [23], the salicylate promoter [24], the tetracycline promoter [25], etc.

5.1.1.3 Endonucleases

Endonucleases on the helper plasmid linearize the donor plasmid and thereby mobilize the insertion piece of DNA. Accordingly the donor plasmids used in a given method described herein possess the recognition sequence of the restriction endonuclease present on the helper plasmid. Homologous recombination by recombinase enzymes is dependent on single stranded DNA insert ends as substrates for pairing with the target site. Thus, linearization (i.e. generating double strand ends) is an important step for activation of the DNA insert. Open double strand DNA ends are enzymatically digested to single strands which then are the actual substrates for the pairing and recombination.

The endonucleases used herein may act in the cytoplasm of the host cells, thus they may cut the donor plasmid, but should not affect host cell chromosome stability. Generally, any restriction enzyme or DNA double strand cutter can be used in the methods described herein as long as it does not cut the host cell genomic DNA. In specific embodiments, endonucleases which work in the cytoplasm and target long and rare recognition sites can be used, as such endonucleases are highly site specific by having rare recognition sequences. For example, endonucleases that have recognition sequences of greater than 15, 16, 17, 18, 19, 20, 21, 22, 23, 24, 25, 26, 27 28, 29, or 30 base pair recognition sites can be selected for use in the methods described herein.

In a specific embodiment, homing endonucleases are used in the methods described herein. The homing endonucleases are a special type of restriction enzymes encoded by introns or inteins. They comprise different structural groups, e.g. the LAGLIDADG (SEQ ID NO: 1), GIY-YIG (SEQ ID NO: 2), H-N-H, and His-Cys box families. An exemplary list of homing endonucleases is given in Table 4, below. The endonucleases used herein can be present on the helper plasmid such that they are under the control of an inducible promoter also present on the helper plasmid.

In a specific embodiment, the endonuclease encoded by the helper plasmids described herein is SceI. SceI is a member of the LAGLIDADG (SEQ ID NO: 1) DNA endonuclease family. This is a family of site-specific DNA endonucleases encoded by DNA mobile elements. Functionally, SceI is a homing restriction endonuclease that cuts an 18-base pair recognition sequence TAGGGA-TAACAGGGTAAT (SEQ ID NO: 3), that never occurs in the *E. coli* genome. The specific, rare and long recognition sequence is crucial for its application in for the invention. In certain embodiments, the SceI is under the control of an inducible promoter, e.g., the arabinose promoter.

5.1.1.4 RecA

RecA is a bacterial enzyme which has roles in homologous recombination, DNA repair, and the induction of the SOS response. RecA couples ATP hydrolysis to DNA strand exchange, i.e. it is catalyzing the actual recombination reaction. For the purpose of recombination as described herein, recA activity must be present in the host cell. However, in most cases the copy present in wild type host cell genome is sufficient for recombination to take place. Thus, recA need not be introduced into host cells which endogenously express recA.

In host cells that do not express recA, recA can be introduced into the host cell on the helper plasmid. RecA homologs are present in almost every organism. Accordingly, those of skill in the art will appreciate that any recA functional gene could be used in accordance with the methods described herein, i.e., either used based on its natural presence in the host cell or used by introducing recA function into host cells, e.g., host cells that do not naturally comprise recA.

5.1.1.5 Conditional Origins of Replication

An origin of replication is required for DNA replication of the helper plasmid and for distribution of plasmid copies to daughter cells during cell division. Conditional origins of replication can be used to enhance or reduce plasmid copy numbers in cells. For example, a temperature sensitive origin of replication can be used in the methods described herein. Such an origin of replication is non-functional at temperatures above 37° C., resulting in plasmid loss. Other conditional origins of replication are known in the art and can be used with the methods described herein [26]. An exemplary list of conditional origins of replication is provided in Table 5.

In a specific embodiment, the origin of replication used herein is a temperature sensitive pSC101 origin of replication [27], which leads to the loss of the plasmid upon growth at high temperatures. Other origins of replication that can be used include those from pMB1, ColE1, R100, IncW, and others (see for example [28]).

5.1.1.6 Inducible Promoters and Inducers

The ability to control helper plasmid function is important to reduce recombination activity to a limited time during cell growth, as unwanted side reactions may occur if continuous recombination is promoted. Thus, inducible promoters and inducers may be utilized to ensure that certain components of the helper plasmids are expressed only when desired. Exemplary inducible promoters include, without limitation, the araBAD promoter system (inducible by the presence of arabinose) and the tac promoter (inducible by the presence of IPTG). Table 7 provides a further list of inducible components that can be used in accordance with the methods described herein.

5.1.2 Donor Plasmids

The donor plasmids described herein "donate" a desired heterologous insert DNA sequence to a host cell, resulting in host cells that have stably integrated the heterologous insert DNA.

In a specific embodiment, the donor plasmid used in the methods described herein is based on the plasmid pDOC-C (Gene bank GQ889494.1; [11]). pDOC-C is a derivative of pEXT100T [29]. The plasmid contains an ampicillin resistance gene for selection (ampR), an origin for replication (oriT), and the sacB gene. SacB is a secreted protein of the levansucrase operon originating from *Bacillus subtilis*. In the presence of sucrose, sacB confers lethality. Thus, by simply adding sucrose to the medium, sacB can be used as a system to counter select against cells carrying the plasmid [30]. Furthermore, pDOC-C encodes a multiple cloning site which is flanked by SceI sites for in vivo linearization.

Following are certain components that can be introduced into the helper plasmids described herein.

5.1.2.1 Selectable Markers

The selectable markers present on the donor plasmids described herein may be selected from the same lists as provided in Section 5.1.1.1, above, as well as those listed in Table 6, below. Other selection systems also may be used, e.g., selection systems based on auxotrophic markers would be useful for the selection for insertion events. When an acceptor strain contains a deletion in a gene that makes the strain auxotrophic (i.e. its growth is dependent on a certain media component), this gene could be included in the DNA insert.

In a specific embodiment, the donor plasmid comprises a clmR and/or kanR cassette.

5.1.2.2 Heterologous Insert DNA

Those of skill in the art will readily appreciate that any gene, or combination of genes, can be included in heterologous insert DNA and subsequently inserted into host cell genomes using the methods described herein.

In a specific embodiment, the heterologous insert DNA inserted into the host cells described herein comprises a gene cluster. In a specific embodiment, the gene cluster is one that encodes capsular polysaccharide. In another specific embodiment, the gene cluster is one that encodes O antigen. Host cells comprising such inserted gene clusters can be used, e.g., to synthesize recombinant glycoproteins production that can be used as vaccines.

Those of skill in the art will appreciate that the instant invention allows for the stable insertion of large sequences of DNA into the genomes of host cells. For example, the DNA sequences may comprise 1 kb up to 40 kb. In certain embodiments, the heterologous insert DNA is greater than 8 kb, 9 kb, 10 kb, 11 kb, 12 kb, 13 kb, 14 kb, 15 kb, 16 kb, 17 kb, 18 kb, 19 kb, or 20 kb. In certain embodiments, the heterologous insert DNA is greater than 25 kb. In certain embodiments, the heterologous insert DNA is greater than 30 kb. In certain embodiments, the heterologous insert DNA is greater than 35 kb. In certain embodiments, the heterologous insert DNA is greater than 40 kb.

In one embodiment, the methods described herein are used to insert a DNA sequence comprising an rfb cluster of an *E. coli* strain into a host cell. The inserted rfb cluster may belong to any O serogroup/O antigen known in the art, e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, or O187, and subserotypes thereof. In a specific embodiment, the host cell is a prokaryotic host cell. In another specific embodiment, the host cell is *E. coli*.

In another embodiment, the methods described herein are used to insert a DNA sequence comprising an rfb cluster of a *Pseudomonas* strain into a host cell. In a specific embodiment, the *Pseudomonas* strain is a *P. aeruginosa* strain. In a specific embodiment, the host cell is a prokaryotic host cell. In another specific embodiment, the host cell is *E. coli*.

In another embodiment, the methods described herein are used to insert a DNA sequence comprising an rfb cluster of a *Salmonella* strain into a host cell. In a specific embodiment, the *Salmonella* strain is an *S. enterica* strain. In a specific embodiment, the host cell is a prokaryotic host cell. In another specific embodiment, the host cell is *E. coli*.

In another embodiment, the methods described herein are used to insert a DNA sequence comprising an rfb cluster of a *Yersinia* strain into a host cell. In a specific embodiment, the host cell is a prokaryotic host cell. In another specific embodiment, the host cell is *E. coli*.

In another embodiment, the methods described herein are used to insert a DNA sequence comprising an rfb cluster of a *Klebsiella pneumoniae* strain into a host cell. In a specific embodiment, the host cell is a prokaryotic host cell. In another specific embodiment, the host cell is *E. coli*.

In another embodiment, the methods described herein are used to insert a DNA sequence comprising an rfb cluster of a *Francisella tularensis* strain into a host cell. In a specific embodiment, the host cell is a prokaryotic host cell. In another specific embodiment, the host cell is *E. coli*.

In another embodiment, the methods described herein are used to insert a DNA sequence comprising an rfb cluster of an *Acinetobacter baumannii* strain into a host cell. In a specific embodiment, the host cell is a prokaryotic host cell. In another specific embodiment, the host cell is *E. coli*.

In another embodiment, the methods described herein are used to insert a DNA sequence comprising an rfb cluster of a *Burkholderia* strains into a host cell. In a specific embodiment, the host cell is a prokaryotic host cell. In another specific embodiment, the host cell is *E. coli*.

In another embodiment, the methods described herein are used to insert a DNA sequence comprising an rfb cluster of a *Shigella* strain into a host cell. In a specific embodiment, the host cell is a prokaryotic host cell. In another specific embodiment, the host cell is *E. coli*.

In another embodiment, the methods described herein are used to insert a DNA sequence comprising a capsular polysaccharide gene cluster of an organism into a host cell. In a specific embodiment, the organism is an *E. coli* strain. In another specific embodiment, the organism is a *Streptococcus* strain (e.g., *S. pneumoniae, S. pyrogenes, S. agalacticae*), a *Staphylococcus* strain (e.g. *S. aureus*), a *Burkholderia* strain (e.g. *B mallei, B. pseudomallei, B. thailandensis*). In a specific embodiment, the host cell is a prokaryotic host cell. In another specific embodiment, the host cell is *E. coli*.

In another embodiment, the methods described herein are used to insert a DNA sequence comprising one or more enzymes that synthesize oligo- or polysaccharides on the undecaprenylpyrophosphate.

In certain embodiments, the host cells are optimized by introducing into said host cells genetic elements that are encoded outside of an rfb cluster. For example, genes encoding glycosyltransferases and acetyltransferases that are found outside of rfb clusters and capsular polysaccharide clusters and that modify recombinant polysaccharides can be introduced into the host cells. As another example, in *E. coli* and *Shigella* O antigens, there are glucosyltransferases encoded in prophage gene clusters [31, 32]. These gene clusters are called gtr and are organized in an operon consisting of a glucosyltransferase that adds a single glucose residue to undecaprenol-phosphate (GtrA), GtrB which flips the glucose-phosphate bound undecaprenol to the periplasmic face of the membrane, and the specific Gtr transferase, which then transfers the undecaprenyl-phosphate bound glucose to the growing O antigen chain. DNA comprising such genes can be introduced into the host cells described herein.

A similar modification is acetylation. Acetylation of O antigens is common in *Shigella*, and to a lesser extent in *E. coli*. The modification is catalyzed by a single acetyl transferase which is encoded sometimes within (*E. coli* O16), but also outside of the rfb cluster (*S. flexneri* 3a) [33]. DNA encoding such acetyl transferases can be introduced into the host cells described herein.

The branching and modification of O antigens is often important for an efficient and specific immune response to polysaccharides. Thus these modification pathways can be included in inserted production strains to produce conjugates that contain all possible epitopes found in nature.

A further embodiment of the invention is the insertion of expression cassettes for recombinant protein production that is controlled by an inducible promoter system. This means that large DNA stretches that not only contain the expression cassette but also expression constructs for regulatory proteins, are a reasonable target for the presented technology.

Other DNA sequences that can be inserted into host cells in accordance with the methods described herein include, without limitation, DNA comprising/encoding oligosaccharyltransferases and glycosyltransferases derived from known sources, e.g., prokaryotic oligosaccharyltransferases and glycosyltransferases and/or eukaryotic oligosaccharyltransferases and glycosyltransferases; DNA comprising/encoding epimerases; and DNA comprising/encoding carrier proteins.

Nucleic acid sequences encoding oligosaccharyl transferases that can be inserted into the host cells described herein are known in the art. In a specific embodiment, the oligosaccharyl transferase nucleic acid sequence inserted into the genome of a host cell described herein is an oligosaccharyl transferase nucleic acid sequence derived from a prokaryotic organism. In another specific embodiment, the oligosaccharyl transferase nucleic acid sequence inserted into the genome of a host cell described herein is an oligosaccharyl transferase nucleic acid sequence from the genus *Campylobacter*. In another specific embodiment, the oligosaccharyl transferase nucleic acid sequence inserted into the genome of a host cell described herein is an oligosaccharyl transferase nucleic acid sequence from *Campylobacter jejuni* (e.g., the pglB gene from *C. jejuni*). In another specific embodiment, the oligosaccharyl transferase nucleic acid sequence inserted into the genome of a host cell described herein is an oligosaccharyl transferase nucleic acid sequence derived from a eukaryotic organism.

Nucleic acid sequences encoding glycosyltransferases that can be inserted into the host cells described herein are known in the art. In certain embodiments, the glycosyltransferase nucleic acid sequence inserted into a host cell described herein is the nucleic acid sequence of a glycosyltransferase described in International Patent Application Publication No. WO 2011/138361, the disclosure of which is incorporated by reference herein in its entirety. In a specific embodiment, the glycosyltransferase nucleic acid sequence inserted into the genome of a host cell described herein is derived from a Gram-positive bacterium, e.g., the glycosyltransferase nucleic acid sequence is derived from *S. aureus*. In another specific embodiment, the glycosyltransferase nucleic acid sequence inserted into the genome of a host cell described herein is the glycosyltransferase nucleic acid sequence of capsular polysaccharide 5 from *S. aureus*. In another specific embodiment, the glycosyltransferase nucleic acid sequence inserted into the genome of a host cell described herein is the glycosyltransferase nucleic acid sequence of capsular polysaccharide 8 from *S. aureus*. In another specific embodiment, the glycosyltransferase nucleic acid sequence inserted into the genome of a host cell described herein is derived from a Gram-negative bacterium, e.g., *E. coli*. In another specific embodiment, the glycosyltransferase nucleic acid sequence inserted into the genome of a host cell described herein is derived from a eukaryote.

Nucleic acid sequences encoding epimerases that can be inserted into the host cells described herein are known in the art. In certain embodiments, the epimerase nucleic acid sequence inserted into a host cell described herein is an epimerase nucleic acid sequence described in International Patent Application Publication No. WO 2011/062615, the disclosure of which is incorporated by reference herein in its entirety. In a specific embodiment, the epimerase nucleic acid sequence inserted into the genome of a host cell described herein is the epimerase nucleic acid sequence represented by the Z3206 gene of *E. coli* strain 0157. See, e.g., WO 2011/062615 and Rush et al., 2009, The Journal of Biological Chemistry 285:1671-1680, which is incorporated by reference herein in its entirety.

Nucleic acid sequences encoding carrier proteins that can be inserted into the host cells described herein are known in the art. The carrier proteins produced by the host cells described herein comprise at least one N-glycosylation consensus sequence, e.g., either the consensus sequence (i) Asn-X-Ser(Thr), wherein X is are independently selected from any amino acid except Pro; or (ii) D/E-X-N-Z-S/T, wherein X and Z are independently selected from any amino acid except Pro. Accordingly, the DNA sequences encoding carrier proteins inserted into the host cells described herein comprise at least one nucleic acid sequence within the carrier protein nucleic acid sequence that encodes an N-glycosylation consensus sequence. The DNA sequence encoding a carrier protein inserted into the host cells described herein can encode any carrier protein known in the art, including the carrier proteins described in Section 5.2.1.2, below. In a specific embodiment, the carrier protein nucleic acid sequence inserted into the genome of a host cell described herein is a nucleic acid sequence that encodes Exotoxin A of *P. aeruginosa* (EPA), including EPA that has been genetically modified to comprise at least one N-glycosylation consensus sequence. In another specific embodiment, the carrier protein nucleic acid sequence inserted into the genome of a host cell described herein is a nucleic acid sequence that encodes cholera toxin B. In another specific embodiment, the carrier protein nucleic acid sequence inserted into the genome of a host cell described herein is a nucleic acid sequence that encodes AcrA. In another specific embodiment, the carrier protein nucleic acid sequence inserted into the genome of a host cell described herein is a nucleic acid sequence that encodes HlA. In another specific embodiment, the carrier protein nucleic acid sequence inserted into the genome of a host cell described herein is a nucleic acid sequence that encodes ClfA.

(a) Selection of Regions of Homology

The lengths of the homologous region (HR) for use in accordance with the methods described herein can be determined experimentally. Generally, HR may have a length ranging from about 0.1 kb and 3.0 kb, or greater. In certain embodiments, the HR are from 0.1 kb to 0.5 kb, from 0.5 kb to 1 kb, from 1 kb to 3 kb, from 3 kb to 5 kb, from 5 kb to 10 kb, from 10 kb to 15 kb, from 15 kb to 20 kb, or greater than 20 kb. In certain embodiments, the HR are of identical length or are comparable in length. In certain embodiments, the HR are not of identical length or are not comparable in length.

The distance between HR also can be determined by experimentation. The distance between HR may range from 0.1 kb to 12 kb, or greater, and can be determined by the length of the heterologous insert DNA and/or the stretch of DNA in the host cell genome to be deleted (e.g., long stretches of the host cell genome can be deleted as long as they do not comprise a gene essential to the survival of the host cell). The location of the heterologous DNA insertion is defined by the sequence of the HR. Thus, insertion can be performed at virtually any position in the genome of a host cell (e.g., at any position on any chromosome of a host cell). In certain embodiments, the methods described herein can be used to clone large DNA pieces into plasmids present in the target cells, so long as the HR of the donor plasmid are present on the target plasmid that is present in the host cell, e.g., rather than in the target chromosome.

Figure 1:
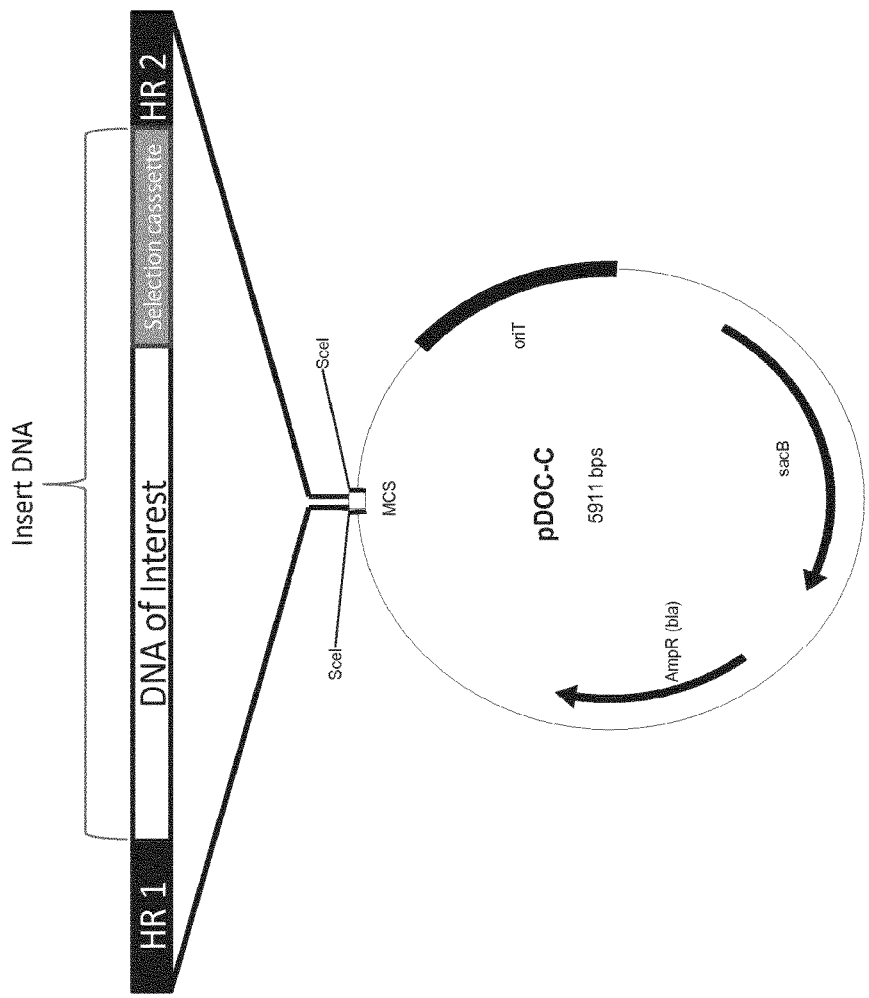

An important aspect of the methods described herein is that the DNA insert is inserted in a genomic location which is chosen by selecting the homologous recombination regions accordingly (HR1 and HR2, see FIG. 1). HR1 and HR2 flank the DNA insert on the donor plasmid, and they also flank the DNA which is replaced by the DNA insert after insertion. In the working examples provided below, HRs were chosen which are located 3 (replacement of wecA-wzzE) or 12 kb (replacement of rfb cluster) apart from each other in the target chromosome, and successful insertion was observed.

Insertion locations may be chosen multiple ways including, without limitation: I) a region of insertion may be selected because it is desirable to remove a possibly competing or interfering pathway by replacing it with the desired one (see the Examples, below); II) Insertion may be chosen at the position where the target cell naturally contains a similar cluster. Expression level and location may then be balanced for optimal expression; III) An insertion location may be unrelated to the DNA being inserted and can be entirely empirically chosen for the expression level the recombinant DNA insert shows at a specific position. i.e., multiple different random insertions could be made and the best producing strain be chosen; and IV) An insertion can delete an undesired function, or delete a function that can be used for selection of recombinant proteins.

(b) Deletion of DNA at Site of Insert

In certain embodiments, the methods described herein result in deletion of host cell DNA, e.g. deletion of genomic DNA that encodes one or more genes that may interfere with the desired result of the inserted DNA. In certain embodiments, the host cell genomic DNA to be removed is directly replaced with heterologous insert DNA. This concept, i.e. to remove a possibly competing or interfering pathway by replacing it with the desired one, is a reasonable way of choosing sites of DNA insertion.

In specific embodiments, in cases where it is desired to engineer protein glycoconjugates with modified host cells generated using the methods described herein, it is useful to delete genes that encode proteins that reduce glycoprotein yields including, without limitation, waaL, genes encoded in the enterobacterial common antigen (ECA) gene cluster (also called wec cluster), gtr prophage gene cluster genes, genes involved in nucleotide sugar biosynthesis, genes encoding periplasmic proteases, and Und-P biosynthetic and recycling genes. In some instances, host cell glycosyltransferases may interfere with recombinant polysaccharide production encoded by the DNA insert. Accordingly, a further embodiment of the invention is the deletion of host cell glycosyltransferases that modify the recombinant polysaccharide resulting in a hybrid structure with undesired characteristics.

(c) Removal of Inserted DNA

Unwanted and unnecessary sequences are of concern when recombinant bacterial strains are used for clinical material production under GIMP. Thus, in certain embodiments, auxiliary DNA sequences are removed from the host cells generated in accordance with the methods described herein once they no longer are required. For example, selection cassettes that are inserted along with the DNA of interest can be later removed so that they no longer are associated with the generated host cells. To remove such elements after insertion of DNA, different methods can be used [34]. For example, FRT/FLP derived, site specific recombination can used [35] (see the Examples). In such cases, a recombinase (e.g., FLP recombinase which recognizes a 28 bp sequence) specific for FLP sequences that flank the sequence to be removed can recombine he sequences, thereby excising the DNA between these specific sequences. Alternative excision systems are loxP/Cre, and the difXer systems [14, 36].

5.1.2.3 Other Modifications

In certain embodiments, the glycoconjugates described herein are produced in optimized growth medium. In certain embodiments, growth medium is optimized by varying one or more of (i) the amount of yeast extract in the medium (e.g., from 5 to 35 g/l), (ii) the $Mg^{2+}$ concentration of the medium (e.g., from 0 to 25 mM), (iii) the peptone extract concentration of the medium (e.g., from 5-25 g/l), (iv) the tryptone extract concentration of the medium (e.g., from 5-25 g/l), and/or (v) the addition of molecular chaperones to the medium, e.g., the addition of trehalose (e.g., 25 mM-50 mM), ethylenglycole (e.g., 0.5%), glutamic acid (e.g., 0.1 M), putrescine (e.g., 25 mM), Trimethyl-N-oxide (e.g., 5 mM), and/or L-proline (e.g., 5 mM).

In certain embodiments, growth medium is optimized by varying the pH of the medium. For example, variations from pH 6.5 to 8.5 can be evaluated for effects on glycoconjugate yield. Certain genes perform optimally at certain pH. Accordingly, growth medium can be used at pH values selected for optimization of specific genes. For example, PglB activity is optimal at ~ pH 8. Thus, in specific embodiments, the growth of host cells in the methods described herein is performed at pH 8. In another specific embodiment, the growth of host cells in the methods described herein is performed at pH ranging from 4-6, 5-7, 6-8, or 7-9.

5.1.3 Methods of Plasmid Introduction

Any methods known to those of skill in the art can be used to introduce plasmids, e.g., donor and helper plasmids, and DNA into host cells. Such methods may include, without limitation, electroporation, chemical transformation by heat shock, natural transformation, phage transduction, and conjugation.

5.1.4 Host Cells

Encompassed herein are host cells engineered by the methods described herein, wherein said host cells comprise one or more genes that encode proteins of interest. In a specific embodiment, the proteins produced by the host cells described herein are antigens, e.g., viral or bacterial antigens that can be used in vaccines. In another specific embodiment, the proteins produced by the host cells described herein are carrier proteins, wherein said carrier proteins are modified by the host cells described herein so as to possess one or more beneficial characteristics, e.g., the carrier protein is glycosylated.

In certain embodiments, the host cells provided herein are engineered using a method described in Section 5.1, above. In certain embodiments, the host cells provided herein are engineered using a method described in Section 5.1.6, below.

In certain embodiments, when host cells are engineered using a method that comprises use of helper and donor plasmids (e.g., as described in Section 5.1, above) elements encoded in the helper and donor plasmids determine if the invention can be used in a certain host cell.

Certain of the Examples below describe application of methods described herein in Gram-negative *E. coli* host cells; however, any host cells known to those of skill in the art could be used as acceptor cells for insertion of DNA, including archea, prokaryotic host cells, and eukaryotic host cells.

Exemplary prokaryotic host cells that can be used in accordance with the methods described herein include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

In certain embodiments, the host cells described herein comprise a genome into which one or more DNA sequences has been inserted, wherein said DNA sequences encode a protein or comprise an operon/gene cluster involved in the glycosylation of proteins, e.g., N-glycosylation of proteins. For example, in certain embodiments, a host cell described herein comprises a genome into which one or more of the following has been inserted: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase.

In a specific embodiment, a host cell provided herein comprises a genome into which a DNA sequence has been inserted, wherein the inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a second DNA sequence, wherein said second inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a fourth DNA sequence, wherein said fourth DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

In another specific embodiment, a host cell provided herein comprises a genome into which a DNA sequence has been inserted, wherein the inserted DNA sequence comprises two or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the genome of the host cell additionally has inserted into it a second DNA sequence, wherein said second inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

In another specific embodiment, provided herein is a host cell comprising a donor plasmid and a helper plasmid, (a) wherein the helper plasmid comprises: (i) under control of a first promoter, an open reading frame encoding lambda red recombinase; and (ii) under control of a second promoter, an open reading frame encoding a restriction endonuclease that has a recognition sequence that is not present in the host cell genome; and (b) wherein the donor plasmid comprises: (i) from 5' to 3': (1) the recognition sequence of the restriction endonuclease; (2) a first homology region of at least 0.5 kilobases (kb), (3) a heterologous insert DNA of at least 8 kb; and (4) a second homology region of at least 0.5 kb; and (ii) a counterselection marker. In a specific embodiment, the recognition sequence comprises at least 18 base pairs. In another specific embodiment, the restriction endonuclease is SceI. In a specific embodiment, the heterologous insert DNA comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

Nucleic acid sequences encoding oligosaccharyl transferases that can be inserted into the host cells described herein are known in the art. In a specific embodiment, the oligosaccharyl transferase nucleic acid sequence inserted into the genome of a host cell described herein is an oligosaccharyl transferase nucleic acid sequence derived from a prokaryotic organism. In another specific embodiment, the oligosaccharyl transferase nucleic acid sequence inserted into the genome of a host cell described herein is an oligosaccharyl transferase nucleic acid sequence from the genus *Campylobacter*. In another specific embodiment, the oligosaccharyl transferase nucleic acid sequence inserted into the genome of a host cell described herein is an oligosaccharyl transferase nucleic acid sequence from *Campylobacter jejuni* (e.g., the pglB gene from *C. jejuni*). In another specific embodiment, the oligosaccharyl transferase nucleic acid sequence inserted into the genome of a host cell described herein is an oligosaccharyl transferase nucleic acid sequence derived from a eukaryotic organism.

Nucleic acid sequences encoding glycosyltransferases that can be inserted into the host cells described herein are known in the art. In certain embodiments, the glycosyltransferase nucleic acid sequence inserted into a host cell described herein is the nucleic acid sequence of a glycosyltransferase described in International Patent Application Publication No. WO 2011/138361, the disclosure of which is incorporated by reference herein in its entirety. In a specific embodiment, the glycosyltransferase nucleic acid sequence inserted into the genome of a host cell described herein is derived from a Gram-positive bacterium, e.g., the glycosyltransferase nucleic acid sequence is derived from *S. aureus*. In another specific embodiment, the glycosyltransferase nucleic acid sequence inserted into the genome of a host cell described herein is the glycosyltransferase nucleic acid sequence of capsular polysaccharide 5 from *S. aureus*. In another specific embodiment, the glycosyltransferase nucleic acid sequence inserted into the genome of a host cell described herein is the glycosyltransferase nucleic acid sequence of capsular polysaccharide 8 from *S. aureus*. In another specific embodiment, the glycosyltransferase nucleic acid sequence inserted into the genome of a host cell described herein is derived from a Gram-negative bacterium, e.g., *E. coli*. In another specific embodiment, the glycosyltransferase nucleic acid sequence inserted into the genome of a host cell described herein is derived from a eukaryote.

Nucleic acid sequences encoding epimerases that can be inserted into the host cells described herein are known in the art. In certain embodiments, the epimerase nucleic acid sequence inserted into a host cell described herein is an epimerase nucleic acid sequence described in International Patent Application Publication No. WO 2011/062615, the disclosure of which is incorporated by reference herein in its entirety. In a specific embodiment, the epimerase nucleic acid sequence inserted into the genome of a host cell described herein is the epimerase nucleic acid sequence represented by the Z3206 gene of *E. coli* strain O157. See, e.g., WO 2011/062615 and Rush et al., 2009, The Journal of Biological Chemistry 285:1671-1680, which is incorporated by reference herein in its entirety.

Nucleic acid sequences comprising rfb gene clusters that can be inserted into the host cells described herein are known in the art. In a specific embodiment, the rfb gene cluster inserted into a host cell described herein is an rfb gene cluster from *E. coli*, e.g., an *E. coli* rfb cluster from any O serogroup/O antigen known in the art, e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, or O187, and subserotypes thereof. In another specific embodiment, the rfb gene cluster inserted into a host cell described herein is an rfb gene cluster from a *Pseudomonas* strain (e.g., a *P. aeruginosa* strain), a *Salmonella* strain (e.g., a *S. enterica* strain), a *Yersinia* strain, a *Klebsiella pneumoniae* strain, a *Francisella* strain (e.g., *F. tularensis*), an *Acinetobacter baumannii* strain, a *Burkholderia* strain, or a *Shigella* strain.

Nucleic acid sequences comprising capsular polysaccharide gene clusters that can be inserted into the host cells described herein are known in the art. In a specific embodiment, the capsular polysaccharide gene cluster inserted into a host cell described herein is a capsular polysaccharide gene cluster from an *E. coli* strain, a *Streptococcus* strain (e.g., *S. pneumoniae, S. pyrogenes, S. agalacticae*), a *Staphylococcus* strain (e.g. *S. aureus*), or a *Burkholderia* strain (e.g. *B mallei, B. pseudomallei, B. thailandensis*).

Nucleic acid sequences encoding carrier proteins that can be inserted into the host cells described herein are known in the art. The carrier proteins produced by the host cells described herein comprise at least one N-glycosylation consensus sequence, e.g., either the consensus sequence (i) Asn-X-Ser(Thr), wherein X is are independently selected from any amino acid except Pro; or (ii) D/E-X-N-Z-S/T, wherein X and Z are independently selected from any amino acid except Pro. Accordingly, the DNA sequences encoding carrier proteins inserted into the host cells described herein comprise at least one nucleic acid sequence within the carrier protein nucleic acid sequence that encodes an N-glycosylation consensus sequence. The DNA sequence encoding a carrier protein inserted into the host cells described herein can encode any carrier protein known in the art, including the carrier proteins described in Section 5.2.1.2, below. In a specific embodiment, the carrier protein nucleic acid sequence inserted into the genome of a host cell described herein is a nucleic acid sequence that encodes Exotoxin A of *P. aeruginosa* (EPA), including EPA that has been genetically modified to comprise at least one N-glycosylation consensus sequence. In another specific embodiment, the carrier protein nucleic acid sequence inserted into the genome of a host cell described herein is a nucleic acid sequence that encodes cholera toxin B. In another specific embodiment, the carrier protein nucleic acid sequence inserted into the genome of a host cell described herein is a nucleic acid sequence that encodes AcrA. In another specific embodiment, the carrier protein nucleic acid sequence inserted into the genome of a host cell described herein is a nucleic acid sequence that encodes HlA. In another specific embodiment, the carrier protein nucleic acid sequence inserted into the genome of a host cell described herein is a nucleic acid sequence that encodes ClfA.

In certain embodiments, the copy number of genes within the inserted DNA in a host cell described herein, e.g., heterologous insert DNA, is 1, 2, 3, 4, 5, 6, 7, 8, 9, or 10. In a specific embodiment, the copy number of genes within the inserted DNA in a host cell described herein, e.g., heterologous insert DNA is 1 or 2. In another specific embodiment, the copy number of genes within the inserted DNA in a host cell described herein, e.g., heterologous insert DNA is 1.

5.1.5 Analytical Methods

In certain embodiments, for functional application of the methods described herein, a combination of different selection systems for plasmid maintenance (helper plasmid, donor plasmid) and DNA insert selection is used. These selection systems should be compatible to each other, i.e. they could be like in the existing system (specR, ampR and clmR or kanR), or any alternative combination of useful antibiotics cassettes and/or alternative plasmid selection systems.

The genotypes of candidate insertion clones can be checked by any methods used for DNA analysis. Screening must be based on analyzing the presence of the DNA insert in the context of the chromosomal insertion location. This means that DNA inserts must be found next to the target site, i.e. sequences outside the target site region. PCR can be done for showing absence of a gene that has been excised by recombination, for instance when an O antigen cluster is exchanged with a different one. Or it can be used to show presence of DNA insert. Or it can be used to amplify a DNA stretch using oligonucleotides that flank the HRs, showing that a joining of chromosomal DNA and DNA insert had occurred. DNA sequencing can show the same result, i.e. the DNA insert sequence must be continuously connected to the chromosomal DNA sequences not affected by the homologous recombination. Or southern blot could be used to identify chromosomal DNA fragments containing DNA insert and unaffected chromosomal sequences next to the insertion (HR) site. Or colony hybridization with PCR probes specific for a DNA insert piece may be used.

Another way of showing the presence of the DNA insert is by assessing the activity of the inserted genes. Phenotypic analysis of candidate clones allows checking for activity of the DNA insert, but not for the correct insertion location. In the examples shown below, a recombinant polysaccharide biosynthesis gene cluster was inserted, thus a simple experiment showing the presence of the polysaccharide after insertion in the recombined cell is sufficient for confirming successful recombination. This may be done by immuno blots using polysaccharide specific antisera (Western blot, colony blot, dot blot, etc) possibly but not necessarily in combination with separation of cellular extracts by SDS PAGE or chromatography followed by western blotting or ELISA; also, high resolution techniques like MS, NMR, HPLC, or chemical or physical identification methods for the product are useful to confirm the DNA insert activity.

5.1.6 Additional Insertion Methods

In addition to the novel insertion methods described above (e.g., in Section 5.1), DNA can be inserted into the genome of a host cell using other approaches. In certain embodiments, DNA is inserted into the genome of a host cell using any site-specific insertion method known in the art. In certain embodiments, DNA is inserted into the genome of a host cell using any random integration method known in the art. Such methods are described in greater detail below.

In certain embodiments, DNA is inserted into a host cell (e.g., *E. coli*) genome using a method that comprises transposon-mediated insertion. Such random insertion allows for insertion of DNA of interest at multiple locations of the host cell genome, and thus allows for the identification of optimal insertion sites in host cells into which DNA has been inserted, e.g., host cells bearing inserted DNA can be compared with one another with regard to efficiency of production of the inserted DNA and host cells with highest efficiency can be selected for future use. Methods of transposon-mediated insertion of nucleic acid sequences into host cell genomes are known in the art. For example, in certain embodiments, the pUTminiTn5 delivery system (Biomedical; Sevilla, Spain) is used to stably inserted genes into the genomes of host cells (such as bacterial host cells). Strains into which DNA has been inserted then can be identified and isolated. See also Herrero et al., 1990, J. Bacteriology 172(11):6557-6567 and DeLorenzo et al., 1990, J. Bacteriology 172(11):6568-6572, each of which is herein incorporated by reference in its entirety. In addition, in certain embodiments, transposon-mediated insertion of DNA into a host cell genome is accomplished using a Tn-7 based method of DNA insertion. See McKenzie et al., 2006, BMC Microbiology 6:39 and Sibley et al., 2012, Nucleic Acids Res. 40:e19, each of which is herein incorporated by reference in its entirety.

In certain embodiments, DNA is inserted into a host cell (e.g., *E. coli*) genome using the StabyCloning™ kit or the StabyCodon T7 kit (Delphi Genetics, Charleroi, Belgium), which allow for site-specific DNA cloning.

In certain embodiments, DNA is inserted into a host cell (e.g., *E. coli*) genome using the "clonetegration" method of cloning and chromosomal integration of DNA. See St. Pierre et al, 2013, ACS Synthetic Biology 2:537-541, the disclosure of which is herein incorporated by reference in its entirety.

In certain embodiments, DNA is inserted into a host cell (e.g., *E. coli*) genome using a method that involves conditional-replication, integration, and modular (CRIM) plasmids, as described by Haldimann and Wanner, 2001, J. Bacteriology 183:6384-6393, the disclosure of which is herein incorporated by reference in its entirety.

In certain embodiments, DNA is inserted into a host cell (e.g., *E. coli*) genome using recombineering, a method described by, for example, Sharan et al., 2009, Nat. Protoc. 4:206-223; Yu et al., 2000, PNAS USA 97:5978-5983; Kuhlman et al., 2010, Nucleic Acids Res. 38:e92; and Zhang et al., 1998, Nat. Genet. 20:123-128, each of which is herein incorporated by reference in its entirety.

Further provided herein are isolated donor DNA constructs used in the additional insertion methods described herein. The DNA constructs are engineered such that they can be used in the integration method applied, and comprise nucleic acids that encode/comprise one or more proteins/operons/gene clusters to be inserted into a host cell genome in accordance with the method being performed. In certain embodiments, the isolated donor DNA constructs comprise nucleic acids that encode/comprise one or more proteins or operons involved in the glycosylation of proteins, e.g., the N-glycosylation of proteins. In a specific embodiment, the isolated donor DNA constructs comprise one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

5.2 Applications

5.2.1 Protein Glycosylation

In certain embodiments, the modified host cells provided herein can be used for protein glycosylation. Protein glycosylation may designed to produce conjugate vaccines, i.e. vaccines that contain polysaccharide and protein antigens of the pathogen that the vaccine is designed against.

5.2.1.1 Antigens

DNA encoding genes associated with the following polysaccharide antigens can be used as insert DNA in accordance with the methods described herein:

O antigens of *E. coli* (O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), *Salmonella* sp (*S. enterica* subsp. *Enterica*, *S. enterica* subsp. *Salamae*, *S. enterica* subsp. *arizonae*, *S. enterica* subsp. *Diarizonae*, *S. enterica* subsp. *Houtenae*, *S. bongori*, and *S. enterica* subsp. *Indica*, and O types 1-67, as detailed in [37], *Pseudomonas* sp (*P. aeruginosa* O serotypes 1-20 [38]), *Klebsiella* sp. (particularly *K. pneumonia* serotypes O1, O2 (and subserotypes), O3, O4, O5, O6, O7, O8, O9, O10, O11, O12, [39]), *Acinetobacter* O antigens (in particular *A. baumannii* O antigens identified in [40]), *Chlamydia trachomatis* O antigens (serotypes A, B, C, D, E, F, G, H, I J, K, L1, L2, L3), *Vibrio cholera* O antigens O1 to 155, *Listeria* sp., in particular *L. monocytogenes* type 1, 2, 3, 4 and subserotypes thereof, Legionellapneumophila serotypes 1 to 15 O antigens, *Bordetella parapertussis* O antigens, *Burkholderia mallei* and *pseudomallei* O antigens, *Francisella tularensis*, *Campylobacter* sp. (*C. jejuni*); Capsular polysaccharides of *Clostridium difficile* (serotypes A, G, H, K, S1, S4, D, Cd-5, K Toma et al 1988, and *C. perfringens* serotypes A, B, C, D und E), *Staphylococcus aureus* type 5 and 8, *Streptococcus pyogenes* (group B *streptococcus* capsular serotype polysaccharides), *E. coli*, *Streptococcus agalacticae* (group A streptococcal capsular polysaccharides), *Neisseria meningitidis* (serotypes A, B, C, W, Y, X), *Candida albicans*, *Haemophilus* influenza, *Enterococcus faecalis* capsular polysaccharides type I-V; and other surface polysaccharide structures, e.g. the *Borrelia burgdorferi* glycolipids ([41]), *Neisseria meningitidis* pilin O glycan [42, 43] and lipooligosaccharide (LOS), *Haemophilus influenza* LOS, *Leishmania major* lipophosphoglycan [44, 45]), tumor associated carbohydrate antigens (malaria glycosyl phosphatidylinositol, *Mycobacterium tuberculosis* arabinomannan [46].

5.2.1.2 Carrier Proteins

Nucleic acids encoding/comprising any carrier protein suitable for use in the production of conjugate vaccines can be used herein. Exemplary carrier proteins include, without limitation, Exotoxin A of *P. aeruginosa* (EPA), CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

In certain embodiments, the carrier proteins used in the generation of the conjugate vaccines described herein are modified, e.g., modified in such a way that the protein is less toxic and or more susceptible to glycosylation, etc. In a specific embodiment, the carrier proteins used in the generation of the conjugate vaccines described herein are modified such that the number of glycosylation sites in the carrier proteins is maximized in a manner that allows for lower concentrations of the protein to be administered, e.g., in an immunogenic composition, in its bioconjugate form. Accordingly in certain embodiments, the carrier proteins described herein are modified to include 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In specific embodiments, introduction of glycosylation sites is accomplished by insertion of glycosylation consensus sequences (e.g., (i) the consensus sequence Asn-X-Ser(Thr), wherein X is are independently selected from any amino acid except Pro; or (ii) the consensus sequence D/E-X-N-Z-S/T, wherein X and Z are independently selected from any amino acid except Pro) anywhere in the primary structure of the protein. Introduction of such glycosylation sites can be accomplished by, e.g., adding new amino acids to the primary structure of the protein (i.e., the glycosylation sites are added, in full or in part), or by mutating existing amino acids in the protein in order to generate the glycosylation sites (i.e., amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids.

In certain embodiments, the carrier proteins used in the generation of the conjugate vaccines described herein comprise a "tag," i.e., a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein include, without limitation, histidine (HIS) tags (e.g., hexa histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified.

5.2.1.3 Host Cell Modifications

In certain embodiments, the host cells used to produce the conjugate vaccines described herein are engineered to comprise heterologous nucleic acids, e.g., heterologous nucleic acids that encode one or more carrier proteins and/or heterologous nucleic acids that encode one or more proteins, e.g., genes encoding one or more proteins. In a specific embodiment, heterologous nucleic acids that encode proteins involved in glycosylation pathways (e.g., prokaryotic and/or eukaryotic glycosylation pathways) may be introduced into the host cells described herein. Such nucleic acids may encode proteins including, without limitation, oligosaccharyl transferases and/or glycosyltransferases, as well as epimerases and antigen gene clusters. Heterologous nucleic acids (e.g., nucleic acids that encode carrier proteins and/or nucleic acids that encode other proteins, e.g., proteins involved in glycosylation) can be introduced into the host cells described herein using any methods known to those of skill in the art, e.g., electroporation, chemical transformation by heat shock, natural transformation, phage transduction, and conjugation. In specific embodiments, heterologous nucleic acids are introduced into the host cells described herein using a plasmid, e.g., the heterologous nucleic acids are expressed in the host cells by a plasmid (e.g., an expression vector). In another specific embodiment, heterologous nucleic acids are introduced into the host cells described herein using the methods of insertion provided herein.

In certain embodiments, additional modifications may be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein or do not encode a protein whatsoever). In certain embodiments, when nucleic acids are deleted from the genome of the host cells provided herein, they are replaced by a desirable sequence, e.g., a sequence that is useful for glycoprotein production. Such replacement can be by way of one or more of the methods of insertion described herein, wherein the heterologous insert DNA that is inserted into the host cell may replace the function of the gene(s) deleted from the host cell.

Exemplary genes that can be deleted in host cells (and, in some cases, replaced with other desired nucleic acid sequences) include genes of the host cells involved in glycolipid biosynthesis, such as waaL (see, e.g., Feldman et al., 2005, PNAS USA 102:3016-3021), lipid A core biosynthesis cluster, galactose cluster, arabinose cluster, colonic acid cluster, capsular polysaccharide cluster, undecaprenol-p biosynthesis genes, und-P recycling genes, metabolic enzymes involved in nucleotide activated sugar biosynthesis, enterobacterial common antigen cluster, and prophage O antigen modification clusters like the grabs cluster. In a specific embodiment, the host cells described herein are modified such that they do not produce any O antigens other than an O antigen that is produced as a result of the insertion of heterologous insert DNA into the genome of the host cell by a method described herein. In another specific embodiment, the host cells described herein are modified such that they do not produce any capsular polysaccharides other than a capsular polysaccharide that is produced as a result of the insertion of heterologous insert DNA into the genome of the host cell by a method described herein.

In certain embodiments, the host cells provided herein comprise a gene deletion, wherein a DNA sequence of interest has been inserted into the host cell genome at the site of the gene deletion. In a specific embodiment, a host cell provided herein is *E. coli* bearing a deletion of the waaL gene. In a specific embodiment, a DNA sequence encoding an oligosaccharyl transferase is inserted at the site of the waaL gene deletion in the *E. coli* host cell. In another specific embodiment, a host cell provided herein is *E. coli* bearing a deletion of the wecG gene. In a specific embodiment, a DNA sequence encoding a carrier protein is inserted at the site of the wecG gene deletion in the *E. coli* host cell. In another specific embodiment, a host cell provided herein is *E. coli* bearing a deletion of the waaL gene and a deletion of the wecG gene, wherein an oligosaccharyl transferase is inserted into the *E. coli* host cell at the site of the deleted waaL gene and wherein a carrier protein (e.g., EPA comprising an N-glycosylation consensus sequence) is inserted into the *E. coli* host cell at the site of the deleted wecG gene.

5.2.1.4 Glycoconjugates

The methods described herein can be used to produce host cells that produce glycoconjugates comprising a glycosylated carrier protein (see, e.g., Section 5.2.1.2). In specific embodiments, provided herein are glycoconjugates comprising a carrier protein (see, e.g., Section 5.2.1.2) glycosylated with an antigen (e.g., a polysaccharide) described herein, e.g., an antigen described in Section 5.2.1.1. In specific embodiments, the carrier protein is EPA.

In a specific embodiment, provided herein is a glycoconjugate comprising EPA and one or more different polysaccharides, e.g., one or more polysaccharides described in Section 5.2.1.1.

In another specific embodiment, provided herein is a glycoconjugate comprising a carrier protein conjugated to one or more of *E. coli* O1, O2, O4, O6, O7, O8, O11, O15, O16, O17, O18, O20, O22, O25, O73, O75, and/or O83. In a specific embodiment, the carrier protein is EPA.

In another specific embodiment, provided herein is a glycoconjugate comprising a carrier protein conjugated to one or more different *P. aeruginosa* polysaccharides. In a specific embodiment, the carrier protein is EPA.

In another specific embodiment, provided herein is a glycoconjugate comprising a carrier protein conjugated to one or more different *K. pneumonia* polysaccharides. In a specific embodiment, the carrier protein is EPA.

5.2.1.5 Benefits

The methods of producing glycoconjugates described herein are of particular commercial importance and relevance, as they allow for large scale fermentation at a lower risk due to the increased stability of the chromosomally inserted DNA and thus expression of the DNA of interest during fermentation. Certain known methods for maintaining insert DNA expression are based on episomes carrying the insert DNA. These episomes need to be maintained by antibiotic selection. Certain of the methods described herein thus are advantageous over plasmid borne expression of the inserted DNA because, inter alia, antibiotic selection during fermentation is not required once the heterologous DNA is inserted into the host cell genome. That is, when the insert DNA is inserted in the chromosome, it doesn't need to be selected for, because it is propagated along with replication of the host genome. Further, it is a known disadvantage in plasmid borne systems that with every generation (i.e., cycle of host cell replication) the risk for losing the plasmid increases. This loss of plasmid is due to the sometimes inappropriate distribution of plasmids to daughter cells at the stage of cell separation during cell division. At large scale, bacterial cell cultures duplicate more often than in smaller fermentation scales to reach high cell densities. Thus, higher cell stability and insert DNA expression leads to higher product yields, providing a distinct advantage. Cell stability is furthermore a process acceptance criteria for approval by regulatory authorities, while antibiotic selection is generally not desired during fermentation for various reasons, e.g., antibiotics present as impurities in the final medical products and bear the risk of causing allergic reactions, and antibiotics may promote antibiotic resistance (e.g., by gene transfer or selection of resistant pathogens). The host cells provided herein thus are advantageous, in that they comprise fewer number of plasmids required for production of bioconjugates. For example, bioconjugates can be produced from host cells (e.g. *E. coli*) that comprise 2, 1, or no plasmids, i.e., some or all of the heterologous machinery required for bioconjugate production is inserted into the genome of the host cells, thus reducing the number of plasmids required.

Another advantage of the methods described herein is that, in certain embodiments, large pieces of DNA can be inserted into the genome of host cells at once ("at-once-insertion). Certain existing methods for introduction of DNA into host cell genome employ the repeated insertion of small DNA fragments by homologous recombination [47]. Thus, without being limited by theory, the methods of at-once-insertion described herein are advantageous because they allow for the avoidance of multiple insertions.

5.2.1.6 Analytical Methods

Various methods can be used to analyze the structural compositions and sugar chain lengths of the glycoconjugates described herein.

Figure 21:
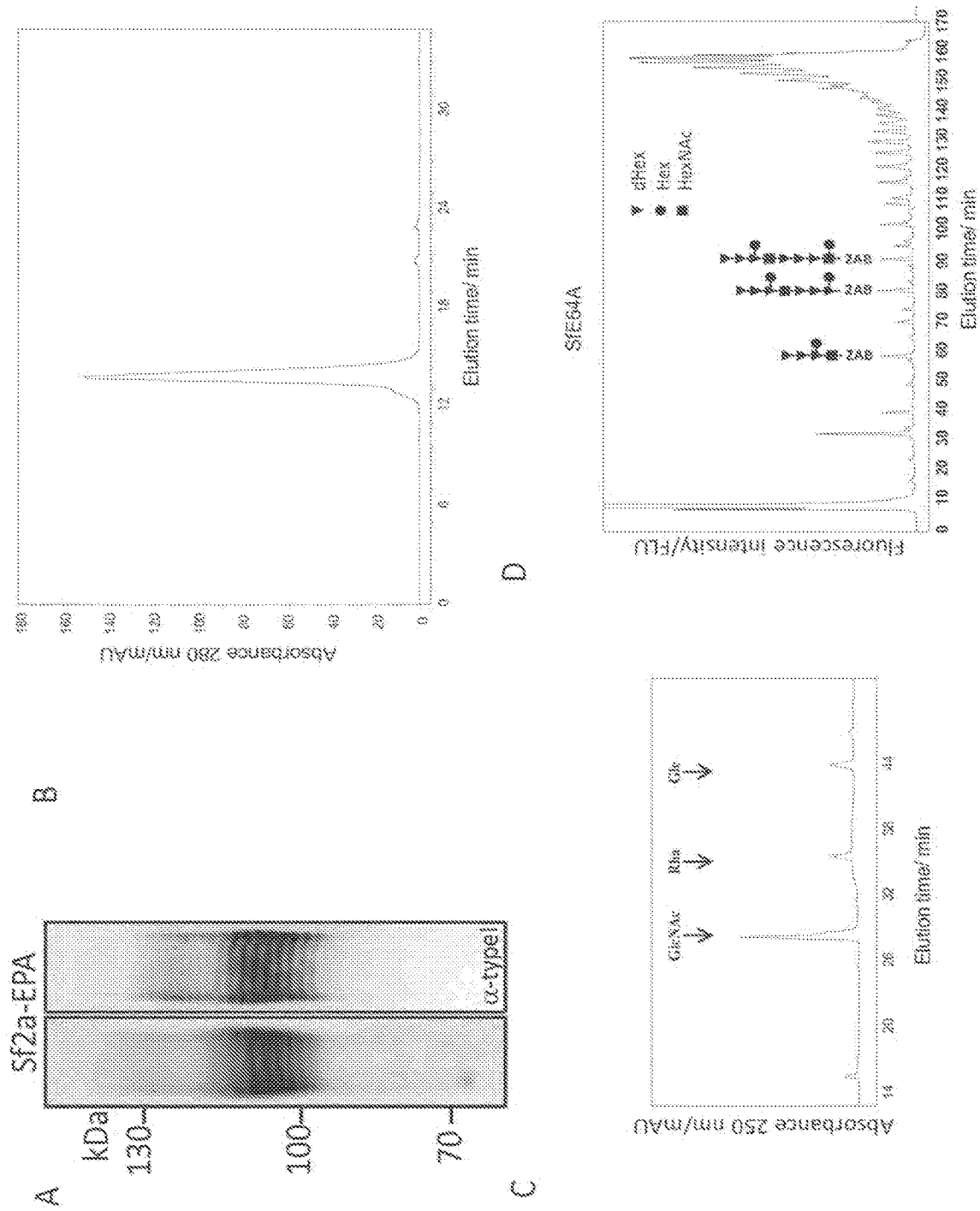
Figure 22:
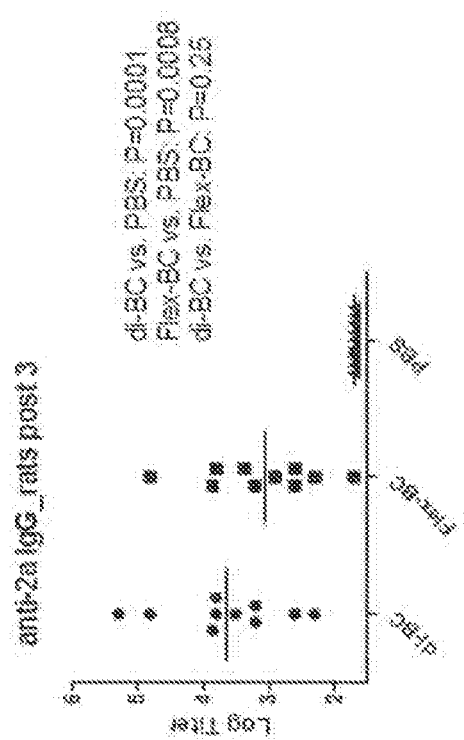
Figure 23:
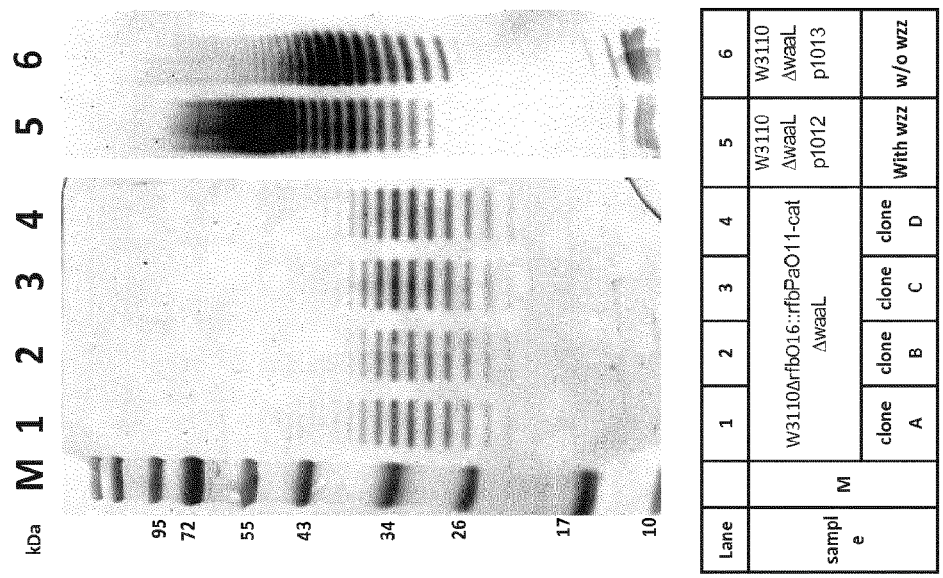

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide [48]. The labeled polysaccharides are separated on a GlycoSep-N column (GL Sciences) according to the HPLC protocol of Royle et al. [49]. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit could be confirmed and additionally in homogeneity of the polysaccharide composition could be identified. HPLC chromatograms obtained after hydrazinolysis and 2 AB labeling are shown in one of the examples (FIG. 21). Specific peaks of low molecular weight can be analyzed by MALDI-MS/MS and the result is used to confirm the glycan sequence. Each peak corresponds to a polymer consisting of a certain number of repeat units and fragments thereof. The chromatogram thus allows to measure the polymer length distribution. The elution time is a indication for polymer length, fluorescence intensity correlates with molar abundance for the respective polymer.

In another embodiment, SDS-PAGE or capillary gel electrophoresis can be used to assess glycans and glycoconjugates. Polymer length for the O antigen glycans which are synthesized here is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size: The unglycosylated carrier protein and the glycoconjugate with different polymer chain lengths separate according to their electrophoretic mobilities. The first detectable repeating unit number (n) and the average repeating unit number ($n_{average}$) present on a glycoconjugate are measured. These parameters can be used to demonstrate batch to batch consistency or polysaccharide stability.

In another embodiment, high mass MS and size exclusion HPLC could be applied to measure the size of the complete glycoconjugates.

In another embodiment, an anthrone-sulfuric acid assay can be used to measure polysaccharide yields [50].

(a) Change in Glycosylation Site Usage

To show that the site usage in a specific protein is changed in a three plasmid system as opposed to an inserted system, the glycosylation site usage must be quantified. Methods to do so are listed below.

Glycopeptide LC-MS/MS: glycoconjugates are digested with protease(s), and the peptides are separated by a suitable chromatographic method (C18, Hydriphilic interaction HPLC HILIC, GlycoSepN columns, SE HPLC, AE HPLC), and the different peptides are identified using MS/MS. This method can be used with our without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by a earlier elution time from a SE HPLC column. See also (a).

(b) Homogeneity

Glycoconjugate homogeneity (i.e., the homogeneity of the attached sugar residues) can be assessed using methods that measure glycan length and hydrodynamic radius (see above and Section 5.3.5).

5.2.2 Other Potential Clinical/Practical Applications

The methods described herein can be used for the construction of any host cell for which is desirable to introduce large DNA fragments into the host cell geneome, wherein the DNA fragments are maintained during production of the host cell line carrying the insert DNA (e.g., large scale production of the host cell line to yield a desired product, e.g., a protein encoded by the insert DNA). For example, the methods described herein can be used to produce host cells that comprise inserted DNA that encodes, without limitation, antibiotics, alkaloids, carotnoides, nicotinamide and other secondary metabolites and co-factors which are synthesized by multiple enzymatic reactions within the same cell. Accordingly, provided herein are host cells comprising inserted DNA encoding such components.

5.2.3 Higher Yield of Proteins

Integrated strains can make a higher yield of glycoconjugates due to the reduced antibiotic selection burden as compared to the three plasmid system. In addition, less proteolytic degradation occurs due to reduced metabolic burden to the cells.

5.2.4 Higher Homogeneity of Proteins

Integrated strains make glycoconjugates with shorter, less spread polysaccharide length distributions. Thus, the glycoconjugates are easier to characterize and are better defined. In addition, insertion may reduce the extent of periplasmic stress to the cells which may lead to less proteolysis of product during the fermentation process due to the reduced antibiotic selection burden as compared to the three plasmid system.

5.2.5 Higher Production Strain Stability

Protein glycosylation systems require three recombinant elements in the production host: a carrier protein expression DNA, an oligosaccharyl transferase expression DNA, and a polysaccharide expression DNA. Prior art bacterial production systems contain these three elements on plasmids. Thus, there is a risk for instability during manufacture due to plasmid loss, particularly because antibiotics used for maintenance of the plasmids mustn't be present during fermentation of GIMP material. Since inserted strains contain yet a mobile element less, they are more stable over many generations. This means that higher scale fermentations and longer incubation times (higher generation numbers) are more feasible. In addition, the absence of an antibiotic for selection makes a safer product, due to the absence of trace antibiotics which can cause allergic reactions in sensitive subjects [4].

5.2.6 Higher Reproducibility of the Production Process

Inserted strains are more genetically stable due to the fixed chromosomal insertion, thus leading to higher reproducibility of desired protein products during the production process, e.g., during culture of host cell comprising inserted heterologous DNA.

5.2.7 Analytical Methods for Testing Benefit

Yield. Yield is measured as carbohydrate amount derived from a liter of bacterial production culture grown in a bioreactor under controlled and optimized conditions. After purification of glycoconjugate, the carbohydrate yields can be directly measured by either the anthrone assay (see, e.g., Section 5.2.1.7), or ELISA using carbohydrate specific antisera. Indirect measurements are possible by using the protein amount (measured by well known BCA, Lowry, or bardford assays) and the glycan length and structure to calculate a theoretical carbohydrate amount per gram of protein. In addition, yield can also be measured by drying the glycoprotein preparation from a volatile buffer and using a balance to measure the weight.

Homogeneity. Homogeneity means the variability of glycan length and possibly the number of glycosylation sites. Methods listed above can be used for this purpose. SE-HPLC allows the measurement of the hydrodynamic radius. Higher numbers of glycosylation sites in the carrier lead to higher variation in hydrodynamic radius compared to a carrier with less glycosylation sites. However, when single glycan chains are analyzed, they may be more homogenous due to the more controlled length. Glycan length is measured by hydrazinolysis, SDS PAGE, and CGE (see Section 5.1.2.7.). In addition, homogeneity can also mean that certain glycosylation site usage patterns change to a broader/narrower range. These factors can be measured by Glyco-peptide LC-MS/MS (see Section 5.1.2.7).

Strain stability and reproducibility. Strain stability during bacterial fermentation in absence of selective pressure is measured by direct and indirect methods that confirm presence or absence of the recombinant DNA in production culture cells. Culture volume influence can be simulated by elongated culturing times meaning increased generation times. The more generations in fermentation, the more it is likely that a recombinant element is lost. Loss of a recombinant element is considered instability. Indirect methods rely on the association of selection cassettes with recombinant DNA, e.g. the antibiotic resistance cassettes in a plasmid. Production culture cells are plated on selective media, e.g. LB plates supplemented with antibiotics or other chemicals related to a selection system, and resistant colonies are considered as positive for the recombinant DNA associated to the respective selection chemical. In the case of a three plasmid system, resistant colonies to all three antibiotics are counted and the proportion of cells containing all three resistances is considered the stable population. Alternatively, quantitative PCR can be used to measure the amount of recombinant DNA of the three recombinant elements in the presence, absence of selection, and at different time points of fermentation. Thus, the relative and absolute amount of recombinant DNA is measured and compared. Reproducibility of the production process is measured by the complete analysis of consistency batches by the methods stated in this application.

5.3 Compositions

5.3.1 Compositions Comprising the Plasmids

In one embodiment, provided herein are compositions comprising one or more of the plasmids described herein, e.g., one or more donor or helper plasmids.

In a specific embodiment, provided herein is a composition comprising a donor plasmid, wherein said donor plasmid comprises (i) from 5' to 3': (1) the recognition sequence of the restriction endonuclease; (2) a first homology region of at least 0.5 kilobases (kb), (3) a heterologous insert DNA of at least 8 kb; and (4) a second homology region of at least 0.5 kb; and (ii) a counterselection marker.

In another specific embodiment, provided herein is a composition comprising a helper plasmid, wherein said helper plasmid comprises (i) under control of a first promoter, an open reading frame encoding lambda red recombinase; and (ii) under control of a second promoter, an open reading frame encoding a restriction endonuclease that has a recognition sequence that is not present in the host cell genome.

In another specific embodiment, provided herein is a composition comprising a donor plasmid and a helper plasmid, wherein said donor plasmid comprises (i) from 5' to 3': (1) the recognition sequence of the restriction endonuclease; (2) a first homology region of at least 0.5 kilobases (kb), (3) a heterologous insert DNA of at least 8 kb; and (4) a second homology region of at least 0.5 kb; and (ii) a counterselection marker; and wherein said helper plasmid comprises (i) under control of a first promoter, an open reading frame encoding lambda red recombinase; and (ii) under control of a second promoter, an open reading frame encoding a restriction endonuclease that has a recognition sequence that is not present in the host cell genome.

5.3.2 Compositions Comprising Host Cells

In one embodiment, provided herein are compositions comprising one or more of the host cells described herein. Such compositions can be used in methods for generating the conjugate vaccines described herein, e.g., the compositions can be cultured under conditions suitable for the production of proteins. Subsequently, the bioconjugates can be isolated from said compositions.

The compositions comprising the host cells provided herein can comprise additional components suitable for maintenance and survival of the host cells described herein, and can additionally comprise additional components required or beneficial to the production of proteins by the host cells, e.g., inducers for inducible promoters, such as arabinose, IPTG.

In a specific embodiment, a composition provided herein comprises a host cell, wherein said host cell comprises a donor plasmid and a helper plasmid, (a) wherein the helper plasmid comprises: (i) under control of a first promoter, an open reading frame encoding lambda red recombinase; and (ii) under control of a second promoter, an open reading frame encoding a restriction endonuclease that has a recognition sequence that is not present in the host cell genome; and (b) wherein the donor plasmid comprises: (i) from 5' to 3': (1) the recognition sequence of the restriction endonuclease; (2) a first homology region of at least 0.5 kilobases (kb), (3) a heterologous insert DNA of at least 8 kb; and (4) a second homology region of at least 0.5 kb; and (ii) a counterselection marker. In a specific embodiment, the recognition sequence comprises at least 18 base pairs. In another specific embodiment, the restriction endonuclease is SceI. In another specific embodiment, the host cell is *E. coli*.

In another specific embodiment, a composition provided herein comprises a host cell, wherein said host cell comprises a genome into which a DNA sequence has been inserted, wherein the inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the genome of the host cell additionally has inserted into it a second DNA sequence, wherein said second inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a fourth DNA sequence, wherein said fourth DNA sequence comprises one of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

In another specific embodiment, a composition provided herein comprises a host cell, wherein said host cell comprises a genome into which a DNA sequence has been inserted, wherein the inserted DNA sequence comprises two or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the genome of the host cell additionally has inserted into it a second DNA sequence, wherein said second inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In another specific embodiment, the genome of the host cell additionally has inserted into it a third DNA sequence, wherein said third inserted DNA sequence comprises one or more of the following: DNA encoding an oligosaccharyl transferase, DNA encoding a glycosyltransferase, DNA encoding a carrier protein, DNA comprising an rfb gene cluster, DNA comprising a capsular polysaccharide gene cluster, and/or DNA encoding an epimerase. In a specific embodiment, the host cell is *E. coli*.

In another specific embodiment, a composition provided herein comprises a host cell, wherein said host cell comprises a DNA sequence that has been inserted into its genome, wherein said inserted DNA sequence comprises a gene encoding an oligosaccharyl transferase. In a specific embodiment, the oligosaccharyl transferase is an oligosaccharyl transferase derived from a prokaryotic organism. In another specific embodiment, the oligosaccharyl transferase is an oligosaccharyl transferase from the genus *Campylobacter*. In another specific embodiment, the oligosaccharyl transferase is an oligosaccharyl transferase from *Campylobacter jejuni* (e.g., the pglB gene from *C. jejuni*). In another specific embodiment, the oligosaccharyl transferase is derived from a eukaryotic organism. In another specific embodiment, the oligosaccharyl transferase is the oligosaccharyl transferase described in U.S. Patent Application Publication No. 20120156723, which is hereby incorporated by reference in its entirety. In another specific embodiment, the host cell is *E. coli*. In another specific embodiment, said host cell is *E. coli* bearing a deletion of the waaL gene, and said oligosaccharyl transferase is inserted into the *E. coli* host cell at the site of the deleted waaL gene.

In another specific embodiment, a composition provided herein comprises a host cell, wherein said host cell comprises a DNA sequence that has been inserted into its genome, wherein said inserted DNA sequence comprises a gene encoding a carrier protein, wherein said carrier protein comprises at least one N-glycosylation consensus sequence, e.g., either the consensus sequence (i) Asn-X-Ser(Thr), wherein X is are independently selected from any amino acid except Pro; or (ii) D/E-X-N-Z-S/T, wherein X and Z are independently selected from any amino acid except Pro. The carrier protein may be any carrier protein known in the art, including the carrier proteins described in Section 5.2.1.2, below. In a specific embodiment, the carrier protein is Exotoxin A of *P. aeruginosa* (EPA), including EPA that has been genetically modified to comprise at least one N-glycosylation consensus sequence. In another specific embodiment, the host cell is *E. coli*. In another specific embodiment, said host cell is *E. coli* bearing a deletion of the wecG gene, and said carrier protein (e.g., EPA) is inserted into the *E. coli* host cell at the site of the deleted wecG gene.

In another specific embodiment, a composition provided herein comprises a host cell, wherein said host cell comprises a first DNA sequence and a second DNA sequence that have been inserted into its genome, wherein said first inserted DNA sequence comprises a gene encoding an oligosaccharyl transferase and wherein the second inserted DNA sequence comprises a gene encoding a carrier protein (e.g., a carrier protein described in Section 5.2.1.2, below) wherein said carrier protein comprises at least one N-glycosylation consensus sequence, e.g., either the consensus sequence (i) Asn-X-Ser(Thr), wherein X is are independently selected from any amino acid except Pro; or (ii) D/E-X-N-Z-S/T, wherein X and Z are independently selected from any amino acid except Pro. In a specific embodiment, the oligosaccharyl transferase is an oligosaccharyl transferase derived from a prokaryotic organism. In another specific embodiment, the oligosaccharyl transferase is an oligosaccharyl transferase from the genus *Campylobacter*. In another specific embodiment, the oligosaccharyl transferase is an oligosaccharyl transferase from *Campylobacter jejuni* (e.g., the pglB gene from *C. jejuni*). In another specific embodiment, the oligosaccharyl transferase is derived from a eukaryotic organism. In another specific embodiment, the oligosaccharyl transferase is the oligosaccharyl transferase described in U.S. Patent Application Publication No. 20120156723, which is hereby incorporated by reference in its entirety. In another specific embodiment, the carrier protein is Exotoxin A of *P. aeruginosa* (EPA), including EPA that has been genetically modified to comprise at least one N-glycosylation consensus sequence. In another specific embodiment, the host cell is *E. coli*. In another specific embodiment, said host cell is *E. coli* bearing a deletion of the waaL gene and a deletion of the wecG gene, wherein said oligosaccharyl transferase is inserted into the *E. coli* host cell at the site of the deleted waaL gene and wherein said carrier protein (e.g., EPA) is inserted into the *E. coli* host cell at the site of the deleted wecG gene.

5.3.3 Immunogenic Compositions 5.3.3.1 Compositions Comprising Glycosylated Proteins In one embodiment, provided herein are immunogenic compositions comprising one or more glycoconjugates produced by a host cell described herein. Such glycoconjugates may comprise an O antigen glycan attached to a glycosylation consensus sequence encoded within a protein, e.g., a carrier protein. In a specific embodiment, the carrier protein may be Exotoxin A comprising one or more introduced glycosylation sites, or the carrier protein may be FimCH and comprising one or more introduced glycosylation sites. In other specific embodiments, the carrier protein may comprise an *E. coli* protein antigen comprising one or more introduced glycosylation sites. In a specific embodiment, the O antigens are *E. coli* O antigens from pathogenic *E. coli* isolates, e.g., O1, O2, O4, O7, O8, O9, O11, O15, O16, O17, O18; O20, O22, O25, O73, O75, or O83.

In another specific embodiment, an immunogenic composition provided herein comprises a carrier protein (e.g., a carrier protein described in Section 5.2.1.2) conjugated to an antigen described herein, e.g., an antigen described in Section 5.2.1.1. In a specific embodiment, the carrier protein is EPA. In another specific embodiment, the antigen is an *E. coli* antigen, e.g., an *E. coli* polysaccharide.

In another specific embodiment, an immunogenic composition provided herein comprises a carrier protein (e.g., a carrier protein described in Section 5.2.1.2, e.g., EPA) glycosylated by the *E. coli* O antigen of the O1 serotype (O1-EPA).

In another specific embodiment, an immunogenic composition provided herein comprises a carrier protein (e.g., a carrier protein described in Section 5.2.1.2, e.g., EPA) glycosylated by the *E. coli* O antigen of the O2 serotype (O2-EPA).

In another specific embodiment, an immunogenic composition provided herein comprises a carrier protein (e.g., a carrier protein described in Section 5.2.1.2, e.g., EPA) glycosylated by the *E. coli* O antigen of the O6 serotype (O6-EPA).

In other specific embodiments, an immunogenic composition provided herein comprises a carrier protein (e.g., a carrier protein described in Section 5.2.1.2, e.g., EPA) glycosylated by an *E. coli* O antigen of the O1, O2, O4, O7, O8, O9, O11, O15, O16, O17, O18; O20, O22, O25, O73, O75, or O83 serotype.

The immunogenic compositions provided herein can be used for eliciting an immune response in a host to whom the composition is administered. Thus, the immunogenic compositions described herein can be used as vaccines and can accordingly be formulated as pharmaceutical compositions. In a specific embodiment, the immunogenic compositions described herein are used in the prevention of infection of subjects (e.g., human subjects) by *E. coli*. In a specific embodiment, the immunogenic compositions described herein are used as a vaccine against a urinary tract infection caused by infection of *E. coli*.

For example, an immunogenic composition described herein for use as a vaccine against a urinary tract infection caused by infection of *E. coli* may comprise a carrier protein (e.g., a carrier protein described in Section 5.2.1.2, e.g., EPA) glycosylated by an *E. coli* antigen (e.g., an *E. coli* antigen described in Section 5.2.1.1). In a specific embodiment, the *E. coli* antigen is an O antigen of the O1, O2, O4, O7, O8, O9, O11, O15, O16, O17, O18; O20, O22, O25, O73, O75, or O83 serotype.

In another specific embodiment, the immunogenic compositions described herein are used in the prevention of infection of subjects (e.g., human subjects) by *Pseudomonas*. In another specific embodiment, the immunogenic compositions described herein are used in the prevention of infection of subjects (e.g., human subjects) by *Shigella*.

The compositions comprising the bioconjugates described herein may comprise any additional components suitable for use in pharmaceutical administration. In specific embodiments, the immunogenic compositions described herein are monovalent formulations. In other embodiments, the immunogenic compositions described herein are multivalent formulations. For example, a multivalent formulation comprises more than one bioconjugate described herein.

In certain embodiments, the compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a bioconjugate, but when the compound is administered alone does not generate an immune response to the bioconjugate. In some embodiments, the adjuvant generates an immune response to the poly bioconjugate peptide and does not produce an allergy or other adverse reaction. Adjuvants can enhance an immune response by several mechanisms including, e.g., lymphocyte recruitment, stimulation of B and/or T cells, and stimulation of macrophages. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998).

5.4 Methods of Treatment and Immunization

In one embodiment, provided herein are methods of treating an infection in a subject comprising administering to the subject a glycoconjugate described herein or a composition thereof. In a specific embodiment, a method for treating an infection described herein comprises administering to a subject in need thereof an effective amount of a glycoconjugate described herein or a composition thereof.

In another embodiment, provided herein are methods for inducing an immune response in a subject comprising administering to the subject a glycoconjugate described herein or a composition thereof. In a specific embodiment, a method for inducing an immune response to a glycoconjugate described herein comprises administering to a subject in need thereof an effective amount of a bioconjugate described herein or a composition thereof.

In another embodiment, provided herein are methods for generating monoclonal antibodies to prevent infections using the bioconjugate described herein or a composition thereof.

In a specific embodiment, the subjects to whom a glycoconjugate or composition thereof is administered have, or are susceptible to, an infection, e.g., a bacterial infection. In another specific embodiment, the subjects to whom a bioconjugate or composition thereof is administered are infected with, or are susceptible to infection with *E. coli*.

6 EXAMPLES

6.1 Example 1: Strain Construction for *E. coli* O1 O Antigen Conjugate Production The first step to insertion is the cloning of the O1 rfb cluster into the donor plasmid pDOC by standard molecular cloning techniques [1]. The O1 rfb cluster region was cloned into plasmid pLAFR1 for to confirm activity (A, below) and in parallel into the donor plasmid pDOC for inserting the O1 cluster into the genome (B, below).

A. The O1 rfb cluster and its flanking 1.5 kb regions were subcloned into the cosmid vector pLAFR1 (GenBank. AY532632.1). The O1 cluster was amplified by PCR from chromosomal DNA of a clinical isolate named upecGVXN032 (StGVXN3736) using oligonucleotides 2193/2161 (see Table 3). Oligonucleotides 2193/2161 anneal in the genes flanking the O1 rfb cluster, namely in galF and after gnd. The PCR product was cloned into SgsI sites of p157. p157 is a pLAFR1 containing a cassette composed of two complementary oligonucleotides (300/301) which were cloned into the EcoRI site resulting in p947. Using p947 as a template, PCR was performed to amplify the O1 rfb cluster DNA from the flanking region at the 5' end (galF') to the end of the last gene (wekO) in the cluster using oligonucleotides 2198/2166 (see FIG. 3). The product was cloned into BamHI/SgsI sites of p967 resulting in p985. p967 was cloned from pDOC-C(GenBank. GQ889494.1) and contained an MCS and kanR cassette (for details see Section 6.2). p985 was used as template for PCR of the O1 rfb cluster for further insertion into p562 (see below).

Figure 3:
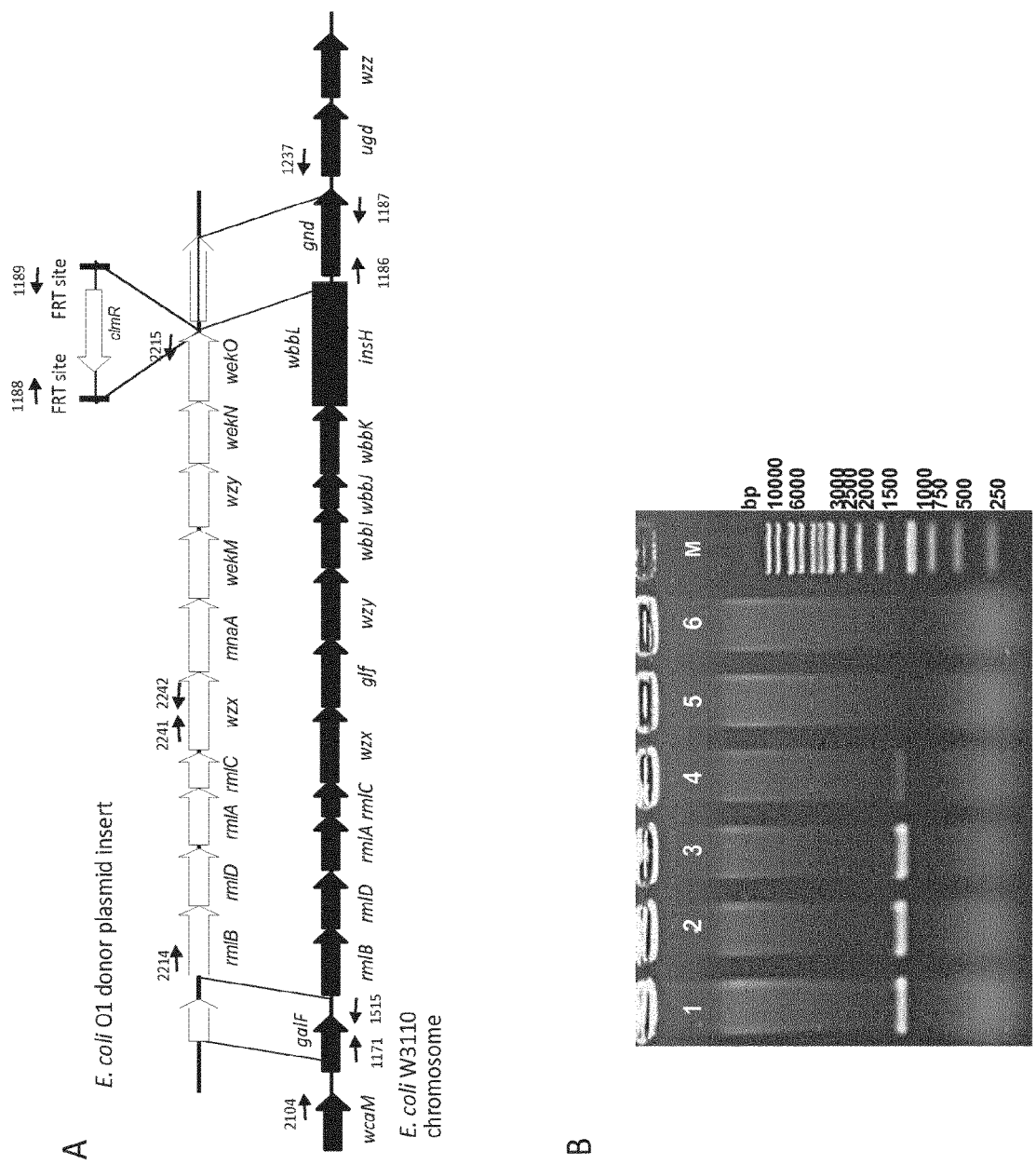

B. p562 was prepared as follows: an insert was generated resulting from an assembly PCR using two PCR products and oligonucleotides 1187/1188 (see Table 3). One PCR product was generated from pKD3 (GenBank: AY048742.1) using oligonucleotides 1188/1189 (see Table 3; encoding a clmR cassette and FRT sites) and another was the 3' homology region derived from PCR of W3110 genomic DNA with oligonucleotides 1186/1187 (see Table 3; i.e. DNA downstream of the O16 rfb cluster in the W3110 genome encoding the intergene region and the gnd gene). The assembled DNA was cut using BamHI/EcoRI and cloned into the same sites in pDOC-C, resulting in p482. A PCR product of the 5' homology region (encoding part of the galF gene indicated as galF', and the intergene region between galF and the first O16 gene) was then generated using W3110 chromosomal DNA and oligonucleotides 1171/1515, cut with BamHI and SpeI and cloned into the SpeI/BamHI sites of p482, resulting in p562.

p562 encodes the 5' and 3' homology regions (5': 1 kb upstream of rmlB of the O16 rfb cluster; 3': 1.6 kb downstream DNA of the last gene in the O16 rfb cluster) with an MCS and an inverted clmR resistance cassette in between. The MCS was used to insert the O1 rfb cluster amplified from p985 using oligonucleotides 2214/2215. The resulting plasmid p1003 was the donor plasmid for insertion of the O1 rfb cluster and contained the elements as illustrated in FIG. 3 A and Table 1.

Insertion and selection: the helper plasmid p999 (GenBank: GU327533.1) was introduced into W3110 cells by electroporation. Because of the temperature sensitive replication phenotype of p999, resulting cells were grown at 30° C. at all times in LB supplemented with spectinomycin for selection of p999. In a next step, p1003 was introduced into W3110 cells containing p999 by electroporation. Cells were selected for ampicillin and spectinomycin resistance in LB medium at 30° C. The plasmids were inserted into the acceptor cells to enable the expression of the enzymes encoded on the helper plasmid in the presence of the donor plasmid DNA within the same cell.

Next, the insertion procedure was performed. The freshly transformed strain was grown in LB medium in the presence of ampicillin and specticomycin at 30° C. at 5 ml scale overnight at 180 rpm. 10 μl of the dense culture was transferred to a new tube containing 1 ml LB supplemented with spec and amp. The new culture was then grown at 180 rpm for 2 hrs at 30° C., the cells were centrifuged at 5000 rpm for 5 minutes at 4° C., and the supernatant was replaced by LB medium supplemented with spec, 0.2% arabinose (w/v), and 1 mM IPTG. The media composition supports helper plasmid selection, and recombinase and SceI endonuclease expression to enable insertion. The cells were resuspended and further incubated at 30° C. for 4-18 hrs at 180 rpm.

At different time points after media change, 0.5 ml of the culture was plated on LB plates supplemented with clm (for selection of the DNA insert) and 10% (w/v) sucrose (to counterselect against the donor plasmid) and incubated at 37° C. overnight (to select for loss of the temperature sensitive helper plasmid).

To screen the resulting colonies for the correct insertion phenotype, the cells were replica plated onto LB plates supplemented with spec, amp, or clm. Colonies resistant to clm (for presence of the insert), but sensitive for amp and spec (for absence of the donor and helper plasmids) were further analyzed for the insertion.

To confirm that the strain lost the replaced DNA originating from W3110, and contained the DNA insert, colony PCR was performed. Candidate colonies with the correct phenotype (ampicillin sensitivity, chloramphenicol resistance, spectinomycin sensitivity, sucrose resistance) were picked and underwent a colony PCR test. A PCR strategy [51] was used for identification of O serotypes in extraintestinal E. coli (ExPEC) strains. Oligonucleotide pairs specific for unique gene sequences present in the rfb clusters of the 14 common ExPEC O serotypes were used. In the case of the O1 insertion, oligonucleotides amplifying parts of wzx from O1 (2241 and 2242) or O16 were used. Various clones were checked. Successful insertion was confirmed in some clones by absence of a PCR product with the O16 specific oligonucleotides (not shown), and presence of a specific signal with the O1 oligonucleotides (FIG. 3 B). The resulting strains were designated W3110 ΔrfbO16::rfbO1-clmR.

In a next step, the clmR cassette was removed from the DNA which was inserted along with the O1 rfb cluster by using the temperature sensitive pCP20 plasmid expressing the FLP recombinase as reported [35]. The resulting cells were tested for sensitivity to clm, and then further tested. The resulting strains were designated W3110 ΔrfbO16::rfbO1.

Furthermore, the O antigen ligase (waaL) from the production strain was deleted for optimal glycoconjugate production. This was performed by phage transduction. P1vir phage (E. coli genetic stock center #12133) was used to generate lysate from a W3110 ΔwaaL::clmR strain in which the waaL gene was replaced by a clmR cassette amplified by PCR from pKD3 using oligonucleotides 623 and 624)) [13, 52]. Phage transduction was performed on W3110 ΔrfbO16::rfbO1 and resulting strains were designated W3110 ΔrfbO16::rfbO1 ΔwaaL::clmR. Subsequently, the chloramphenicol resistant cassette was removed by FLP driven recombination (W3110 ΔrfbO16::rfbO1 ΔwaaL).

At every stage of recombinant engineering and selection, a PCR test for presence of the O1 wzx was performed to confirm the presence of the O1 rfb cluster (FIG. 3 B). Further PCR tests can be performed with oligonucleotides that specifically amplify the recombined regions at the 5' and 3' ends of the insertion, i.e. pairs that anneal outside the HR1 and 2 regions ('5' and 3' transition region PCR'). For example, one PCR oligonucleotide can be generated to anneal in the W3110 genome, and the other to anneal in the DNA insert. Thus, positive PCR signals are only possible if insertion is successful. Resulting PCR products can then be sequenced to confirm the ligation of chromosomal acceptor strain DNA and DNA insert. In addition, PCR and sequencing can be used to confirm the phage transduction and clmR cassette removal modifications.

To confirm the activity of the inserted DNA, the glycolipid production of the inserted strains containing the O1 antigen polysaccharide was tested at different stages of strain construction. Candidate clones from the initial insertion experiment were chosen according to positive results from the prescreening by antibiotics and sucrose sensitivity phenotype, and PCR tests. Cells were grown over night in LB medium and whole cell extracts were prepared. To analyze the glycolipids made, extracts were treated with proteinase K to remove possible interferences by proteins. The resulting samples were run on SDS PAGE and either stained by silver staining or detected by immunostaining using anti O1 specific antisera after transfer to nitrocellulose membranes. When extracts from putative integrands were analyzed by silver staining, a ladder like pattern between 25 to 55 kDa indicative of LPS was observed (FIG. 4 A, top panel, lanes 1, 2), as in the control strain (lane 3). The Western blotting showed ladder like signals at the same molecular weight range confirming that the LPS contained O1 antigen (FIG. 4 A, bottom, lanes 1, 2) like the control LPS which originates from a clinical O1 isolate (lane 3). These results confirm O1 antigen production displayed on lipid A in W3110 ΔrfbO16::rfbO1-clmR.

Figure 4:
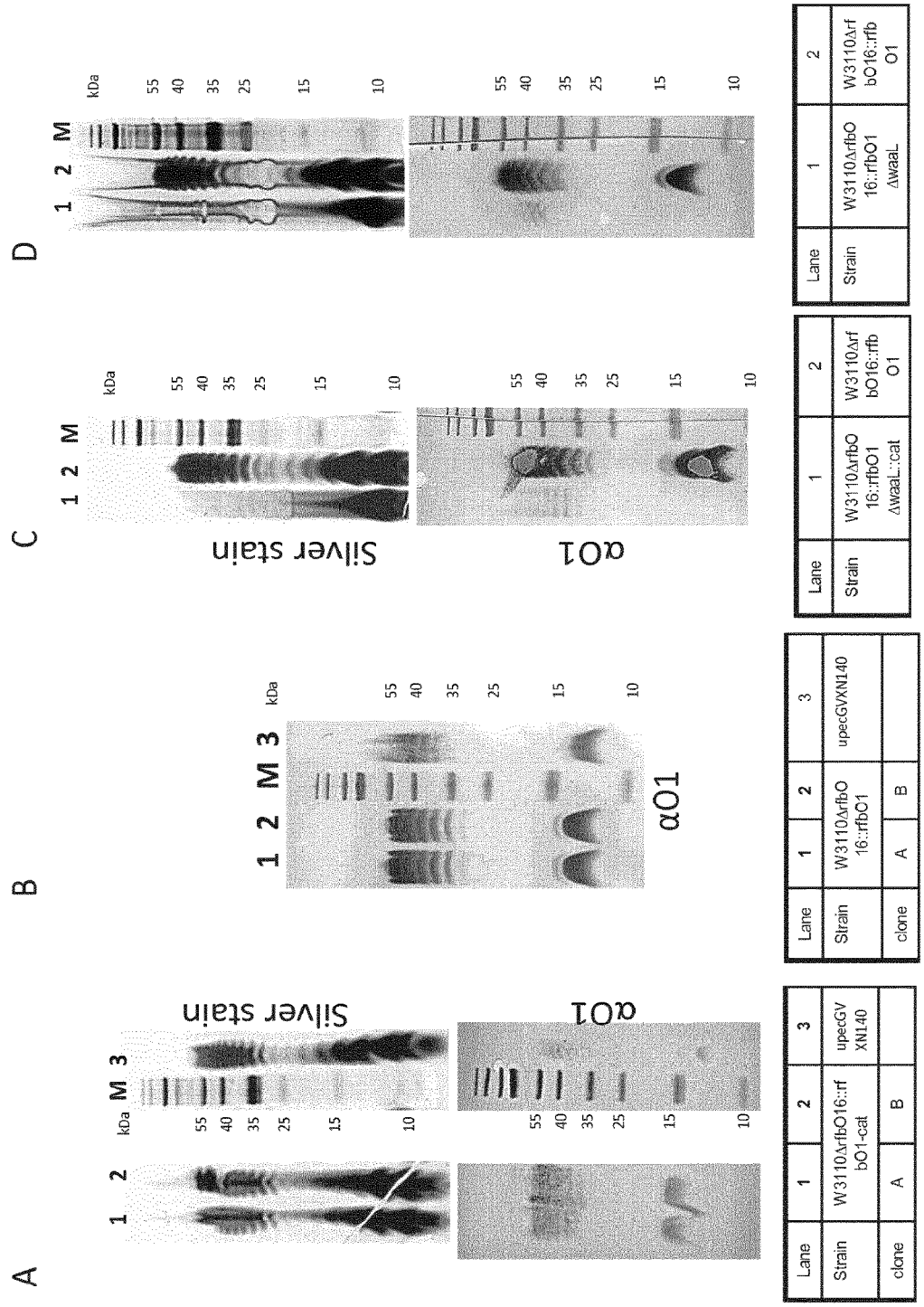

W3110 ΔrfbO16::rfbO1 strains were again tested (after removal of the clmR cassette) by Western blotting (FIG. 4 B, lanes 1, 2) to confirm the O1 LPS production in spite of the modification. To confirm the waaL deletion by phage transduction in strains W3110 ΔrfbO16::rfbO1 ΔwaaL::cat, LPS production was again analyzed (FIG. 4 C, lane 1). The ladder like signal disappeared from the silver staining assay (top) as expected. Western blot analysis still detected a ladder like signal (lane 1, bottom), albeit with lower intensity than the control strain (W3110 ΔrfbO16::rfbO1) which still contained the waaL gene (lane 2) and was able to make LPS as visualized by silver staining. The weaker signal originates from Und-PP linked O1 O antigen, which cannot be transferred to lipid A due to the deletion of the waaL gene. This means that waaL deletion by phage transduction occurred as expected, confirming the genotype W3110 ΔrfbO16::rfbO1 ΔwaaL::cat. Selected clones were chosen for clmR cassette removal in the same way as by the FLP borne recombination. Resulting clones (W3110 ΔrfbO16::rfbO1 ΔwaaL) were analyzed by silver staining and Western blotting (FIG. 4 D) and showed a comparable phenotype as observed in FIG. 4 D, lane 1.

The final strain W3110 ΔrfbO16::rfbO1 ΔwaaL was characterized by additional methods. To confirm the production of O antigen on Und-PP by those cells, a method was used that allows the molecular characterization of lipid linked oligosaccharides (Und-PP-linked O antigens) by fluorescent 2 AB labeling followed by HPLC and MS/MS. W3110 ΔrfbO16::rfbO1 ΔwaaL and a control strain (W3110 ΔwaaL) were grown over night in a shake flask at 37° C. Cells equivalent to an OD600 of 400 were harvested and washed once with 0.9% NaCl. The washed cell pellets were lyophilized. Lipids were extracted from the dried cells with 95% methanol (MeOH) by repeated rounds of vortexing and incubation on ice for 10 min. The suspension was converted into 85% MeOH by the addition of ddH$_2$O and further incubated for 10 min on ice while regularly vortexing. After centrifugation, the supernatant was collected and the extract was dried under N2. The dried lipids were dissolved in 1:1 (v/v) methanol/water (M/W) and subjected to a C18 SepPak cartridge (Waters Corp., Milford, MA). The cartridge was conditioned with 10 ml MeOH, followed by equilibration with 10 ml 10 mM TBAP in 1:1 M/W. After loading of the sample, the cartridge was washed with 10 ml 10 mM TBAP in 1:1 M/W and eluted with 5 ml MeOH followed by 5 ml 10:10:3 chloroform/methanol/water (C/M/W). The combined elutions were dried under $N_2$.

The lipid sample was hydrolyzed by dissolving the dried samples in 2 ml 1 M trifluoroacetic acid (TFA) in 50% n-propanol and heating to 50° C. for 15 min. The hydrolyzed sample was dried under $N_2$, dissolved in 4 ml 3:48:47 C/M/W and subjected to a C18 SepPak cartridge to separate the lipids from the hydrolyzed glycans. The cartridge was conditioned with 10 ml MeOH, followed by equilibration with 10 ml 3:48:47 C/M/W. The sample was applied to the cartridge and the flow through was collected. The cartridge was washed with 4 ml 3:48:47 C/M/W and the combined flow throughs were dried using a SpeedVac.

The dried samples were labeled with 2-aminobenzamide (2 AB) according to Bigge et al. [48]. The glycan cleanup was performed using the paper disk method as described in Merry et al. [53]. The separation of 2 AB labelled glycans was performed by HPLC using a GlycoSep N normal phase column according to Royle et al. [49], but modified to a three solvent system. Solvent A: 10 mM ammonium formate pH 4.4 in 80% acetonitrile. Solvent B: 30 mM ammonium formate pH 4.4 in 40% acetonitrile. Solvent C: 0.5% formic acid. The column temperature was 30° C. and 2 AB labelled glycans were detected by fluorescence (λex=330 nm, λem=420 nm). Gradient conditions: A linear gradient of 100% A to 100% B over 160 min at a flow rate of 0.4 ml min-1, followed by 2 min 100% B to 100% C, returing to 100% A over 2 min and running for 15 min at 100% A at a flow rate of 1 ml min-1, then returning the flow rate to 0.4 ml min-1 for 5 min. Samples were injected in $ddH_2O$.

Figure 5A:
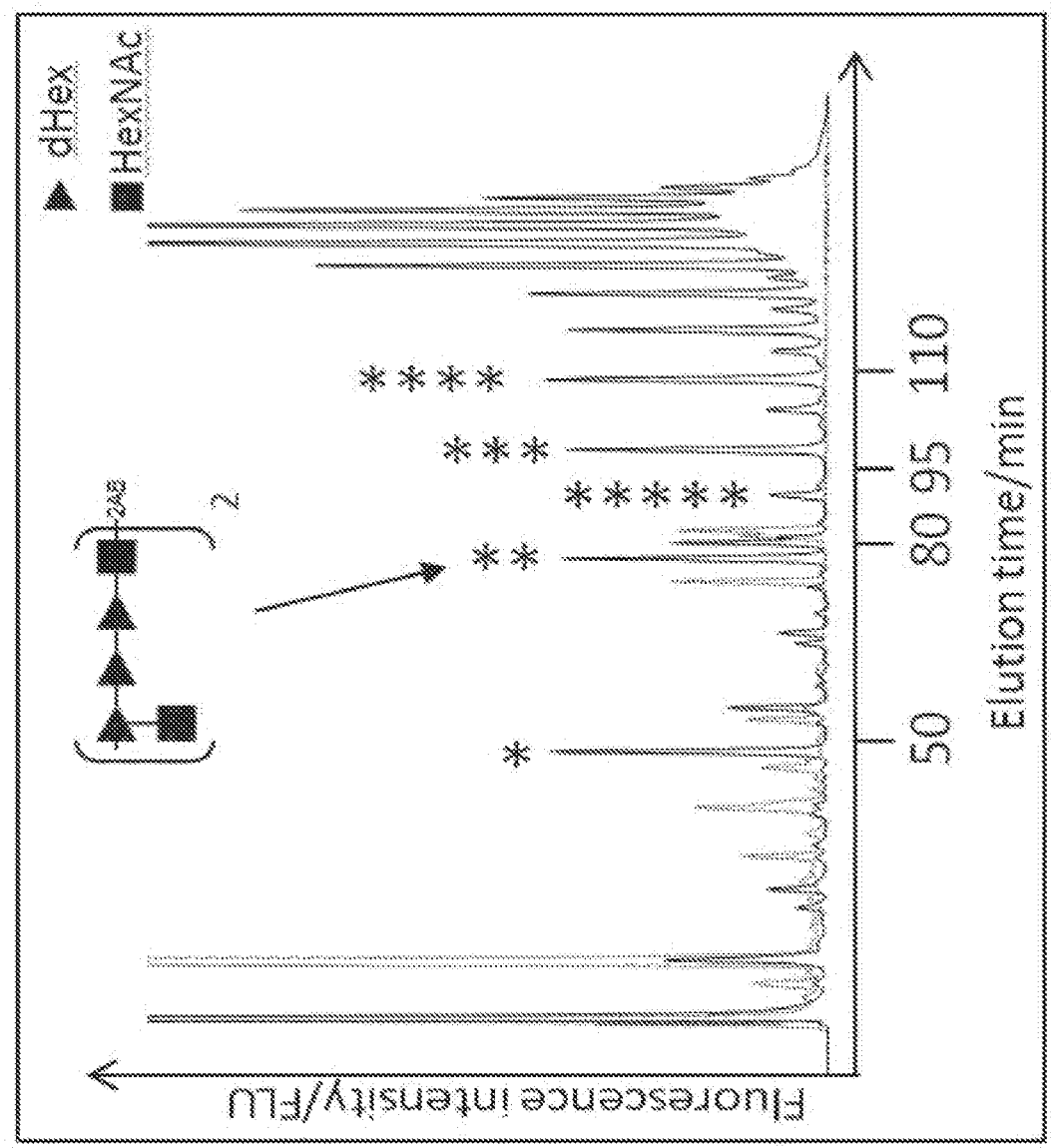
Figure 5B:
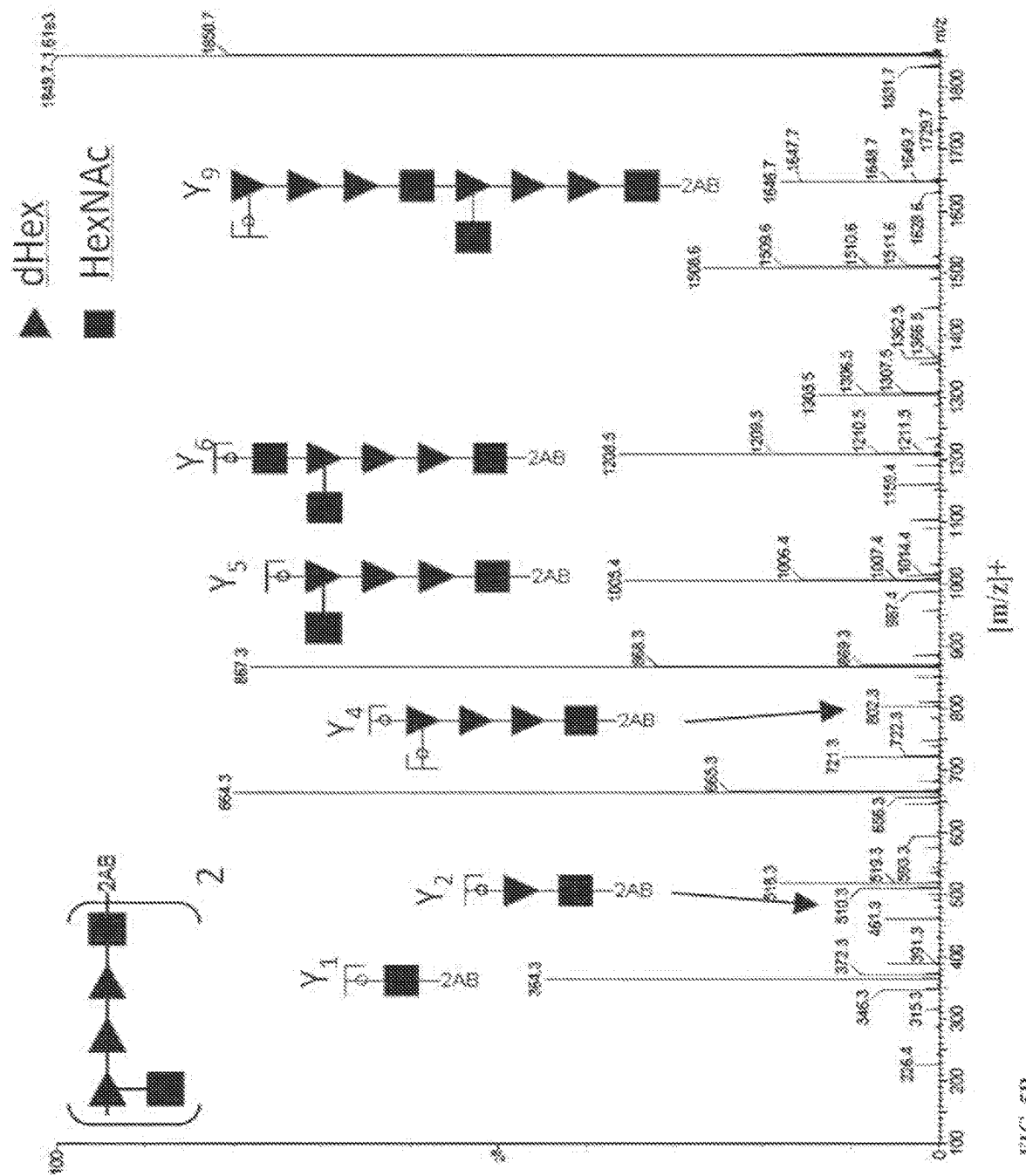

To identify O-antigen specific glycans, the 2 AB glycan profile from control cells was compared to the profile obtained from W3110 ΔrfbO16::rfbO1 ΔwaaL (FIG. 5 A). The W3110 ΔrfbO16::rfbO1 ΔwaaL specific peaks were collected and 2 AB glycans were analyzed on a MALDI SYNAPT HDMS Q-TOF system (Waters Corp., Milford, MA) (FIG. 5 B). Samples were dissolved in 5:95 acetonitrile/water and spotted 1:1 with 20 mg ml-1 DHB in 80:20 methanol/water. Calibration was done with PEG (Ready mixed solution, Waters Corp., Milford, MA), spotted with 1:3 with 5 mg ml-1 α-cyano-4-hydroxycinnamic acid (CHCA, Sigma-Aldrich, Switzerland) in 60:40:0.1 acetonitrile/water/trifluoroacetic acid. The instrument was equipped with 200 Hz solid state UV laser. Mass spectra were recorded in positive ion mode. For MSMS: laser energy was fixed at 240 at a firing rate of 200 Hz, collision gas was argon, a collision energy profile was used to ramp collision energy depending on the m/z. All spectra were combined, background subtracted, smoothed (Savitzsky Golay) and centred using MassLynx v4.0 software (Waters Corp., Milford, MA). The method is also described in US2011/0274720 A1.

Fragmentation ion series derived from several of the W3110 ΔrfbO16::rfbO1 ΔwaaL specific peaks (FIG. 5B) by MALDI-TOF/TOF analysis were consistent with the monosaccharide sequence reported for the O1A subserotype of *E. coli* [54]. Thereby the construction of an O1A O antigen producing W3110 based *E. coli* strain suitable for glycoconjugate formation was confirmed.

Figure 6:
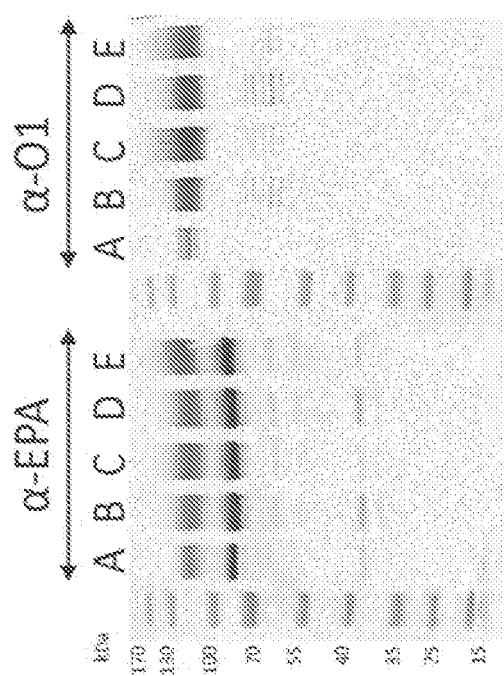

To show production of O1A glycoconjugate by this strain, plasmids encoding the inducible expression of the PglB oligosaccharyl transferase of *C. jejuni* (five different variants, see below) and the carrier protein Exotoxin A of *P. aeruginosa* (encoding 4 glycosylation consensus sequences, p659) were introduced by electroporation into W3110 ΔrfbO16::rfbO1 ΔwaaL. Production cells were inoculated into LB medium supplemented with 5 mM $MgCl_2$, spec and amp, and grown overnight at 37° C. into stationary phase. Cells were then diluted to an OD600 of 0.05 and grown until OD600 of 0.8 in TB containing spec and amp. EPA and PglB expression was initiated by the addition of 0.2% arabinose and 1 mM IPTG and the culture was grown for another 20 hrs. Cells were then harvested by centrifugation and periplasmic cell extracts were prepared using the Lysozyme method [55]. Periplasmic extracts (normalized to OD600) were separated by SDS PAGE and analyzed by immunoblotting after electrotransfer (FIG. 6). Detection with the anti EPA antiserum (left panel) and anti O1 antiserum (right panel) both show a clear ladder like pattern between 100 to 130 kDa for all samples, strongly indicative of glycoproteins consisting of the EPA protein and O1 polysaccharide. The signal obtained with the EPA antiserum alone (above 70 kDa) corresponds to unglycosylated EPA. It is evident that the different PglB variants lead to different specific productivities of glycoproteins: the smallest yield was obtained with the PglB corresponding to the original, wild type *C. jejuni* protein sequence containing a C terminal HA tag (p114, [9]). Codon optimization alone (p939), codon optimization and HA tag removal (p970), codon optimization and mutation of the natural PglB glycosylation site to N534Q (p948), and codon optimization, HA tag removal and removal of the natural PglB glycosylation site (p971), lead to stronger signals indicative of several fold higher yields. Higher yields may be explained by the more efficient ways of PglB translation when a codon optimized gene is used, and that the C terminal HA tag hampers activity or folding of the PglB protein.

Glycoproteins can be produced by the inserted strain in a bioreactor at 10 l scale for preparative purification of highly pure glycoconjugates exhibiting shorter glycan lengths as observed with a three plasmid system. Capillary gel electrophoresis can be used to analyze purity and size of the glycoconjugates. For example, polysaccharides attached to the glycoconjugates can be removed from the protein by hydrazinolysis and analyzed by 2 AB labeling and HPLC-MS/MS for analysis of the polysaccharide structure and length. Such analysis can be used confirm the attachment of O1A O antigen to the glycoprotein carrier. Furthermore, PMP analysis can be performed for monosaccharide composition determination, NMR analysis and gas chromatography for structure confirmation. In addition, immunization of animals can be performed to raise antibodies towards the glycan and the carrier protein. Anti-infective activity can be shown using preclinical assays, such as opsonophagocytic killing assays and/or passive protection.

Figure 7:
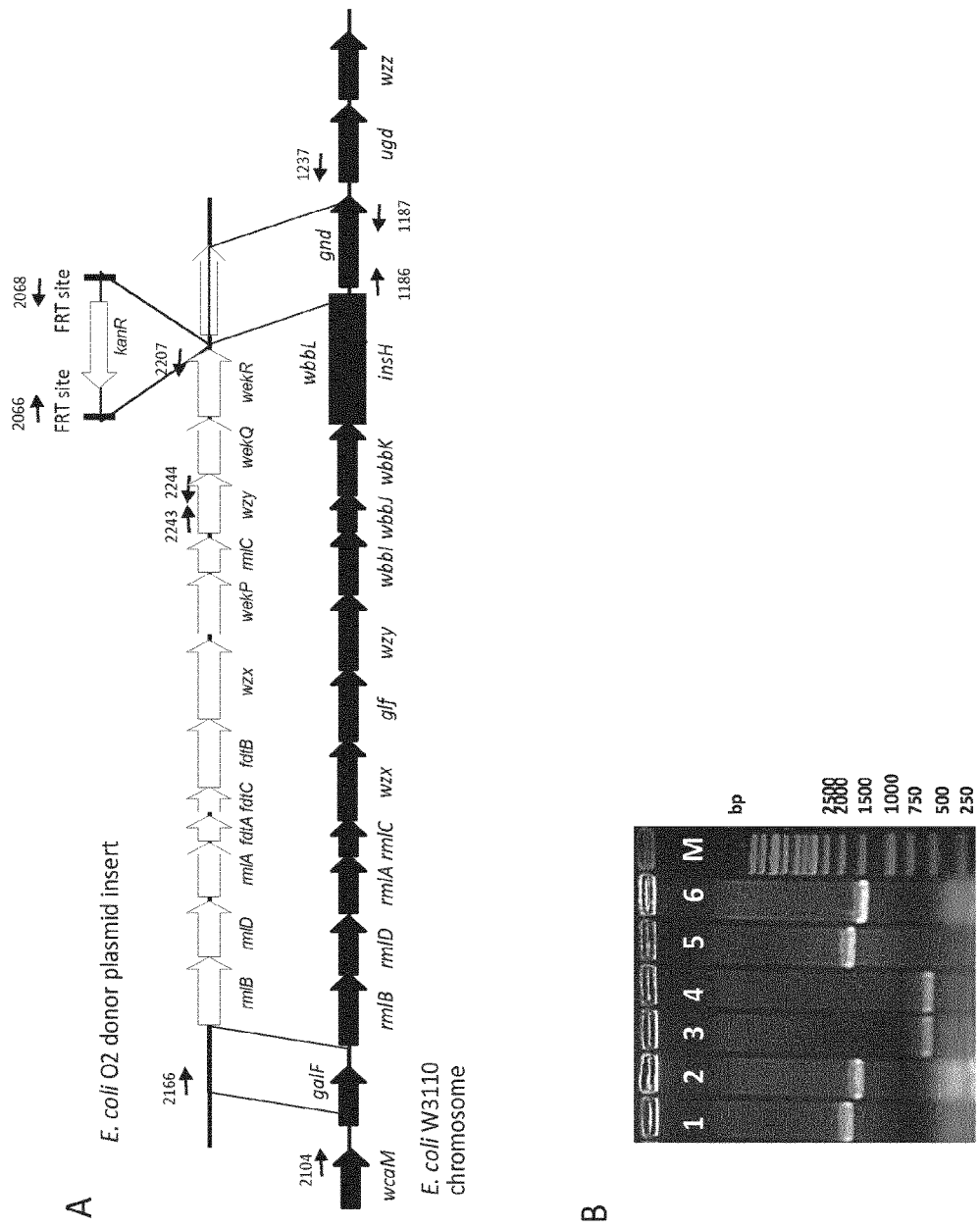

6.2 Example 2: Strain Construction for *E. coli* O2 O Antigen Conjugate Production Strain construction was performed similar to Example 1. The 02 rfb cluster was cloned in a pDOC plasmid consisting of the HR regions and a cassette as detailed in table 1. The O2 rfb cluster was amplified from clinical isolate upecGVXN116 (StGVXN3949) with oligos 2207/2166 and cloned into the BamHI/SgsI sites of p967. The O2 rfb amplicon contained all sequence from within galF until wekR. The DNA between wekR and gnd was omitted from the DNA insert. p967 was cloned by insertion of an oligocassette composed of two partially complementary oligonucleotides (2167/2168) into the XhoI and BamHI sites of p946. p946 was obtained by digesting p843 with AscI, treatment of the linearized plasmid with the Klenow fragment of DNA polymerase to fill up cohesive restriction site ends, and consecutive religation of the plasmid. p843 was generated by cloning a PCR amplicon derived from pKD4 [13] using oligonucleotides 2066 and 2068 (see Table 3) into the BamHI and SgsI sites of p482 using the same enzymes. The resulting donor plasmid p1003 contained the upstream HR1 region and the rfb cluster from the upecGVXN116, followed by a removable kanR cassette, and followed by the HR2 region (FIG. 7).

The p999 helper plasmid (GenBank: GU327533.1) was introduced into W3110 cells by electroporation [1]. 5-500 ng DNA in water were mixed with 50 µl electrocompetent cell suspension in a standard electroporation cuvette on ice and electroporated in a BioRad Micro Pulser (BioRad, Hercules, CA) at a voltage of 1.8 kV for 2-10 ms. Because of the temperature sensitive replication phenotype of p999, resulting cells were plated and grown at 30° C. at all times. In a next step, competent cells were made by growing W3110 containing p999 in LB supplemented with spectinomycin for selection of p999 at 30° C., and p1003 was introduced into the cells by electroporation, and cells were selected for ampicillin and spectinomycin resistance on LB plates at 30° C. The plasmids were inserted into the acceptor cells to enable the expression of the enzymes encoded on the helper plasmid in the presence of the donor plasmid DNA within the same cell.

The freshly transformed strain was grown in LB medium in the presence of ampicillin and specticomycin at 30° C. at 5 ml scale overnight at 180 rpm. 10 µl of the culture was transferred to a new tube containing 1 ml liquid LB supplemented with spec and amp. The new culture was then grown at 180 rpm for 2 hrs at 30° C. Then, the cells were centrifuged at 5000 rpm for 5 minutes at 4° C., the supernatant discarded and LB medium supplemented with spectinomycin, 0.2% arabinose (w/v), and 1 mM IPTG was added to support helper plasmid selection (Spec), and recombinase (arabinose) and SceI endonuclease (IPTG) expression. The resuspended cells were further incubated at 30° C. for 4-18 hrs at 180 rpm.

At different time points from 4 to 18 hrs after media change, the 0.5 ml of the culture was plated on LB supplemented with kan (for selection of the DNA insert) and 10% (w/v) sucrose (to counterselect against the donor plasmid) and incubated at 37° C. overnight (to select for loss of the temperature sensitive helper plasmid).

To screen the resulting colonies for the correct insertion phenotype, the cells were replica plated onto LB plates supplemented with spec, amp, or kan. Colonies resistant to kan (for presence of the insert), but sensitive for amp and spec (for absence of the donor and helper plasmids) were further analyzed for the insertion.

In a next step, the waaL gene was disrupted by phage transduction as described above. The resulting strain from phage transduction was selected for clm (waaL deletion) and kan (O2 rfb cluster insertion) resistance, resulting in the genotype W3110 ΔrfbO16::rfbO2-kanR ΔwaaL::cat.

Antibiotic resistance cassettes for kan (from the rfb cluster insertion) and clm (waaL deletion) were removed in a single step by FLP recombinase driven recombination using pCP20 as described [35].

Insertion of the DNA insert was tested by PCR for absence of O16 wzx and presence of O2 wzy using previously published oligonucleotides 2243 and 2244 (FIG. 7 A). [51]. Further analysis can include 5' and 3' transition region PCR and sequencing. waaL deletion was tested by a colony PCR approach using oligonucleotides 1114 and 1326 (see Table 3) that anneal in the DNA region flanking the waaL gene (FIG. 7B). A PCR product is larger than 1.5 kb with these oligonucleotides when an intact waaL copy is present (in lanes 1 and 5), slightly smaller (below 1.5 kb, lanes 2 and 6) if waaL is replaced by clmR cassette, and after removal of the clmR cassette the PCR amplicon is about 0.5 kb in size (FIG. 7 B). Accordingly, the waaL deletion was successful. The final strain (W3110 ΔrfbO16::rfbO2 ΔwaaL) can be tested by 5' and 3' transition region PCR.

Figure 8:
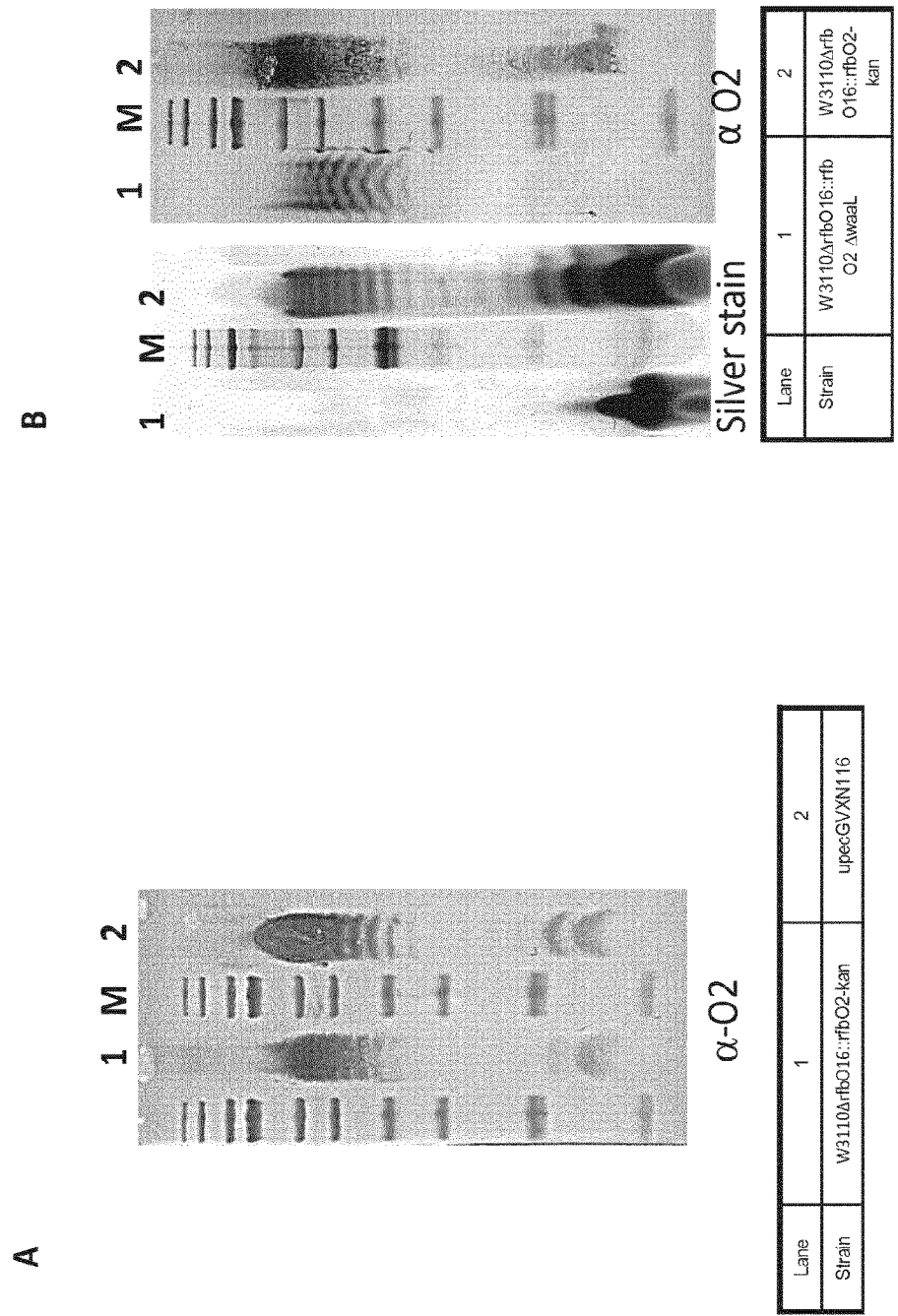

Silver stain and Western blot analysis using O2 typing sera of LPS samples was used to confirm the O antigen production phenotypes during strain construction (FIG. 8). When probed with anti O2 antiserum, a ladder was detected in extracts from the putative integrant (W3110 ΔrfbO16:: O2-kanR, A, lane 1) as well as in the positive control strain, a clinical E. coli O2 isolate (lane 2). This suggested that the integrand contained an active O2 rfb cluster. The final strain (W3110 ΔrfbO16::rfbO2 ΔwaaL) was tested for LPS and Und-PPO antigen production by silver staining (FIG. 8 B, left panel), and Western blot (FIG. 8 B, right panel). Whereas the waaL positive strain produced LPS as visualized by silver staining with a ladder like signal (lane 2), the signal was absent after waaL deletion and antibiotics cassettes removal (lane 1). Western blotting (panel B) showed a ladder like pattern in both samples, albeit with much lower intensity in the waaL deleted strain. This indicates that indeed the waaL deleted strain produced Und-PP linked O2 reactive polysaccharide.

Figure 9A:
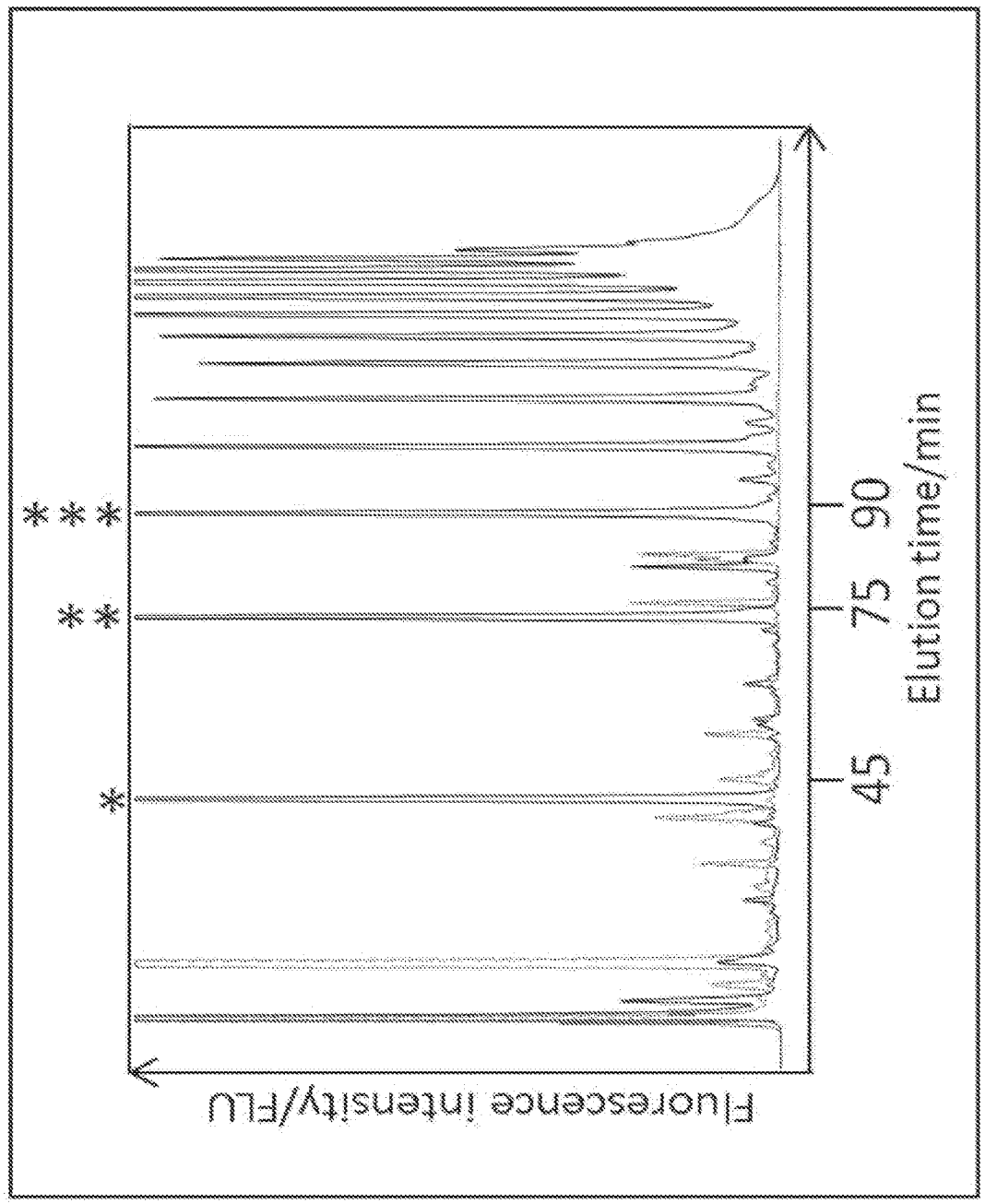
Figure 9B:
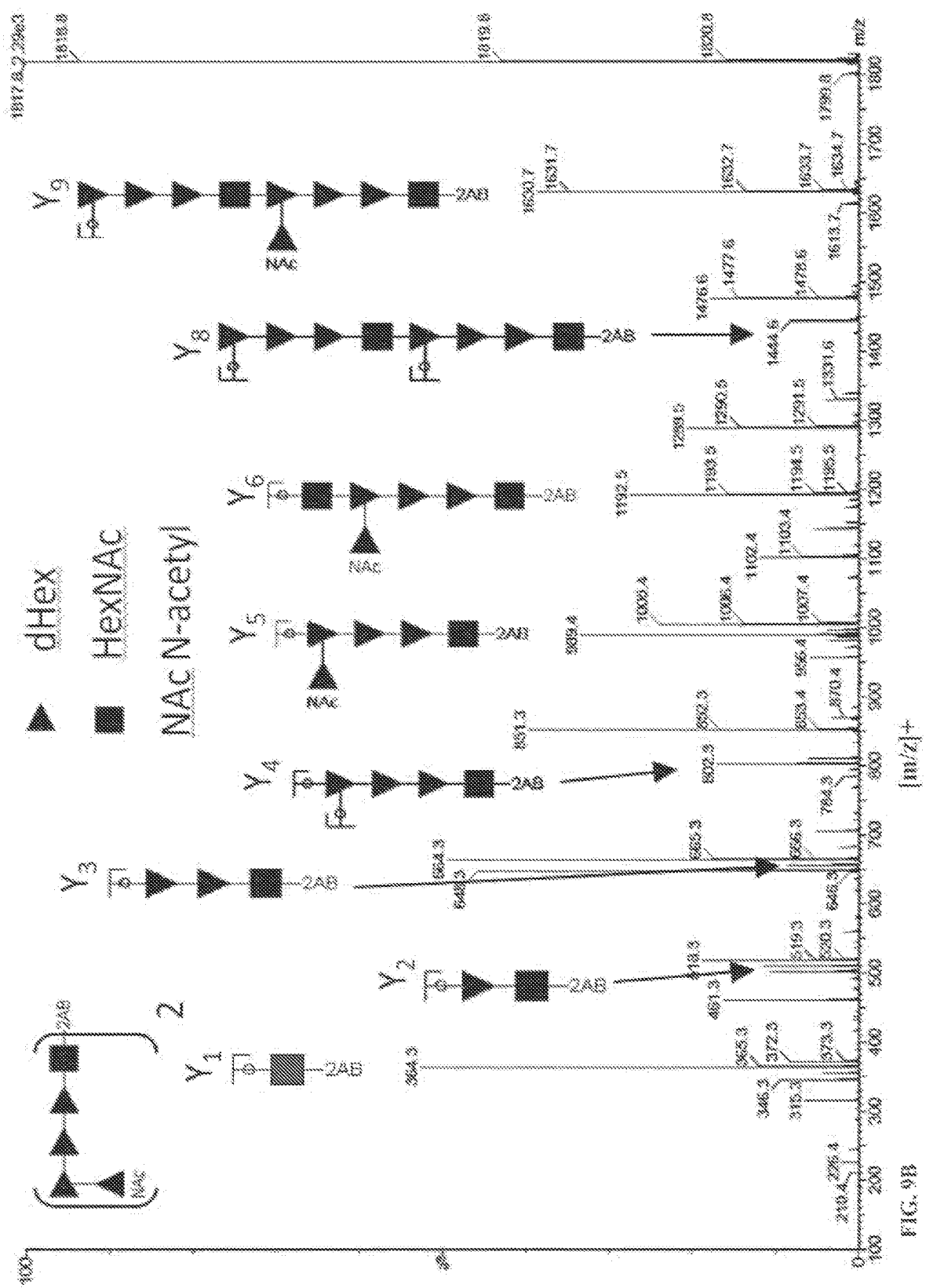

To confirm the production of O antigen on Und-PP by those cells, the 2 AB labeling methods as described above (section 6.2) were used. Signals specific for W3110 ΔrfbO16::rfbO2 ΔwaaL were observed when the fluorescent traces were compared to a strain that is unable to produce O antigen. Specific peak elution times were consistent with previously identified O2 repeat units as analyzed by MALDI MS/MS (FIG. 9 A). Fragmentation ion series from several collected peaks were analyzed by MALDI-TOF/TOF as described above. Fragmentation patterns are consistent with the O2 O antigen repeat unit (FIG. 9 B). Thereby the construction of an O2 O antigen producing W3110 based E. coli strain W3110 ΔrfbO16::rfbO2 ΔwaaL was confirmed.

Figure 10:
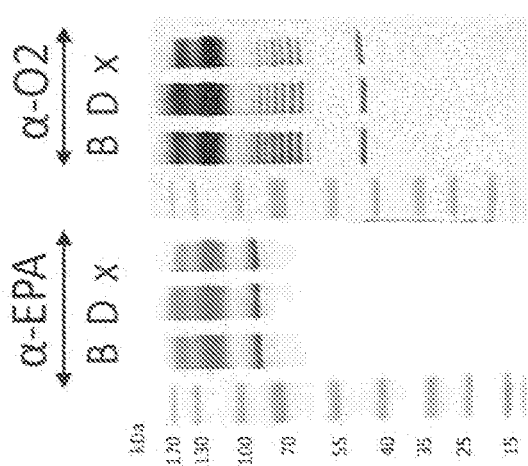

To show production of O2 glycoconjugate by W3110 ΔrfbO16::rfbO2 ΔwaaL, plasmids for inducible expression of the PglB oligosaccharyl transferase of C. jejuni (two different variants) and the carrier protein EPA (encoding 4 glycosylation consensus sequences, p659) were introduced into W3110 ΔrfbO16::rfbO2 ΔwaaL by electroporation. Cells were inoculated into LB medium supplemented with 5 mM $MgCl_2$, spec and amp, and grown overnight at 37° C. into stationary phase. Cells were then diluted to an $OD_{600}$ of 0.05 and grown until $OD_{600}$ of 0.8 in TB containing spec and amp. EPA and PglB expression was initiated by the addition of 0.2% arabinose and 1 mM IPTG and the culture was grown for another 20 hrs. Cells were then harvested by centrifugation and periplasmic cell extracts were prepared using the Lysozyme method [55]. Periplasmic extracts (normalized to cell density) were separated by SDS PAGE and analyzed by western blotting (FIG. 10). Detection with the anti EPA antiserum (left panel) and anti O2 antiserum (right panel) both show two clusters of the typical O antigen ladder like pattern above 100 kDa, strongly indicative of glycoproteins consisting of the EPA protein and O2 polysaccharide. The signal obtained with the EPA antiserum alone (above 70 kDa) corresponds to unglycosylated EPA. The first cluster (between 100 and 130 kDa) corresponds to singly, the second, weaker cluster (above 130 kDa) to doubly glycosylated EPA protein. Ladder like signals observed in the anti O2 western blot are most probably degradation products of the EPA O2 glycoconjugate which still contain the polysaccharide portion. It is evident that both PglB variants lead to similar specific productivities of glycoproteins. upecGVXN124 (StGVXN3947) is a clinical O2 serotype isolate, in which the waaL gene was deleted [13] and plasmids p659 and p939 were introduced into it by electroporation. Using this control expression system as a comparator (lane x), stronger signals were observed from extracts derived from W3110 ΔrfbO16::rfbO2 ΔwaaL (lane B) than from the expression system using a clinical isolate (upecGVXN124) as expression host. Thus, insertion in W3110 can result in higher yields of glycoconjugates as compared to glycosylation in the natural strain.

Glycoproteins also can be produced by the inserted strain in a bioreactor at 10 l scale for preparative purification of highly pure glycoconjugates exhibiting shorter glycan lengths as observed with a three plasmid system. Capillary gel electrophoresis can be used to analyze purity, amount and size of the glycoconjugates. Polysaccharides attached to the glycoconjugates can be removed from the protein by hydrazinolysis and analyzed by 2 AB labeling and HPLC-MS/MS for analysis of the polysaccharide structure and length. This analysis can be used to confirm the attachment of the O2 O antigen to the glycoprotein carrier. Furthermore, PMP analysis can be performed for monosaccharide composition determination, NMR analysis and gas chromatography for structure confirmation. Further, immunization of animals can be performed to raise antibodies towards the glycan and the carrier protein. Anti-infective activity can be shown by using assays such as opsonophagocytotic killing assays and/or passive protection.

6.3 Example 3: Strain Construction for E. coli O6 O Antigen Conjugate Production Strain construction was performed as described above. The O6 rfb cluster was cloned in a pDOC plasmid consisting of the HR regions and a kanR cassette as detailed in table 1. The O6 cluster was amplified from genomic DNA from E. coli strain CCUG11309 with oligonucleotides 1907/1908 (FIG. 11 A) and cloned into the BamHI and BcuI sites of p843 resulting in p914.

The p999 helper plasmid (GenBank: GU327533.1) was introduced into W3110 cells by electroporation [1]. 5-500 ng DNA in water were mixed with 50 μl electrocompetent cell suspension in a standard electroporation cuvette on ice and electroporated in a BioRad Micro Pulser (BioRad) at a voltage of 1.8 kV for 2-10 ms. Because of the temperature sensitive replication phenotype of p999, resulting cells were plated and grown at 30° C. at all times. In a next step, p914 was introduced into W3110 bearing p999 by electroporation, and cells were selected for amp and spec resistance on LB plates at 30° C. The plasmids were inserted into the acceptor cells to enable the expression of the enzymes encoded on the helper plasmid in the presence of the donor plasmid DNA within the same cell.

Electroporated clones containing helper and donor plasmids were grown in LB medium in the presence of amp and spec at 30° C. at 5 ml scale overnight at 180 rpm. 10 μl of the culture was transferred to a new tube containing 1 ml liquid LB supplemented with spec and amp. The new culture was then grown at 180 rpm for 2 hrs at 30° C. Then, the medium was exchanged: the culture was centrifuged at 5000 rpm for 5 minutes at 4° C., the supernatant discarded and the cell pellet was resuspended in LB medium supplemented with spec, 0.2% arabinose (w/v), and 1 mM IPTG to support helper plasmid selection (Spec), and recombinase (ara) and SceI endonuclease (IPTG) expression. The resuspended cells were further incubated at 30° C. for 4-18 hrs at 180 rpm to allow for the recombination event to occur.

At different time points from 4 to 18 hrs after media change, the 0.5 ml of the culture was plated on LB supplemented with kan (for selection of the DNA insert) and 10% (w/v) sucrose (to counter select against the donor plasmid) and incubated at 37° C. overnight (to select for loss of the temperature sensitive helper plasmid).

To screen the resulting colonies for the correct insertion phenotype (W3110 ΔrfbO16::rfbO6-kanR), the cells were replica plated onto LB plates supplemented with spec, amp, or kan. Colonies resistant to kan (for presence of the DNA insert), but sensitive for amp and spec (for absence of the donor and helper plasmids) were further analyzed for the insertion. In addition, colony blotting was performed. Replica plated colonies grown on LB supplemented with kan were transferred to a nitrocellulose membrane by 'colony lifting': a round nitrocellulose membrane was laid on the LB plate on top of the growing colonies until the membrane was completely wet. Upon lifting the membrane, the colonies sticking to the membrane are washed away in PBS supplemented with Tween 20 (0.02% w/v). Thereafter, the membrane was processed as a western blot using the anti O6 antiserum for detection of colonies that produced the O6 antigen. Positive colonies appeared as dark dots after development of the membranes.

Antibiotic resistance cassettes for kan (from the rfb cluster insertion) and clm (waaL deletion) were removed in a single step by FLP recombinase driven recombination using plasmid pCP20 as described [35].

Figure 11:
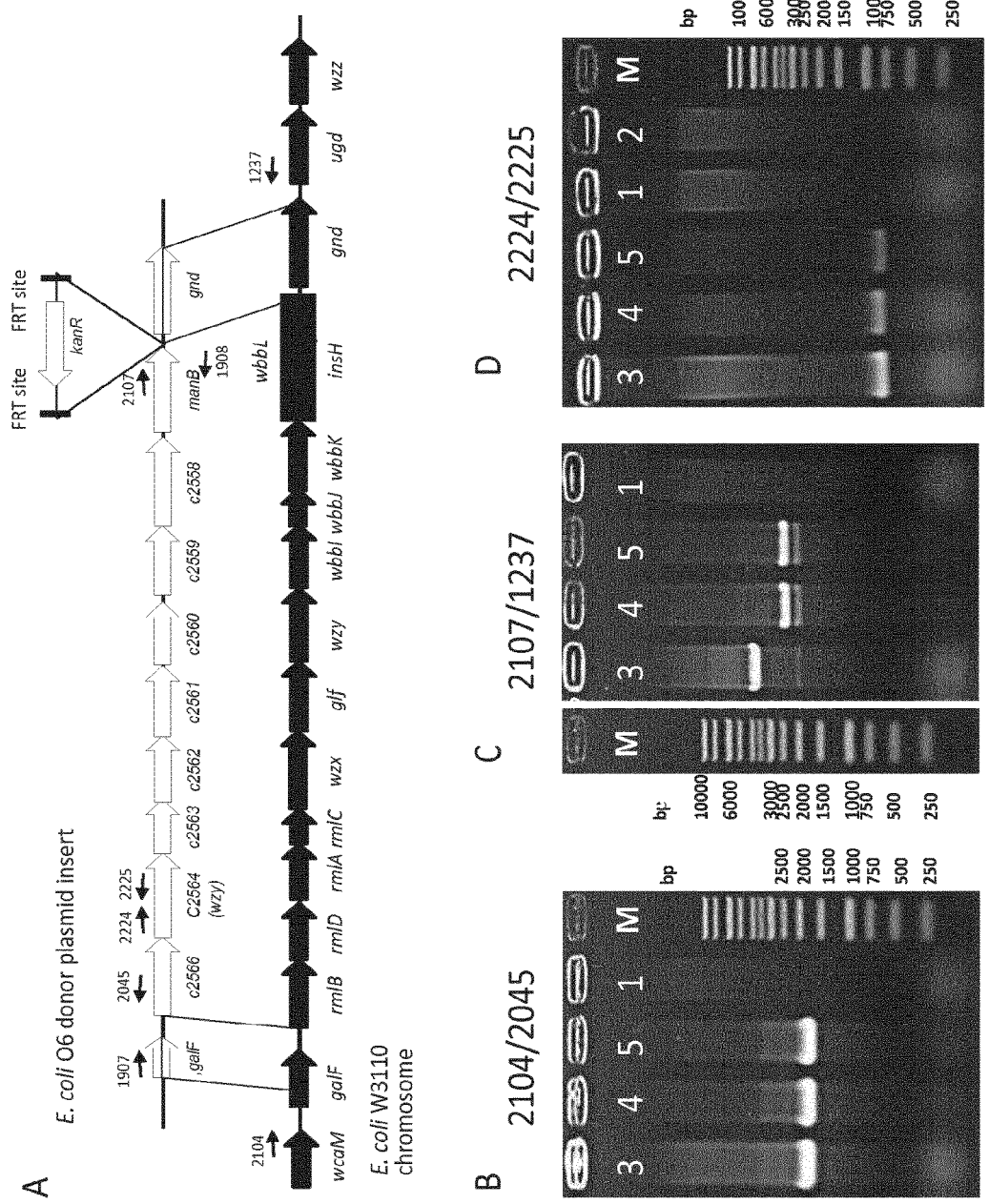
Figure 12:
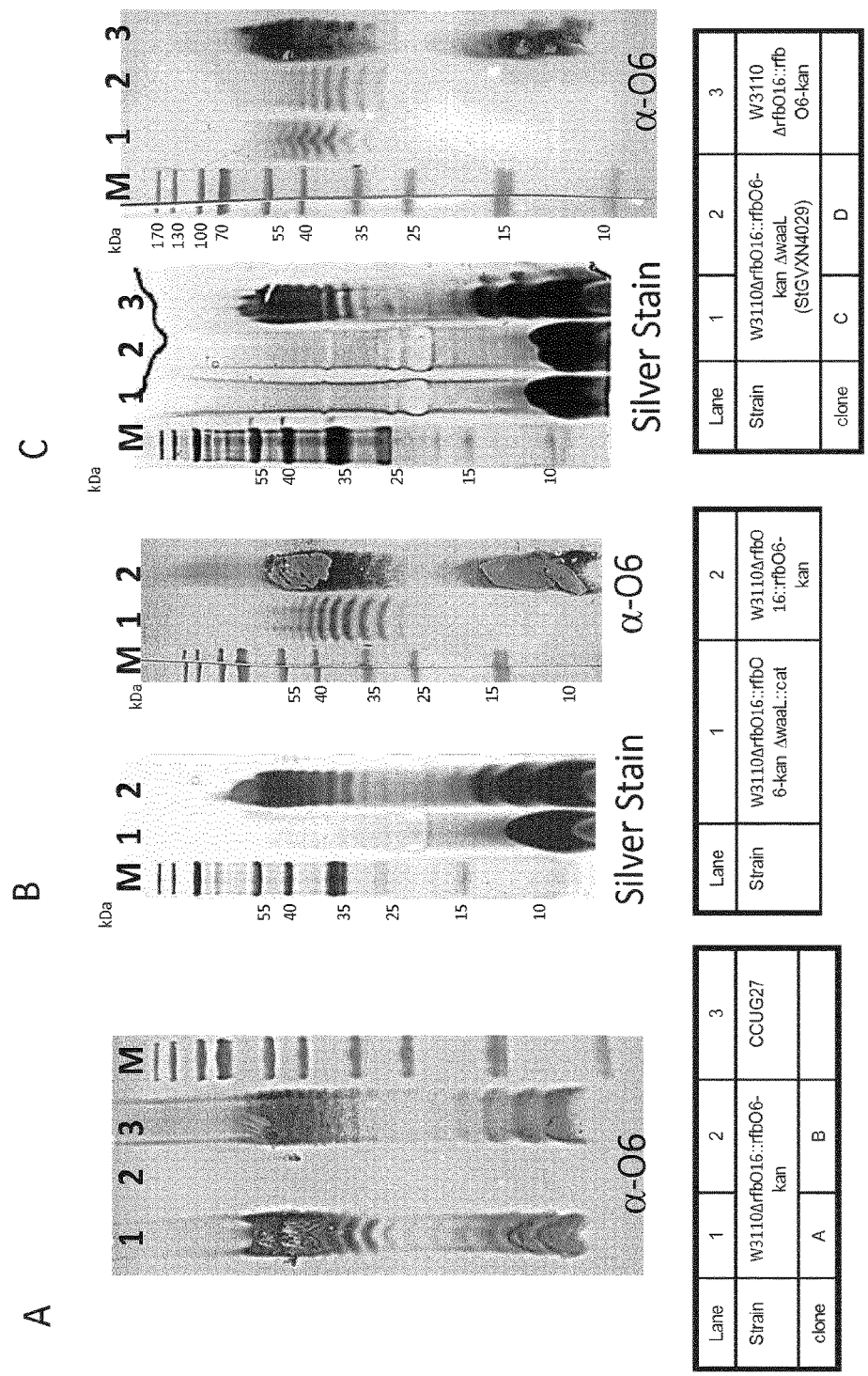

Insertion of the DNA insert was tested by PCR for absence of O16 wzx and presence of O6 wzy [51] (FIG. 11 D), by 5' (FIG. 11 B) and 3' (FIG. 11 C) transition region PCR, silver stain of LPS samples, and western blot analysis using O6 typing sera (FIG. 12). Only clone A (FIG. 12A, lane 1) made a ladder like O antigen signal when extracts were analyzed with anti O6 serum (like the E. coli O6 control strain, lane 3), whereas clone B was negative (lane 2). All further tests were positive for the functional activity of the rfb cluster.

In a next step, the waaL gene was disrupted by phage transduction from clone A as described above [52]. Silver staining shows that O antigen is absent from a waaL deletion strain (FIG. 12 B, left panel, lane 1), and western analysis shows Und-PP linked O6 O antigen as a typical weak ladder like signal in the same extracts (FIG. 12 B, right panel, lane 1). Before waaL deletion, LPS is clearly observed (both panels, lanes 2). This result showed successful waaL deletion.

The antibiotic resistance cassettes for clm (waaL deletion), and then for kan (rfb cluster insertion) were removed in two consecutive steps by FLP recombination [35]. FIG. 12 C shows two clones (lanes 1, 2) after clmR removal with remaining Und-PP linked signals (western blot, right panel). The final strains (two clones, W3110 ΔrfbO16::rfbO6 ΔwaaL) were tested by 5' and 3' transition region PCR (FIGS. 11 A and B). Silver stain of LPS, western blot, and fluorescent 2 AB labeling followed by HPLC and MS/MS analysis of Und-PP-linked polysaccharides can be done to confirm. All data can confirm the successful insertion, and functional activity of the rfb cluster in the both of the selected clones.

Figure 13:
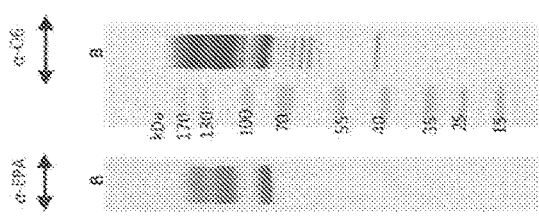

To show production of O6 glycoconjugate, plasmids providing inducible expression of the PglB oligosaccharyl transferase of C. jejuni (p939) and the carrier protein EPA (encoding 4 glycosylation consensus sequences, p659) were introduced into W3110 ΔrfbO16::rfbO6-kanR ΔwaaL (i.e.

the ancestor of the final strain W3110 ΔrfbO16::rfbO6 ΔwaaL) by electroporation. Cells were grown and inducers were added, and the cells further grown over night. Samples were collected and periplasmic cell extracts were prepared using the Lysozyme method [55]. Periplasmic extracts (normalized to cell density) were separated by SDS PAGE and analyzed by immunoblotting after electrotransfer. Detection with the anti EPA antiserum and anti O6 antiserum both show two clear cluster of ladder like signals, one between 100 and 130, and one above 130 kDa (FIG. 13). These signals are strongly indicative of glycoproteins consisting of the EPA protein and O6 polysaccharide. The signal obtained with the EPA antiserum alone (above 70 kDa) corresponds to unglycosylated EPA. It is evident that two ladder clusters are detected, indicative of EPA glycosylated at two sites.

Glycoproteins can also be produced by the inserted strain in a bioreactor at 10 l scale for preparative purification of glycoconjugates. Polysaccharides attached to the glycoconjugates can be removed from the protein by hydrazinolysis and analyzed by 2 AB labeling and HPLC-MS/MS as Und-PP linked O antigen. This analysis can confirm the attachment of O6 antigen to the glycoprotein carrier.

To analyze the inserted strains in terms of quality and quantity of conjugate production, the performance of inserted strains for O1, O2, and O6 EPA glycoconjugate production to alternative production systems was compared, which are the "three plasmid systems", i.e. systems with the rfb cluster encoded on an episome as described in the prior art [9], or the "wildtype strain" system. In the former, a W3110 ΔwaaL strain is used as an expression host. There are some technical differences in that system compared to the inserted and wildtype systems. The three plasmid system requires the introduction and maintenance of three plasmids in the host. This means that three different antibiotics have to be added to the growth media during fermentation to ensure plasmid maintenance. Coexistence of three plasmids requires compatible vector backbones. Especially the large rfb cluster sequences require a specified maintenance system and intense selection pressure. Plasmid maintenance is a permanent cause for reduced yields in production processes for recombinant microbial fermentation products, mainly because plasmid loss occurs, and thus the affected cells stop producing the recombinant product, or because plasmid maintenance implies such a burden to the cell that yields drop. Due to potential allergic adverse events of humans to antibiotics, there is an increasing request of regulatory agencies for antibiotics free production processes. Thus, there is a clear advantage in integrating the biosynthetic cluster formerly present on an episome to the chromosome.

The second possible production system is based on natural, clinical isolates derived from infected individuals or from the field, and using them as production platforms. As they naturally produce the O antigen of interest, a simple waaL deletion makes those strains suitable, naturally inserted production strains. However, since many toxins and factors encoded and expressed in E. coli clinical isolates, regulatory agencies require higher quality standards for products from such systems, which is pricey and time consuming. Thus, the insertion into the well studied and safe host W3110 represents a suitable alternative: plasmid associated disadvantages are reduced, and economical requirements are fulfilled.

Figure 14:
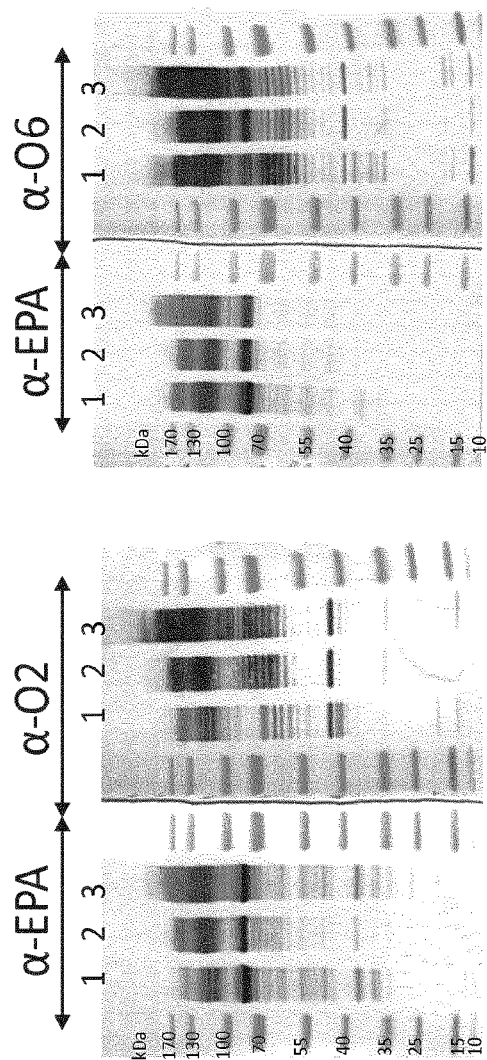

We analyzed all three production systems for all three E. coli O antigens (FIG. 14). Expression plasmids for EPA (p659) and PglB (p939) were introduced into host cells containing the rfb locus either in the genome (inserted strains or clinical isolates) or on a plasmid (three plasmid system). Bacterial cultures were first grown overnight in LB medium containing all the antibiotics necessary to maintain the plasmids present in the cells. Then, the culture was diluted to OD600 of 0.05 in TB medium and grown until OD600 of 0.4-1.2 and inducers were added (arabinose 0.2%, IPTG 1 mM). 20 hrs after induction at 37° C., the cells were harvested and periplasmic extracts were prepared using the lysozyme method. Periplasmic lysates were then analyzed by SDS PAGE and immunodetection (western blot).

Unglycosylated EPA is observed above 70 kDa in the anti-EPA blots. Ladder like patterns clustered above 100 kDa represent full length glycoconjugates with the typical O antigen polysaccharide length distribution. Generally, all systems produce glycoconjugates in a similar order of magnitude. However, the three plasmid systems produce ladder like signals in anti EPA and anti polysaccharide Western blots which appear more widely spread (FIG. 14, panel A, compare lane 3 and 2) or reaching higher molecular weight levels (all panels, compare lanes 3 and 2) than the inserted strains (wild type and inserted). This shows that the insertion strategy is a powerful process adjustment tool for glycoconjugate production (FIG. 14).

Preclinical comparisons of the long polysaccharide glycoconjugates (made by the three plasmid system) and the inserted strains can be performed to determine whether the latter conjugates are more immunogenic and more defined.

Comparison of the culture homogeneity and maintenance of the recombinant DNA elements in production cultures can be performed to show that cells from inserted host strains are capable of producing higher levels of product, exhibit a better reproducibility pattern and that they are genetically more stable, thus confirming that insertion is superior due to the high feasibility of upscaling.

6.4 Example 4: Strain Construction for S. sonnei O Antigen Production

Figure 16:
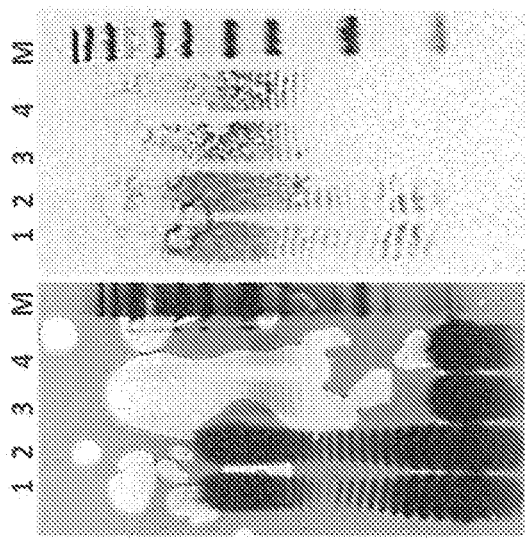

The P. shigelloides O17 cluster is functionally identical to the S. sonnei rfb cluster but not encoded on an unstable pathogenicity plasmid and was thus cloned from P. shigelloides. The cluster was amplified from genomic DNA from P. shigelloides O17 with oligonucleotides 1508/1509 (without wzz) and 1528/1509 (with wzz). The rfb cluster of P. shigelloides O17 was cloned into the pDOC-derived plasmid p562 resulting in p563 (in which wzz was included) and p568 (lacking the wzz gene). The helper plasmids consisted of the HR regions and a selection cassette as detailed in Table 1. Strain construction was performed as described in Example 1. Insertion of the DNA insert was tested by PCR for absence of O16 wzy and presence of S. sonnei wzy-wbgV, by 5' and 3' transition region PCR (FIG. 15), silver stain of LPS samples, and Western blot analysis using S. sonnei typing sera (FIG. 16).

Figure 17:
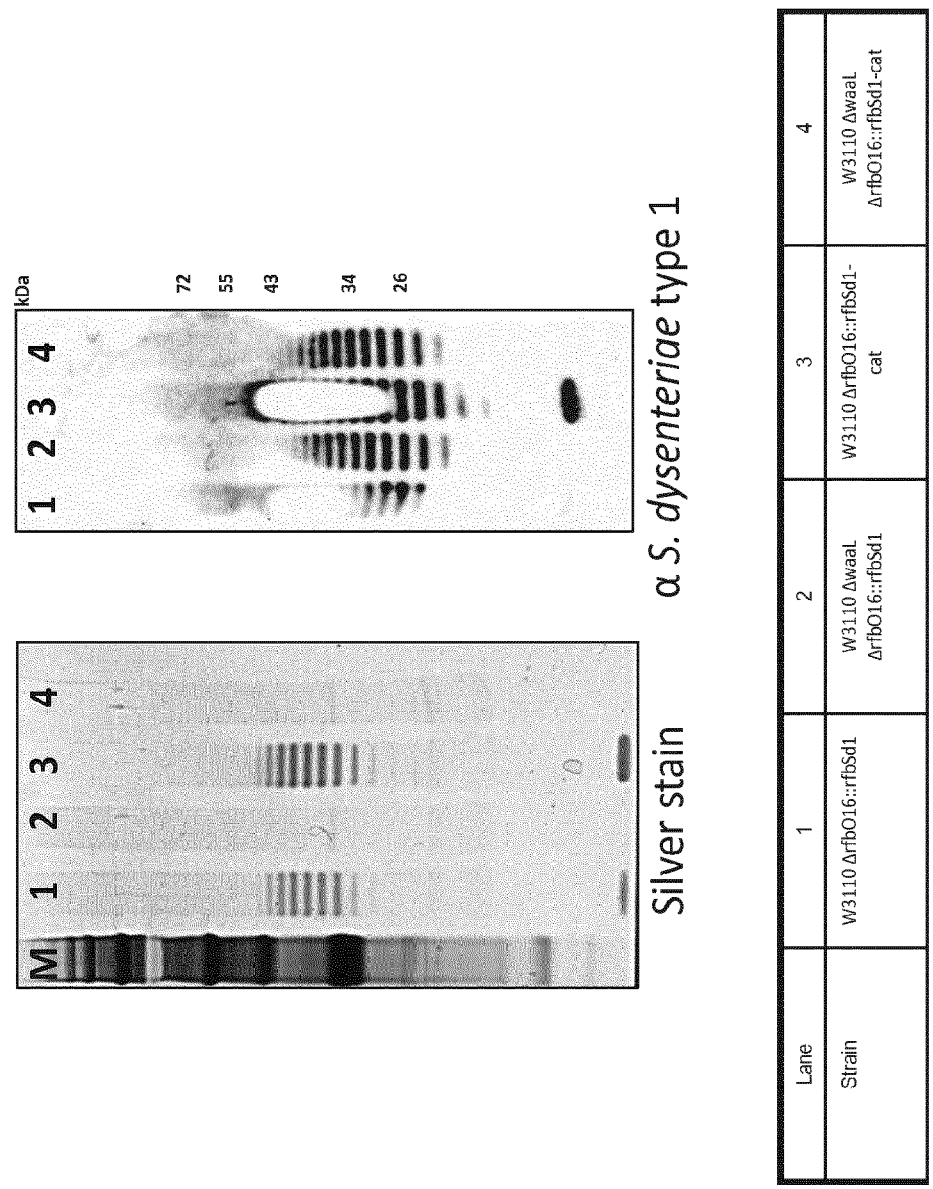
Figure 18A:
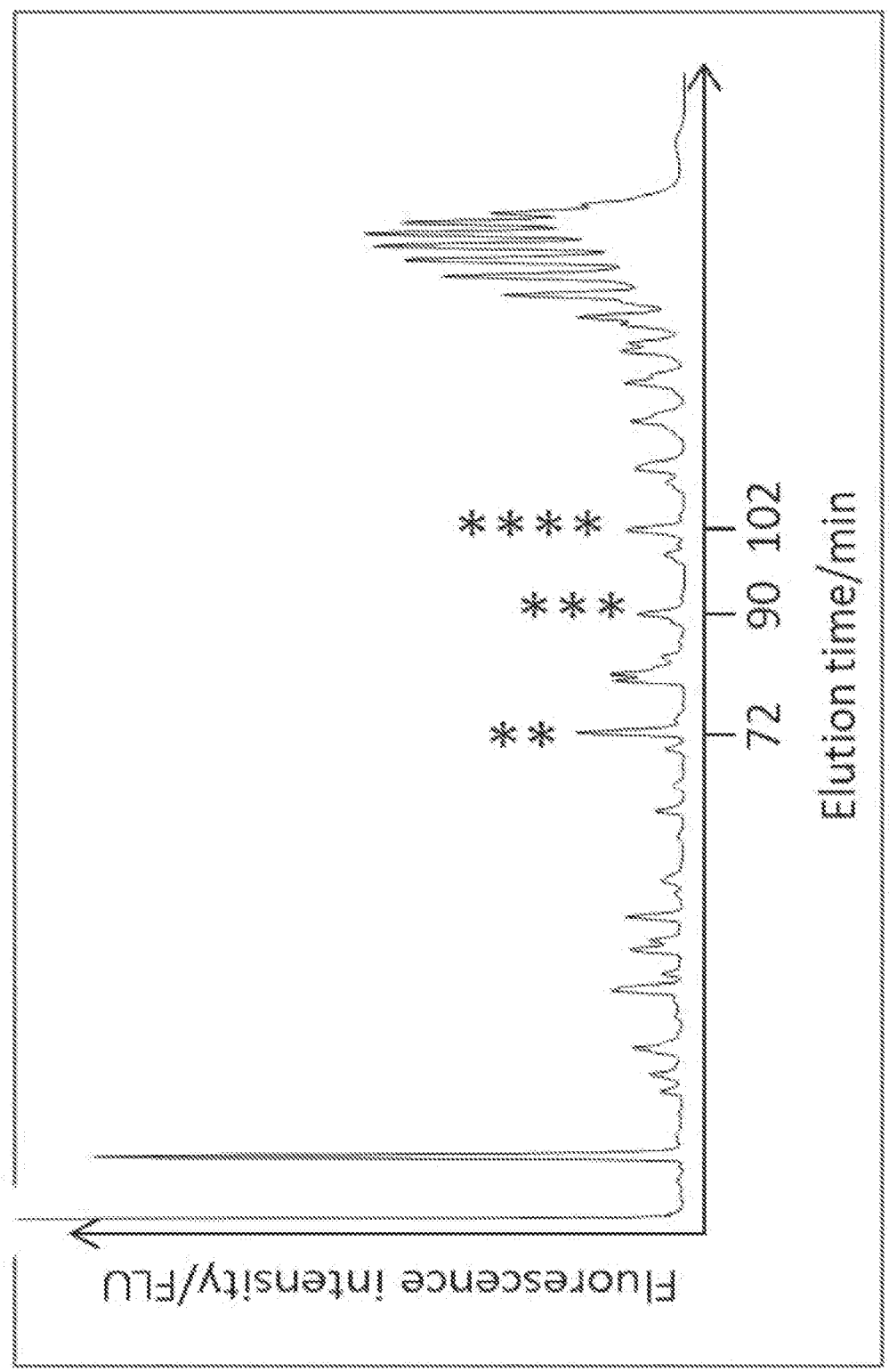
Figure 18B:
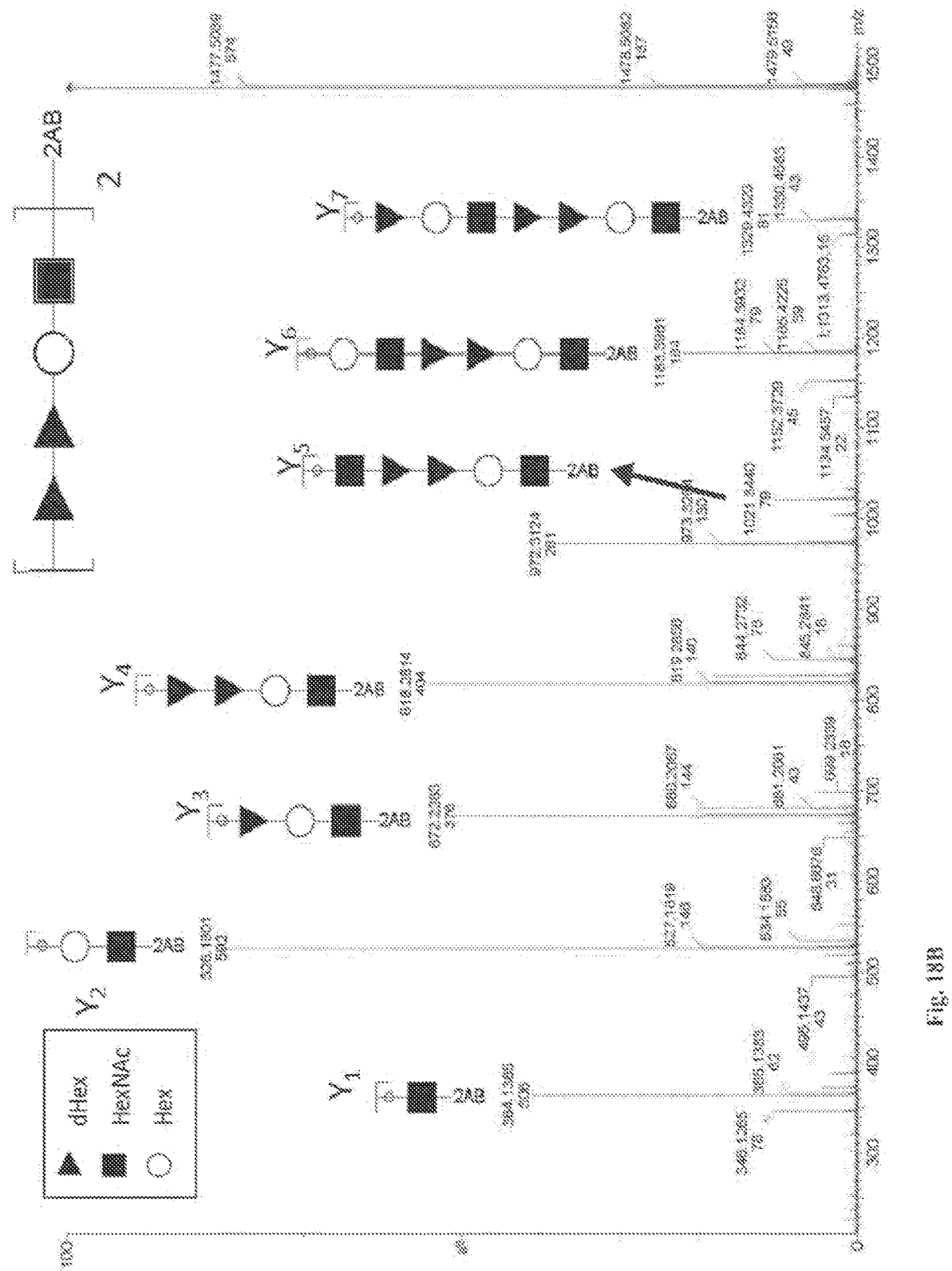
Figure 19:
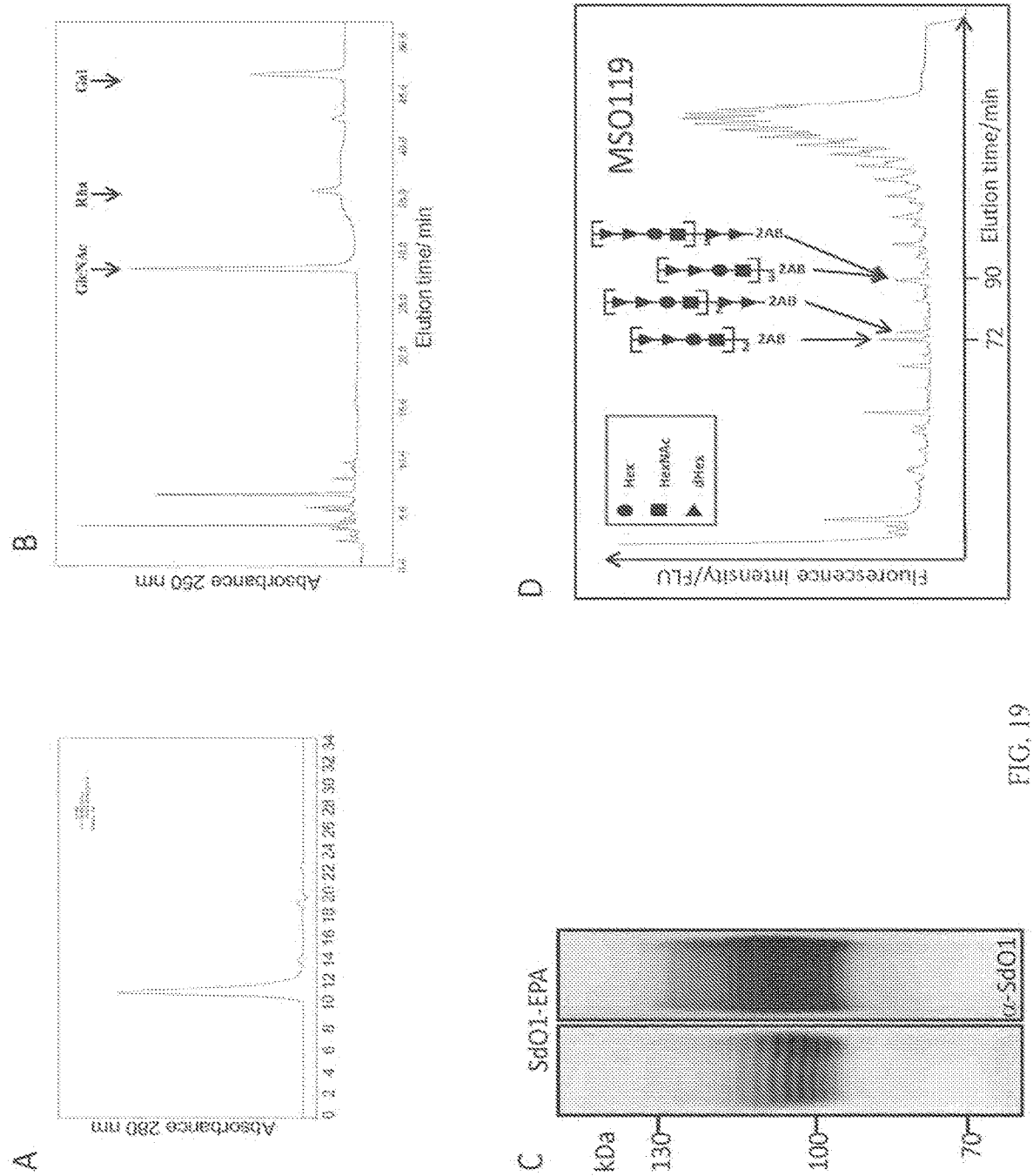

6.5 Example 5: Inserted Strain for S. dysenteriae O Antigen Glycoconjugate Production Although The rfp and rfb clusters of S. dysenteriae form a functional unit producing O antigen in E. coli, in the S. dysenteriae genome they are present in different locations ([8]). Both clusters were cloned in a pDOC plasmid consisting of the HR regions and a selection cassette as detailed in table 1. A BamHI fragment from plasmid pSDM7 containing rfb/rfp ([8]) was subcloned into pLAFR1 containing a suitable MCS cassette. From there, oligonucleotides 1261 and 1272 (see Table 3) were used to clone rfp/rfb in one amplicon into pDOC-derived p503, resulting in p504. p503 was cloned from p482 (see section 6.1): a PCR amplicon encoding the HR1 region for insertion, containing part of galF (galF') and the intergene region between galF and rmlB of strain W3110 (using oligonucleotides 1171/1263) was digested with SpeI and BamHI and ligated into p482 digested with the same enzymes (resulting in p503). rfp and rfb are found as two separated clusters on the genome of S. dysenteriae type I and were cloned that translation direction was the same for galF', rfp, rfb, and gnd when expressed from p504. Insertion of the DNA insert was performed in waaL positive and negative strains and tested by PCR for absence of O16 wzy, by 5' and 3' transition region PCR, silver stain of LPS samples, and Western blot analysis using typing sera (not shown). FIG. 17 shows the glycolipids analysis of inserted W3110 ΔrfbO16::rfbSd1 ΔwaaL and W3110 ΔrfbO16::rfbSd1 before and after the clmR cassette removal. When extracts were analyzed by silver staining after SDS PAGE, only the waaL positive strains showed the typical O antigen pattern of LPS, not the ΔwaaL strains. All strains responded to the anti *S. dysenteriae* 1 O antigen specific antiserum confirming the production of recombinant O antigen in these strains (FIG. 17).

To analyze the structure of the recombinant O antigen in molecular detail, the Und-PP bound polysaccharide pool from W3110 ΔrfbO16::rfbSd1-clmR ΔwaaL was analyzed by 2 AB labeling of hydrolyzed organic extracts of cells and normal phase HPLC (FIG. 18). The trace shows the ladder like pattern often observed in SDS PAGE. MS/MS analysis of certain peaks can be used to confirm the *S. dysenteriae* type 1 polysaccharide sequence.

W3110 ΔrfbO16::rfbSd1-clmR ΔwaaL was the host for production of EPA *S. dysenteriae* 1 conjugate as described below. To confirm the production of glycoconjugate vaccine candidates using this strain, the expression plasmids p293 and p114 were transformed into the strain and fermented at 10 l scale in a bioreactor. EPA conjugate was purified and unglycosylated EPA removed by classical chromatography. The resulting final bulk was analyzed to confirm sugar structure and conjugate quality by SEC HPLC (FIG. 19 A), SDS PAGE followed by coomassie staining or immunodetection (FIG. 19 C) monosaccharide composition analysis (FIG. 19 B) and hydrazinolysis followed by 2 AB labeling, HPLC analysis and MS/MS (FIG. 19 D).

6.6 Example 6: Inserted Strain for *S. flexneri* 2a O Antigen Glycoconjugate Production

*Shigella* O antigens are immunologically diverse. For a comprehensive vaccine against shigellosis using the O antigen polysaccharide as an antigen, it is believed that O antigen structures of at least five serotypes must be included, to result in sufficient coverage. The goal is to include as many antigenic elements as possible from the most prevalent infective strains and contain the *S. dysenteriae* type 1, *S. sonnei*, and *S. flexneri* type 6, and *S. flexneri* 2a and 3a O antigens [56].

Serotypes 2a and 3a are based on the same O antigen backbone polysaccharide structure which is called serotype Y. There is great O serotype diversity in *S. flexneri*. It is due to modifications of the Y serotype repeat units by glucose and acetyl groups. Modifications of this kind are responsible for the constitution of the 2a or 3a serotypes structures (FIG. 20 A). Y backbone modifications are diverse and different combinations of modifications lead many serologically crossreactive polysaccharide structures. Serotypes 2a and 3a contain two different Glucose and one acetylation branching modifications often found in *Shigella* and thus are included in a vaccine to pretect against other crossreactive antigens.

The decoration enzymes generating the structural diversity are specific transferases that attach glucose and acetyl residues to the backbone of serotype Y. Whereas the backbone is entirely encoded in the rfb cluster, the enzymes responsible for the addition of glucose or acetyl groups are encoded outside of the rfb clusters. The same observation was made for some *E. coli* O antigens (e.g. O16). Since in many cases the backbone modifications are believed to be important for immunogenicity, they must be included in inserted production strains.

For the construction of an inserted *E. coli* strain producing the O antigen that requires a glycosyltransferase (or acetyltransferase) that is located outside of the rfb cluster, first a host strain was constructed that contained the additional transferase, and test its functionality by coexpressing the rfb cluster from a plasmid. In a further step, insertion of the O antigen cluster in place of the W3110 rfb cluster is performed. The order of these events is purely practical and not systematical, i.e., the order could be inversed. This procedure was executed for making *S. flexneri* 2a O antigen, and it was shown that the glycoconjugate made with this strain is functionally active in preclinical tests.

We chose *E. coli* W3110 as the host strain for 2a and 3a glycoconjugate production because it has a proven capacity for efficient glycoconjugate production. W3110 is deficient in O antigen production due to a disrupted glycosyltransferase gene in the O16 rfb cluster. However, to avoid potential interferences by the remaining activities from the rfb cluster with our planned assays, the rfb glycosyl and acetyltransferase genes wbbIJK were deleted [13]. The selection cassette was automatically removed by using the site specific recombination functioning with the dif sites used by an *E. coli* recombinase [14]. When the *S. flexneri* rfb cluster cloned from strain *Shigella flexneri* 2457T (serotype 2a) was expressed, glycolipid analysis of extracts showed the *S. flexneri* serotype Y phenotype. LPS from these extracts was not reactive to the side chain modification specific anti group II and anti group 7, 8 antisera (FIG. 20 C, lane 1).

For addition of the glucose decorations to the Y serotype, advantage was taken of the existing modification system present in *E. coli* W3110. Glucose modifications are often catalyzed by an enzymatic machinery originating from a prophage DNA insert [57]. *E. coli* W3110 contains this genetic element called the gtr operon. The gtr operon contains three genes. The first two genes are highly conserved and common to most of the gtr clusters identified to date (gtrAB). The third gene encodes the glucosyltransferase which adds glucose to a specific location in the growing O antigen chain on the periplasmic side of the membrane. In the case of W3110, this gene is named gtrS. In *S. flexneri* 2a and 3a, gtr clusters are present. The respective gtrAB genes are highly homologous, whereas the third genes (gtrII in 2a and gtrX in 3a) are different [32]. Due to their mechanistic homology to the W3110 system, it was reasoned that exchange of gtrS with gtrII or gtrX would also transfer the glucose decoration activity.

To test this hypothesis, the gtrS gene was exchanged by gtrII or gtrX by homologous recombination [13], using a cassette excision strategy as described [14]. A clmR cassette flanked by dif sites was placed downstream to chemically synthetized gtrII or gtrX ORFs in plasmid p411. Oligonucleotides 1018 and 1019 were used to generate a PCR fragment encoding gtrII and clmR from p411. Oligonucleotide overhangs were identical to the sequences up (gtrB sequences)

and downstream of the gtrS ORF. Using this amplicon, homologous recombination was performed [13]. Correct recombination was checked by colony PCR (using oligonucleotides 1016/1017), and the PCR products were sequenced (FIG. 20 B). To check if the gtr enzymes can decorate the type Y backbone structure, positive strains were transformed with the plasmid expressing the rfb cluster from strain 2457T. Extracts from these cells contained LPS as analyzed by silver staining, but their electrophoretic mobility appeared slightly different as the control strain expressing the rfb cluster alone (FIG. 20 C, left panel, compare lanes 1, 2, 3). The same extracts were probed like before with the glucose side chain specific antisera and as expected, the anti group II antiserum raised a signal with the strain W3110 ΔgtrS::gtrII, and the W3110 ΔgtrS::gtrX strain raised a signal with the anti group 7,8 antiserum. Thus, exchange of the gtr genes transferred the specific capability for glucose decoration to *E. coli* W3110, resulting in strains W3110 ΔgtrS::gtrII and W3110 ΔgtrS::gtrX. Similarly, one could insert the entire gtr cluster or also the third gene only (i.e. the specific glucosyltransferase) into a suitable host strain to generate the decoration activity in a recombinant glycoconjugate expression strain.

For completion of the *S. flexneri* 3a structure with acetylation modifications, the known acetyltransferase genes can be inserted into the production strain using a similar strategy. For the 2a serotype, genome sequencing and homology analysis can be used to identify candidate acetyltransferase genes that can be tested for polysaccharide decoration activity.

To accommodate protein glycosylation with the recombinant 2a O antigen, the waaL gene was deleted by homologous recombination [13, 14] resulting in strain W3110 ΔgtrS::gtrII ΔwaaL. Furthermore, the *E. coli* W3110 rfb cluster was exchanged by the one from *S. flexneri* 2457T as described in example 1, resulting in W3110 ΔrfbO16::rfb2457T ΔgtrS::gtrII ΔwaaL. The donor plasmid p487 was constructed from p482 by insertion of a PCR amplicon prepared using oligonucleotides 1171 and 1172. In addition, to avoid metabolic degradation of arabinose used for induction of the carrier protein, the araBAD cluster was disrupted in this strain. It is well known that the araBAD deletion increases yields when recombinant proteins are controlled by the araBAD promoter system. Therefore, strain W3110 ΔrfbO16::rfb2457T ΔgtrS::gtrII ΔwaaL was transduced with phage lysate prepared from strain W3110 ΔaraBAD::cat. W3110 ΔaraBAD::clmR was prepared by homologous recombination using a DNA insert made by PCR using oligonucleotides 1562 and 1563 and pKD3 as a template [13].

To use the resulting strain W3110 ΔaraBAD::clmR ΔrfbO16::rfb2457T ΔgtrS::gtrII ΔwaaL for industrial scale vaccine candidate production, the expression plasmids for the EPA carrier protein containing 2 glycosylation sites (p293) and for the pglB oligosaccharyl transferase containing a HA tag (p114) were introduced into W3110 ΔaraBAD::clmR ΔrfbO16::rfb2457T ΔgtrS::gtrII ΔwaaL by electroporation. The resulting strain was fermented at 10 l scale and the EPA glycoconjugate purified from the resulting biomass. Purification was performed to remove host cell impurities and unglycosylated carrier protein. Conjugates were characterized by SEC HPLC (FIG. 21 B), SDS PAGE followed by coomassie staining and immunodetection (FIG. 21 A), hydrazinolysis followed by MS/MS (FIG. 21 D), monosaccharide composition analysis (FIG. 21 C), and GC-MS for absolute monosaccharide configuration (not shown) (see 5.2.1.7, and 5.3.5.). This data confirmed that insertion and chromosomal modification of the strain resulted in an efficient production system for the generation of a *S. flexneri* 2a vaccine product candidate.

To show that the vaccine candidate was functional in animal models, the immunogenicity of a 2a-$EPA_{E.\ coli}$ glycoconjugate vaccine produced in the inserted strain W3110 ΔaraBAD::clmR ΔrfbO16::rfb2457T ΔgtrS::gtrII ΔwaaL containing p114 and p293 was tested. Rats were administrated three times with three weeks interval subcutaneously with 2a-EPA conjugate containing 2.5 μg of carbohydrate in PBS or PBS alone (FIG. 22). The results show significant seroconversion in most individuals, and that the mean log titer was statistically significant higher in immunized animals (di-BC and Flex-BC groups) as compared to the animals that received control injections (PBS). This result also shows that for immunogenicity and thereby probably efficacy, the acetylation of the O antigen is not required. Acetylated 2a-EPA glycoconjugate (Flex-BC) was produced in an attenuated *S. flexneri* 2a strain (strain 2457T) by using the same procedure, but the production strain *S. flexneri* 2a ΔwaaL with introduced p114 and p293. Strain 2457T is known to acetylate its O antigen [58].

6.7 Example 7: Inserted Strain for *P. aeruginosa O*11 O Antigen Production

The O11 O antigen cluster was cloned into pDOC plasmid consisting of the HR regions and a selection cassette as detailed in table 1. The O antigen cluster was amplified from *P. aeruginosa* strain PA103 with oligonucleotides 2245/2247 (see Table 3). Strain construction was performed as described in example 1. Insertion of the DNA insert (with wzz) into W3110 ΔwaaL was tested by PCR for absence of O16 wzx and presence of 011, by 5' and 3' transition region PCR, silver stain of LPS samples, and western blot analysis using *P. aeruginosa* anti group E (011) typing sera. In the shown example, 4 clones with correct antibiotics resistance phenotypes were tested for O11 O antigen production (A to D, lanes 1-4) and they made the typical ladder like O antigen signal with electrophoretic mobility corresponding to around 34 kDa in size when analyzed with anti group E serum (FIG. 23). As controls *E. coli* DH5α cells containing the donor plasmid with wzz and without wzz were used (lanes 5 and 6). The control strain contains an active waaL gene and thus makes O11 LPS, which shows a different pattern than the O11 Und-PP (lanes 1-4). Accordingly, the signals are more intense and observed in a higher molecular weight range. In absence of wzz (lane 6), the signal concentrate to smaller molecular weights, indicating that the *E. coli O*16 wzz can take over this function efficiently. Taken together, these results showed successful insertion and functional expression of the *P. aeruginosa O*11 O antigen cluster in *E. coli*. Additional data indicate that *P. aeruginosa O*11 wzz is active for chain regulation in *E. coli* DH5a, and that its activity can be functionally replaced by *E. coli* chain length regulators enzymes of the wzz class.

6.8. Example 8: Insertion of a Chimeric, Non-Natural Cluster

Gram positive capsular polysaccharides production and glycosylation of carrier proteins using this polysaccharide in *E. coli* was achieved [10]. Polysaccharide was synthesized by introduced DNA composed of fusion constructs consisting of O antigen cluster fragments and CPS cluster fragments to make a recombinant O antigen with a CPS structure.

Such constructed chimeric clusters were inserted at two different positions into the W3110 genome to test productivity of Und-PP-CP5. To direct the insertion, different homology regions were cloned into the donor plasmids.

In one case, the target site was the W3110 rfb cluster like in the above examples, i.e. the HR regions were the up and downstream regions from the ORFs contained in the O16 rfb cluster. To insert the HR sites into pDOC-C, pDOC-C was cleaved with HindIII and XhoI and an assembly PCR product cut with the same enzymes was ligated into it. The assembly was done with oligonucleotides 1182 and 1184 on two PCR products which were generated using i) oligonucleotides 1181 and 1182, or ii) 1183 and 1184, and in both cases genomic DNA of W3110 ΔwaaL as template DNA. The resulting plasmid was p473. Oligonucleotides 1142 and 771 (or 1281) were used to amplify the chimeric CP5 producing gene cluster from a plasmid (p393, US2011/0274720 A1) for cloning into p473 by using Eco81I, resulting in p477 (or p498). p498 was cloned in a way that wzz and wzx of the O11 cluster were deleted in this plasmid (as compared to p477, where wzz and wzx are present).

In the other case, insertion was performed at target sites flanking the ECA genes wecA and wzzE. Since wecA may compete with the recombinant polysaccharide for the available Und-P in the cells, the deletion of wecA was reasoned to result in higher CP5 polysaccharide yields. To make a donor plasmid allowing the replacement of wecA and wzzE, pDOC-C was first modified with the two HR regions and then the CP5 chimeric cluster inserted. Oligonucleotides 1126 and 1129, as well as 1127 and 1128 were used to amplify HR regions 1 and 2 using W3110 chromosomal DNA as template. The PCR products were assembled using oligonucleotides 1126 and 1127, and the assembled HRs were cloned into the XhoI and HindIII sites of pDOC-C, resulting in p467. Oligonucleotides 1142 and 771 were used to amplify the chimeric CP5 producing gene cluster from a plasmid (p393, US2011/0274720 A1), and the corresponding PCR product was cloned into the Eco81I site of p467 resulting in p471.

Figure 24:
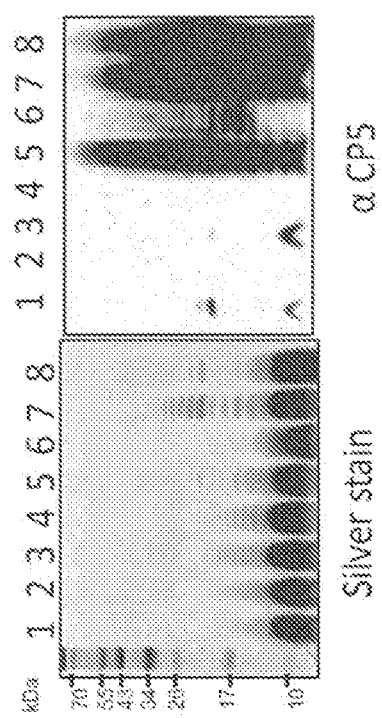

Insertion into both locations using p471, p498, and p477 was performed in detail as described in Example 1. The donor and helper plasmids were electroporated into W3110 cells, and cells were treated as described above. Colony PCR methods were used to confirm the correct insertion location. To show that the insertion resulted in strains able to produce a recombinant O antigen, proteinase K treated cell lysates from inserted clones and control cells were separated by SDS PAGE, and either stained by silver or transferred to nitrocellulose membranes and probed with anti CP5 specific aniserum. As controls, extracts from DH5α cells containing corresponding donor plasmids or W3110 ΔwecA containing the p393 cosmid expressing the CP5 modified O antigen (US2011/0274720 A1) were analyzed. Different ladder like signal intensities were obtained (FIG. 24), strongest with the donor plasmid p471 (lane 7), similarly strong with p498 (lane 5), weakly with p477 (lane 6). Lane 4 contains negative control cells with p473, which does not contain the chimeric CP5 cluster, only the HR1 and 2 regions and there are no CP5 signals. Ladder like signals at low molecular weight are most probably due to ECA polysaccharide and not CP5 as they are not detected with the anti CP5 specific antiserum. p498 and p477 differ in a small DNA stretch encoding the P. aeruginosa O11 wzz and wzx genes, which is present in p477. Thus it was concluded that wzz-wzx limits glycolipid production due to a promoter effect. p471, which contains the chimeric cluster including wzz-wzx, is transcribed most likely form the ECA promoter present in HR1. Thus, the location in p471 supports CP5 biosynthesis. The inserted clones were prepared using p471 (lane 1), p477 (lane 2), and p498 (lane 3) as donor plasmids. Albeit signals were in general much weaker, specific detection of the central ladder band and a low molecular weight band were detected. Intensities were strongest for the clone derived from the strongest donor plasmid (FIG. 24). Thus, this data confirm that the presented insertion methods can insert DNA pieces at least up to 16 kb long into different, selectable locations.

6.9. Example 9: A Bacterial Strain with an Inserted Oligosaccharyl Transferase Produces Bioconjugates This example demonstrates that bioconjugates can successfully be produced by a bacterial host strain that has been genetically modified by insertion of a nucleic acid encoding an oligosaccharyl transferase into the bacterial host cell genome.

The C. jejuni pglB gene, with an HA tag, was stably inserted into the genome of E. coli strain MG1655 (K12) using Staby™ Codon T7 technology (Delphi Genetics, Charleroi, Belgium). As part of the method of generating the E. coli strain with inserted pglB, pglB was isolated from the p114 plasmid, fused to the galK gene, and inserted into the host cell genome in place of the waaL gene. The resulting E. coli strain, MG1655 waaL::pglB-galK, was confirmed to contain stably integrated pglB of correct sequence.

Figure 25:
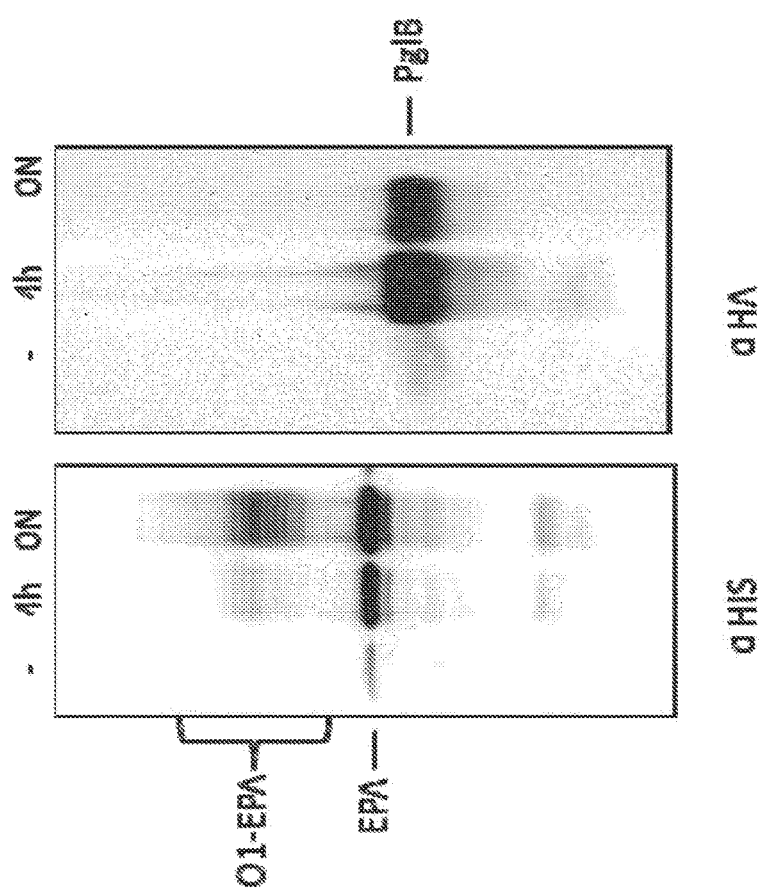
FIG. 25 depicts a Western blot analysis of production of pglB and O1-EPA by the MG1655 waaL::pglB-galK *E. coli* host strain harboring a plasmid that expresses an O1 antigen and a plasmid that expresses EPA. The left panel shows results of probing for EPA with an anti-HIS antibody; the right panel shows results of probing for pglB with an anti-HA antibody.

To assess the ability of MG1655 waaL::pglB-galK to produce bioconjugates, two plasmids were introduced into the strain. The first plasmid, p64, comprises nucleic acids encoding the Shigella dysenteriae O1 gene cluster. The second plasmid, p271, comprises nucleic acids encoding an EPA carrier protein with a histidine tag. The host cells were cultured for 4 hours or overnight, isolated, and subjected to Western blot analysis with an anti-HA antibody to identify pglB production and an anti-his antibody to identify EPA production. The Western blots confirmed that the MG1655 waaL::pglB-galK host strain expressing plasmids p64 and p271 successfully produced both the EPA and pglB proteins. See FIG. 25. Importantly, O1-EPA bioconjugates were identified, indicating the ability of the inserted pglB gene to produce a functional oligosaccharyl transferase in the host cells and thus demonstrating that the pglB gene can be inserted into bacterial host cells and retain its function. See FIG. 25.

Figure 26:
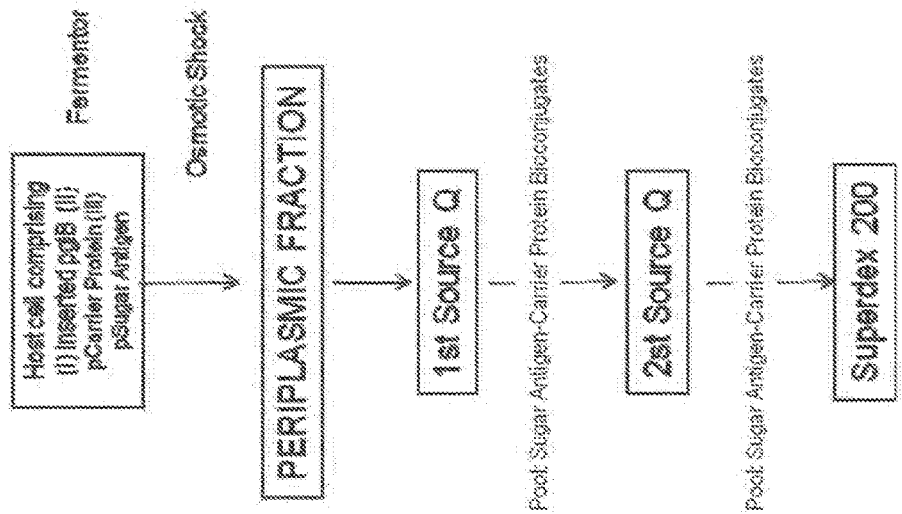
FIG. 26 depicts a strategy for purification of carrier protein-sugar antigen bioconjugates.

In another experiment to assess the ability of MG1655 waaL::pglB-galK to produce bioconjugates, different plasmids were introduced into the strain. The first plasmid, p281, comprises nucleic acids encoding the Shigella dysenteriae O1 gene cluster. The second plasmid, p293, comprises nucleic acids encoding an EPA carrier protein. The host cells were cultured for up to 16 hours in a bioreactor. At various time points, production of pglB and EPA were assessed by Western blot analysis using anti-EPA and anti-HA antibodies. As shown in FIG. 26, the Western blots confirmed that the MG1655 waaL::pglB-galK host strain expressing plasmids p281 and p293 successfully produced both the EPA and pglB proteins. Importantly, as observed with the MG1655 waaL::pglB-galK host strain expressing plasmids p64 and p271, the MG1655 waaL::pglB-galK host strain expressing plasmids p281 and p293 produced O1-EPA bioconjugates, indicating the ability of the inserted pglB gene to produce a functional oligosaccharyl transferase in the host cells and thus confirming that the pglB gene can be inserted into bacterial host cells and retain its function.

Next, O1-EPA bioconjugates produced by the MG1655 waaL::pglB-galK host strain expressing plasmids p281 and p293 were successfully isolated using a bioconjugate purification strategy. See FIG. 26. Briefly, proteins isolated from the periplasmic fraction of the MG1655 waaL::pglB-galK host strain expressing plasmids p281 and p293 grown overnight were ran over a first Q-Sepharose column. A chromatogram depicting the results is shown in FIG. 27; strong production of O1-EPA was observed (see fractions A6-A9 and the inset image). Fractions were ran on SDS-PAGE gels followed by Coomasie staining to identify O1-EPA containing fractions. See FIG. 28. Fractions A6-A9, identified as being abundant in O1-EPA, were pooled and ran over a second Q-Sepharose column and fractions obtained from the second column were ran on SDS-PAGE gels followed by Coomasie staining to identify O1-EPA containg fractions. See FIG. 29. A chromatogram depicting the results is shown in FIG. 30; strong production of O1-EPA was observed in fractions B4-B6. Finally, fractions B4-B6, identified as being abundant in O1-EPA, were pooled and ran over a Superdex 200 column, followed by Coomasie staining to identify fractions comprising purified O1-EPA bioconjugates. The final pool of isolated O1-EPA bioconjugates, shown by Coomasie staining in FIG. 31, were found to be highly purified (see FIG. 32) and proved to be of identical quality to O1-EPA bioconjugates prepared using a three-plasmid system, wherein the pglB gene was introduced into an *E. coli* host cell by way of a plasmid, rather than by insertion into the host cell genome.

6.10. Example 10: A Bacterial Strain Containing One Plasmid for Bioconjugate Production This example demonstrates that bioconjugates can successfully be produced by a bacterial host strain that has been genetically modified by exchange of a nucleic acid region encoding an rfb gene cluster and by insertion of a nucleic acid encoding an oligosaccharyltransferase into the bacterial host cell genome. Only a single plasmid, encoding a carrier protein, was required for bioconjugate production.

An HA tagged *C. jejuni* pglB gene, under the transcriptional control of the *E. coli* O121 rfb cluster promoter, was stably inserted into the genome of *E. coli* strain W3110 ΔrfbO16::rfb2457T ΔgtrS::gtrII ΔwaaL (described in example 6) by homologous recombination (Ref. 13), using a cassette excision strategy as described (Ref. 14). Whole-cell extracts ofpglB-positive strains were analyzed by SDS-PAGE and HA-tagged PglB was detected by Western blot using an anti-HA antibody. Expression of PglB was verified in *E. coli* strain W3110 ΔrfbO16::rfb2457T, ΔgtrS::gtrII, ΔwaaL, ::$p_{O121}$pglB (FIG. 33A, lane 1). PglB expressed by *E. coli* strain W3110 ΔrfbO16::rfb2457T, ΔgtrS::gtrJI, ΔwaaL, ::po21pglB was compared with PglB expressed by *E. coli* strain W3110 ΔrfbO16::rfb2457T ΔgtrS::gtrII ΔwaaL, which contains plasmid-borne pglB under the transcriptional control of a pTac promoter (FIG. 33A, compare lanes 1 and 2).

To assess the ability of W3110 ΔrfbO16::rfb2457T, ΔgtrS::gtrII, ΔwaaL, ::$p_{O121}$pglB to produce bioconjugates, an expression plasmid containing the EPA carrier protein engineered to comprise two N-glycosylation sites and a histidine tag (p150) was introduced into the strain. The resulting strain was cultured overnight and 2a-EPA was purified from periplasmic extracts using $Ni^{2+}$-affinity chromatography. Purified EPA was analyzed by SDS-PAGE followed by Coomassie blue staining and 2a-EPA glycoconjugate was detected (FIG. 33B). It was confirmed that an *E. coli* host cell with an oligosaccharyl transferase and rfb cluster and heterologous rfb cluster inserted into its genome, and with a single plasmid expressing a carrier protein, could be used to successfully produce bioconjugates.

6.11. Example 11: A Bacterial Strain Containing One Plasmid for Bioconjugate Production This example demonstrates that bioconjugates can successfully be produced by a bacterial host strain that has been genetically modified by exchange of a nucleic acid region encoding the rfb gene cluster and by insertion of a nucleic acid encoding an oligosaccharyltransferase into the bacterial host cell genome. Only a single plasmid, encoding a carrier protein, was required for bioconjugate production.

Two different *E. coli* strains were used: (i) StGVXN8905 (genotype: ΔaraBAD ΔgtrS::gtrII ΔrfbO16::rfb2457T ΔwaaL::pglBcuo), which comprises both pglb and the *Shigella flexneri* 2a rfb cluster (rfb2457T) inserted into the host cell genome, and a plasmid encoding the EPA carrier protein (pGVXN1198); (ii) StGVXN5083 (genotype: ΔaraBAD ΔgtrS::gtrII ΔrfbO16::rfb2457T ΔwaaL) which comprises ΔgtrS::gtrII ΔrfbO16::rfb2457T ΔwaaL) which comprises plasmid-expressed pglb (pGVXN970), plasmid-expressed EPA carrier protein (pGVXN1198), and the *Shigella flexneri* 2a rfb cluster inserted into the host cell genome. For genomic integration of the *C. jejuni* oligosaccharyltransferase pglB and the rfb cluster, the homologous recombination described herein was used.

As shown in FIG. 34, both *E. coli* strains expressing the oligosaccharyltransferase, carrier protein, and Shigella-flexneri 2a rfb cluster produced bioconjugates (see the signals between molecular wheight markers 90-170 kDa, which correspond to *S. flexneri* 2a-EPA bioconjugate). Importantly, this observation includes strain StGVXN8905 comprising double integration of an oligosaccharyltransferase and an rfb cluster. Thus, this Example demonstrates not only that stable host cells can be generated following double insertion of genes/gene clusters into the host cell genome, but that function of the genes is maintained. Specifically, function of the inserted oligosaccharyltransferase and inserted rfb cluster was preserved, resulting in the production of bioconjugate.

In conclusion, it has been demonstrated in the foregoing examples that bioconjugates can successfully be produced using a bacterial host cell that has been engineered to stably express, as part of its genome, an oligosaccharyl transferase and other genetic elements responsible for production of the correct undecaprenyl-pyrophosphate (Und-PP) linked polysaccharide, which are essential components of bioconjugate production. Advantageously, fewer plasmids, e.g., only a single plasmid (see Examples 10 and 11), were required for bioconjugate production using this novel system than in currently known systems of generating bioconjugates in host cells by use of heterologous glycosylation machinery.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

TABLE 1

Insertion strains.

| DNA of interest[a, e]; first gene-last gene | DNA insert[a]/kb | Insertion location/ (Strain; replaced DNA in acceptor strain) | HR1[a] | HR2[a] | Selection cassette[a] |
|---|---|---|---|---|---|
| E. coli rfb cluster serotype O1 from clinical isolate (GU299791*); rmlB-wekO | 11.1 kb | E. coli W3110; rfb cluster | galF[b] | gnd[c] | clmR[d] |
| E. coli rfb cluster serotype O2 from CCUG25 (GU299792*); rmlB-wekR | 12.4 kb | E. coli W3110; rfb cluster | galF[b] | gnd[c] | kanR[d] |
| E. coli rfb cluster serotype O6 from strain CCUG11309 (AE014075.1*); wzx-manB | 12.3 kb | E. coli W3110; rfb cluster | galF[b] | gnd[c] | kanR[d] |
| Shigella dysenteriae type I rfb cluster ([f]) | 10.1 kb | E. coli W3110; rfb cluster | galF[b] | gnd[c] | clmR[d] |
| S. flexneri type 2a rfb cluster (from galF to gnd) | 11.8 kb | E. coli W3110; rfb cluster | galF[b] | gnd[c] | clmR[d] |
| S. sonnei rfb cluster, without/with wzz[g]; wbgT to wbgZ | 12.1 kb/13.2 kb | E. coli W3110; rfb cluster | galF[b] | gnd[c] | clmR[d] |
| Chimeric PS synthesis cluster consisting of P. aeruginosa PAO103 O11 O antigen cluster (AF147795.1, wbjB-wbpM) and part of the S. aureus CP5 cluster (cap5H-cap5K)[h] | 16.3 kb | E. coli W3110; rfb cluster[j] E. coli W3110; wecA to wzzE | galF[b] 0.4 kb upstream of wecA | gnd[c] 0.4 kb downstream of wzzE | clmR[d] clmR[d] |
| P. aeruginosa PAO103 rfb cluster without and with wzz (AF147795.1); wzz to wbpM and wbjA to wbpM | 14.2 kb/13.1 kb | E. coli W3110; rfb cluster (galF to gnd) | galF[b] | gnd[c] | clmR[d] |

[a] see FIG. 1.

[b] HR1, 1 kb DNA upstream of rmlB of the W3110 rfb cluster encoding the intergene region between galF and rmlB, and a C-terminal fragment of the galF gene

[c] HR2, 1.6 kb downstream DNA of wbbL, the last gene in the O16 rfb cluster, cloned from E. coli strain W3110

[d] chloramphenicol resistance cassette (clmR) and kan resistance cassette (kanR) were cloned from pKD3 and pKD4 [13];

[e] when the sequence of the rfb cluster is public, an identifier is given. If the rfb cluster was cloned from a clinical isolate or from a strain without published sequence of the rfb cluster, a close published sequence is indicated and labeled with an asterisk*.

[f] The S. dysenteriae type I rfb cluster is composed of two operons, one reaching from rml-rfbQ (located between galF and gnd in the S. dysenteriae genome), and the second consisting of a bicistronic operon, rfpA and rfpB (between hisH and rfe (wecA))

[g] cloned from Plesiomonas shigelloides O17

[h] see [10]; this cluster is able to produce an O antigen which is identical in repeat unit structure as the CP5 capsular polysaccharide of Staphylococcus aureus.

[j] two versions of the chimeric cluster were inserted into the rfb locus, one containing and one lacking the wzz-wzx genes from P. aeruginosa PA103.

TABLE 2

Additional Insertion strains

| DNA insert | DNA Insert length/kb | Insertion location/Strain; replaced DNA in acceptor strain (HR1 to 2) | Functionality of inserted DNA shown by |
|---|---|---|---|
| *Streptococcus pneumoniae* CP14 cluster (wchA to wciY) | 8 kb | *E. coli* W3110; rfb cluster (galF to gnd) and colanic acid cluster (upstream of wcaM to downstream of wcaA) | *S. pneumoniae* CP14 PS production |
| *E. coli* rfb cluster serotype O4 from CCUG11450 | 14 kb | *E. coli* W3110; rfb cluster (galF to gnd) | *E. coli* O4 O polysaccharide production |
| *E. coli* rfb cluster serotype O25 from a clinical isolate upecGVXN436 | 16 kb | *E. coli* W3110; rfb cluster (galF to gnd) | *E. coli* O25 O polysaccharide production |
| *E. coli* rfb cluster serotype O75 from strain CCUG31 | 12.5 kb | *E. coli* W3110; rfb cluster (galF to gnd) | *E. coli* O75 O polysaccharide production |

TABLE 3

Oligonucleotide list

| Name | Use |
|---|---|
| 623 | ClmR cassette amplification from pKD3 for |
| 624 | waaL deletion |
| 1284 | Colony PCR; testing 5' region insertion of |
| 1513 | *P. shigelloides* O17 cluster insertion |
| 544 | Colony PCR; testing 3' region insertion of |
| 1237 | *P. shigelloides* O17 cluster insertion |
| 1226 | Colony PCR; wzy of *E. coli* O16 (W3110) |
| 1227 | |
| 1549 | Colony PCR; *P. shigelloides* O17 wzy-wbgV |
| 1550 | |
| 2245 | O antigen cluster amplification for cloning of O11 |
| 2247 | cluster into the donor plasmid (wzz to wbpM) |
| 1261 | *S. dysenteriae* type I rfp and rfp cluster cloning |
| 1272 | into donor plasmid |
| 2193 | Cloning of *E. coli* O1 galF-rfb gnd region into pLAFR1 |
| 2161 | |
| 2198 | Cloning of *E. coli* O1 rfb region to the donor plamid |
| 2166 | |
| 2207 | Cloning of *E. coli* O2 rfb region to the donor plamid |
| 2166 | |
| 1907 | Cloning of *E. coli* O6 rfb region to the donor plamid |
| 1908 | |
| 2104 | Colony PCR; testing 5' region insertion of *E. coli* O6 |
| 2045 | rfb cluster insertion |
| 2107 | Colony PCR; testing 3' region insertion of *E. coli* O6 |
| 1237 | rfb cluster insertion |
| 2224 | Colony PCR; *E. coli* O6 wzy amplification |
| 2225 | |
| 1126 | Cloning of HR1 into donor plasmid for insertion |
| 1129 | downstream of wecA |
| 1127 | Cloning of HR2 into donor plasmid for insertion |
| 1128 | in place of wzzE |
| 1142 | Cloning of CP5 chimeric cluster between HR1 |
| 771 | and 2 into donor plasmid |
| 1181 | Cloning of HR1 into donor plasmid for insertion |
| 1182 | at the position of the rfb cluster |
| 1183 | Cloning of HR2 into donor plasmid for insertion |
| 1184 | at the position of the rfb cluster |
| 2245 | Cloning/amplification of *P. aeruginosa* PA103 |
| 2247 | rfb cluster |
| 1171 | amplification of *S. Flexneri* rfb cluster including |
| 1172 | part of the galF gene upstream and the intergene region for donor plasmid cloning |
| 1018 | PCR amplification of DNA insert encoding gtrII |
| 1019 | and clmR for exchange of gtrS by gtrII |
| 1508 | PCR amplification of *P. Shigelloides* O17 rfb |
| 1509 | cluster for donor plasmid cloning, lacking wzz |
| 1509 | PCR amplification of *P. Shigelloides* O17 rfb |
| 1528 | cluster for donor plasmid cloning, including wzz |
| 2243 | typing PCR oligonucleotides for *E. coli* O2 |
| 2244 | |
| 2214 | PCR amplification and cloning of *E. coli* O1 rfb |
| 2215 | cluster into donor plasmid |
| 300 | complementary oligonucleotides with EcoRI |
| 301 | compatible overhangs for MCS insertion into EcoRI site of pLAFR1 |
| 1187 | Overlap PCR oligonucleotides for cloning the HR2 |
| 1188 | and the clmR cassette into the donor plamid pDOC-C |
| 1188 | PCR of clmR cassette from pKD3 |
| 1189 | |
| 1186 | PCR of HR2 for insertion into the W3110 rfb cluster, |
| 1187 | encoding a DNA stretch downstream of the last gene of the *E. coli* W3110 rfb cluster |

TABLE 4 list of Homing endonuclease

| Name | Source organism | Recognition site | SEQ ID NO. |
|---|---|---|---|
| AniI | *Aspergillus nidulans* | 5' TTGAGGAGGTTTCTCTGTAAATAA | 4 |
| | | 3' AACTCCTCCAAAGAGACATTTATT | 5 |
| CeuI | *Chlamydomonas eugametos* | 5' TAACTATAACGGTCCTAAGGTAGCGA | 6 |
| | | 3' ATTGATATTGCCAGGATTCCATCGCT | 7 |
| ChuI | *Chlamydomonas humicola* | 5' GAAGGTTTGGCACCTCGATGTCGGCTCATC | 8 |
| | | 3' CTTCCAAACCGTGGAGCTACAGCCGAGTAG | 9 |
| CpaI | *Chlamydomonas pallidostigmata* | 5' CGATCCTAAGGTAGCGAAATTCA | 10 |
| | | 3' GCTAGGATTCCATCGCTTTAAGT | 11 |
| CpaII | *Chlamydomonas pallidostigmata* | 5' CCCGGCTAACTCTGTGCCAG | 12 |
| | | 3' GGGCCGATTGAGACACGGTC | 13 |
| CreI | *Chlamydomonas reinhardtii* | 5' CTGGGTTCAAAACGTCGTGAGACAGTTTGG | 14 |
| | | 3' GACCCAAGTTTTGCAGCACTCTGTCAAACC | 15 |

TABLE 4-continued list of Homing endonuclease

| Name | Source organism | Recognition site | SEQ ID NO. |
|---|---|---|---|
| DmoI | *Desulfurococcus mobilis* | 5' ATGCCTTGCCGGGTAAGTTCCGGCGCGCAT<br>3' TACGGAACGGCCCATTCAAGGCCGCGCGTA | 16<br>17 |
| DreI | *Escherichia coli* pi-DreI | 5' CAAAACGTCGTAAGTTCCGGCGCG<br>3' GTTTTGCAGCATTCAAGGCCGCGC | 18<br>19 |
| HmuI | *Bacillus subtilis* phage SP01 | 5' AGTAATGAGCCTAACGCTCAGCAA<br>3' TCATTACTCGGATTGCGAGTCGTT | 20<br>21 |
| HmuII | *Bacillus subtilis* phage 5P82 | 5' AGTAATGAGCCTAACGCTCAACAA<br>3' TCATTACTCGGATTGCGAGTTGTT | 22<br>23 |
| LlaI | *Lactococcus lactis* | 5' CACATCCATAACCATATCATTTTT<br>3' GTGTAGGTATTGGTATAGTAAAAA | 24<br>25 |
| MsoI | *Monomastix* sp. | 5' CTGGGTTCAAAACGTCGTGAGACAGTTTGG<br>3' GACCCAAGTTTTGCAGCACTCTGTCAAACC | 26<br>27 |
| PI-PfuI | *Pyrococcus furiosus* Vc1 | 5' GAAGATGGGAGGAGGGACCGGACTCAACTT<br>3' CTTCTACCCTCCTCCCTGGCCTGAGTTGAA | 28<br>29 |
| PI-PkoII | *Pyrococcus kodakaraensis* KOD1 | 5' CAGTACTACGGTTAC<br>3' GTCATGATGCCAATG | 30<br>31 |
| PorI | *Pyrobaculum organotrophum* | 5' GCGAGCCCGTAAGGGTGTGTACGGG<br>3' CGCTCGGGCATTCCCACACATGCCC | 32<br>33 |
| PpoI | *Physarum polycephalum* | 5' TAACTATGACTCTCTTAAGGTAGCCAAAT<br>3' ATTGATACTGAGAGAATTCCATCGGTTTA | 34<br>35 |
| PI-PspI | *Pyrococcus* sp. | 5' TGGCAAACAGCTATTATGGGTATTATGGGT<br>3' ACCGTTTGTCGATAATACCCATAATACCCA | 36<br>37 |
| ScaI | *Saccharomyces capensis* | 5' TGTCACATTGAGGTGCACTAGTTATTAC<br>3' ACAGTGTAACTCCACGTGATCAATAATG | 38<br>39 |
| SceI | *Saccharomyces cerevisiae* | 5' AGTTACGCTAGGGATAACAGGGTAATATAG<br>3' TCAATGCGATCCCTATTGTCCCATTATATC | 40<br>41 |
| PI-SceI | *Saccharomyces cerevisiae* | 5' ATCTATGTCGGGTGCGGAGAAAGAGGTAATGAAATGGCA<br>3' TAGATACAGCCCACGCCTCTTTCTCCATTACTTTACCGT | 42<br>43 |
| SceII | *Saccharomyces cerevisiae* | 5' TTTTGATTCTTTGGTCACCCTGAAGTATA<br>3' AAAACTAAGAAACCAGTGGGACTTCATAT | 44<br>45 |
| SecIII | *Saccharomyces cerevisiae* | 5' ATTGGAGGTTTTGGTAACTATTTATTACC<br>3' TAACCTCCAAAACCATTGATAAATAATGG | 46<br>47 |
| SceIV | *Saccharomyces cerevisiae* | 5' TCTTTTCTCTTGATTAGCCCTAATCTACG<br>3' AGAAAAGAGAACTAATCGGGATTAGATGC | 48<br>49 |
| SceV | *Saccharomyces cerevisiae* | 5' AATAATTTTCTTCTTAGTAATGCC<br>3' TTATTAAAAGAAGAATCATTACGG | 50<br>51 |
| SceVI | *Saccharomyces cerevisiae* | 5' GTTATTTAATGTTTTAGTAGTTGG<br>3' CAATAAATTACAAAATCATCAACC | 52<br>53 |
| SceVII | *Saccharomyces cerevisiae* | 5' TGTCACATTGAGGTGCACTAGTTATTAC<br>3' ACAGTGTAACTCCACGTGATCAATAATG | 54<br>55 |
| Ssp6803I | *Synechocystis* sp. PCC 6803 | 5' GTCGGGCTCATAACCCGAA<br>3' CAGCCCGAGTATTGGGCTT | 56<br>57 |
| TevI | *Escherichia coli* phage T4 | 5' AGTGGTATCAACGCTCAGTAGATG<br>3' TCACCATAGTTGCGAGTCATCTAC | 58<br>59 |
| TevII | *Escherichia coli* phage T4 | 5' GCTTATGAGTATGAAGTGAACACGTTATTC<br>3' CGAATACTCATACTTCACTTGTGCAATAAG | 60<br>61 |
| TevIII | *Escherichia coli* phage RB3 | 5' TATGTATCTTTTGCGTGTACCTTTAACTTC<br>3' ATACATAGAAAACGCACATGGAAATTGAAG | 62<br>63 |
| PI-TliI | *Thermococcus litoralis* | 5' TAYGCNGAYACNGACGGYTTYT<br>3' ATRCGNCTRTGNCTGCCTAARA | 64<br>65 |

TABLE 4-continued list of Homing endonuclease

| Name | Source organism | Recognition site | SEQ ID NO. |
|---|---|---|---|
| PI-TliII | Thermococcus litoralis | 5' AAATTGCTTGCAAACAGCTATTACGGCTAT | 66 |
| | | 3' TTTAACGAACGTTTGTCGATAATGCCGATA | 67 |
| Tsp061I | Thermoproteus sp. IC-061 | 5' CTTCAGTATGCCCCGAAAC | 68 |
| | | 3' GAAGTCATACGGGGCTTTG | 69 |
| Vdi141I | Vukanisaeta distributa IC-141 | 5' CCTGACTCTCTTAAGGTAGCCAAA | 70 |
| | | 3' GGACTGAGAGAATTCCATCGGTTT | 71 |

TABLE 5 list of replication origins

| Ori name | Copies | Comment |
|---|---|---|
| IncW | | |
| R100 | | |
| pUC | 500-700 | From pUC19 (modified pMB1) |
| pMB1 | 15-20 | From plasmid pBR322 |
| BAC | 1 | |
| repA, rep101 | ~5 | From pSC101 |
| p15A | 10-12 | From pMR101 |
| pSC101TS | | Mutated repA, only propagates at 30° C. |
| F plasmid ori | 1-2 | |

TABLE 6 antibiotics used in molecular biology

| ABBREVIATION | ANTIBIOTIC |
|---|---|
| amp | ampicillin |
| clm | chloramphenicol |
| | erythromycin |
| gen | gentamycin |
| kan | kanamycin |
| neo | neomycin |
| | nalidixic acid |
| | rifampicin |
| spec | spectinomycin |
| | streptomycin |
| tet | tetracycline |
| tmp | trimethoprim |
| | zeocin |

TABLE 7

Inducible promoters used in bacterial expression

| Promoter | Source | Regulation | Induction | Level of Expression | Additional Information |
|---|---|---|---|---|---|
| lac | E. coli | lacI, lacI$^q$ | IPTG | low | |
| lacUV5 | E. coli | lacI, lacI$^q$ | IPTG | low | Theoretically not subject to cAMP dependent regulation |
| tac (hybrid) | E. coli | lacI, lacI$^q$ | IPTG | Allows accumulation of protein to about 15-30% of total cell protein | Consists of the −35 region of the trp promoter and the −10 region of the lac promoter (differs from the trc promoter by 1 bp) |
| trc (hybrid) | E. coli | lacI, lacI$^q$ | IPTG | Allows accumulation of protein to about 15-30% of total cell protein | Consists of the −35 region of the trp promoter and the −10 region of the lac promoter (differs from the tac promoter by 1 bp) |
| trp | E. coli | Addition of fructose to the growth medium increases down regulation under non-induced conditions. | Tryptophan starvation or addition of B-indoleacrylic acid | | |
| araBAD | E. coli | araC | l-arabinose | Weaker than the tac promoter | There is extensive heterogeneity in cell populations treated with subsaturating concentrations of l-arabinose (some bacteria are fully induced and others not at all). |

TABLE 7-continued

Inducible promoters used in bacterial expression

| Promoter | Source | Regulation | Induction | Level of Expression | Additional Information |
|---|---|---|---|---|---|
| phoA | E. coli | phoB (positive) phoR (negative) | phosphate starvation | | Tightly controlled. Induction requires phosphate starvation, and so can limit the duration of protein synthesis. |
| recA | E. coli | lexA | nalidixic acid | | |
| proU | E. coli | | osmolarity | | |
| cst-1 | E. coli | | glucose starvation | | |
| tetA | E. coli | | tetracyclin | | |
| cadA | E. coli | cadR | pH | | |
| nar | E. coli | fnr | anaerobic conditions | | |
| pL(T7) | T7 phage | cIts857 | thermal (shift to 42° C.) | moderately high | A phage-encoded cL repressor encodes a repressor, typically expressed from an inserted copy of a phage in the host genome. the repressor is temperature-sensitive and is functional at lower temperatures but denatures at temperatures higher then 37.5° C.. Therefor the induction of expression is by a simple temp. shift. |
| cspA | E. coli | | Thermal cold shock (shift to below 20° C.) | | The cspA core promoter is only weakly induced by temp. downshift. A 159 nucleotide long untranslated region at the 5' end of cspA driven transcripts makes them highly unstable at 37° C. and significantly increases their stability at low temps. This region also favors their engagement by a cold modified translational machinery. The cspA system becomes repressed 1-2 hours after temp. downshift. |
| SP6 | Salmonella phage | | | | |
| T7-lac operator | T7 phage | lacI$^q$ | IPTG | Allows accumulation of protein to about 40-50% of total cell protein | |
| T3-lac operator | T3 phage | lacI$^q$ | IPTG | | |
| T5-lac operator | T5 phage | lacI, lacI$^q$ | IPTG | | This promoter is recognized by the E. coli RNA polymerase |
| T4 gene 32 | T4 phage | | T4 infection | | |
| nprM-lac operator | Bacillus | lacI$^q$ | IPTG | | |
| VHb | Vitreoscilla | | oxygen | | |
| Protein A | S. aureus | | | | |

TABLE 8 bacterial expression strains

Escherichia coli
Salmonella sp.
Shigella
Yersinia
Xanthomonas
Pseudomonas sp
Lactobacillus
Lactococcus
Staphylococcus
Streptococcus
Streptomyces
Acinetobacter
Citrobacter

REFERENCES CITED

1. Sambrook J, Fritsch, E. F., Maniatis, T.: Molecular Cloning: A Laboratory Manual. Cold Spring Harbor, NY: Cold Spring Harbor Laboratory Press.; 1989.
2. Lin-Chao S, Bremer H: Effect of the bacterial growth rate on replication control of plasmid pBR322 in Escherichia coli. Mol Gen Genet 1986, 203(1):143-149.
3. Paulsson J, Ehrenberg M: Noise in a minimal regulatory network: plasmid copy number control. Q Rev Biophys 2001, 34(1):1-59.
4. COMMITTEE WE, BIOLOGICAL O, STANDARDIZATION: WHO Technical Report Series 941. In: Fifty-sixth Report. Edited by Organization WH. Geneva: World Health Organization; 2007.
5. Haldimann A, Wanner B L: Conditional-replication, integration, excision, and retrieval plasmid-host systems for gene structure-function studies of bacteria. JOURNAL OF BACTERIOLOGY 2001, 183(21):6384-6393.

6. Reeves P R, Hobbs M, Valvano M A, Skurnik M, Whitfield C, Coplin D, Kido N, Klena J, Maskell D, Raetz C R et al: Bacterial polysaccharide synthesis and gene nomenclature. *Trends in microbiology* 1996, 4(12):495-503.
7. Ho M M, Bolgiano B, Martino A, Kairo S K, Corbel M J: Preclinical laboratory evaluation of a bivalent *Staphylococcus aureus* saccharide-exotoxin A protein conjugate vaccine. *Hum Vaccin* 2006, 2(3):89-98.
8. Falt I C, Mills D, Schweda E K, Timmis K N, Lindberg A A: Construction of recombinant aroA salmonellae stably producing the *Shigella dysenteriae* serotype 1 O-antigen and structural characterization of the *Salmonella/Shigella* hybrid LPS. *Microb Pathog* 1996, 20(1):11-30.
9. Ihssen J, Kowarik M, Dilettoso S, Tanner C, Wacker M, Thony-Meyer L: Production of glycoprotein vaccines in *Escherichia coli*. *Microbial cellfactories* 2010, 9:61.
10. Wacker M, Kowarik M, Wetter M: Capsular gram positive bacteria bioconjugate vaccines. In. Edited by organization Wip; 2011.
11. Lee D J, Bingle L E, Heurlier K, Pallen M J, Penn C W, Busby S J, Hobman J L: Gene doctoring: a method for recombineering in laboratory and pathogenic *Escherichia coli* strains. *BMC microbiology* 2009, 9:252.
12. Kuhlman T E, Cox E C: Site-specific chromosomal integration of large synthetic constructs. *Nucleic acids research* 2010, 38(6):e92.
13. Datsenko K A, Wanner B L: One-step inactivation of chromosomal genes in *Escherichia coli* K-12 using PCR products. *Proc Natl Acad Sci USA* 2000, 97(12):6640-6645.
14. Bloor A E, Cranenburgh R M: An efficient method of selectable marker gene excision by Xer recombination for gene replacement in bacterial chromosomes. *Applied and environmental microbiology* 2006, 72(4):2520-2525.
15. Tsafnat G, Copty J, Partridge S R: RAC: Repository of Antibiotic resistance Cassettes. *Database* (Oxford) 2011, 2011:bar054.
16. Goh S, Good L: Plasmid selection in *Escherichia coli* using an endogenous essential gene marker. *BMC biotechnology* 2008, 8:61.
17. Zhang Y, Buchholz F, Muyrers J P, Stewart A F: A new logic for DNA engineering using recombination in *Escherichia coli*. *Nature genetics* 1998, 20(2):123-128.
18. Yu D, Ellis H M, Lee E C, Jenkins N A, Copeland N G, Court D L: An efficient recombination system for chromosome engineering in *Escherichia coli*. *Proceedings of the National Academy of Sciences of the United States ofAmerica* 2000, 97(11):5978-5983.
19. Rivero-Muller A, Lajic S, Huhtaniemi I: Assisted large fragment insertion by Red/ET-recombination (AL-FIRE)—an alternative and enhanced method for large fragment recombineering. *Nucleic acids research* 2007, 35(10):e78.
20. Muyrers J P, Zhang Y, Testa G, Stewart A F: Rapid modification of bacterial artificial chromosomes by ET-recombination. *Nucleic acids research* 1999, 27(6):1555-1557.
21. Guzman L M, Belin D, Carson M J, Beckwith J: Tight regulation, modulation, and high-level expression by vectors containing the arabinose PBAD promoter. *JOURNAL OF BACTERIOLOGY* 1995, 177(14):4121-4130.
22. Cardona S T, Mueller C L, Valvano M A: Identification of essential operons with a rhamnose-inducible promoter in *Burkholderia cenocepacia*. *Applied and environmental microbiology* 2006, 72(4):2547-2555.
23. Valdez-Cruz N A, Ramirez O T, Trujillo-Roldan M A: Molecular responses of *Escherichia coli* caused by heat stress and recombinant protein production during temperature induction. *Bioeng Bugs* 2011, 2(2):105-110.
24. Huang J Z, Schell M A: In vivo interactions of the NahR transcriptional activator with its target sequences. Inducer-mediated changes resulting in transcription activation. *J Biol Chem* 1991, 266(17):10830-10838.
25. Geissendorfer M, Hillen W: Regulated expression of heterologous genes in *Bacillus subtilis* using the Tn10 encoded tet regulatory elements. *Applied microbiology and biotechnology* 1990, 33(6):657-663.
26. del Solar G, Giraldo R, Ruiz-Echevarria M J, Espinosa M, Diaz-Orejas R: Replication and control of circular bacterial plasmids. *Microbiology and molecular biology reviews: MMBR* 1998, 62(2):434-464.
27. Hashimoto-Gotoh T, Sekiguchi M: Mutations of temperature sensitivity in R plasmid pSC101. *JOURNAL OF BACTERIOLOGY* 1977, 131(2):405-412.
28. Kues U, Stahl U: Replication of plasmids in gram-negative bacteria. *Microbiol Rev* 1989, 53(4):491-516.
29. Schweizer H P, Hoang T T: An improved system for gene replacement and xylE fusion analysis in *Pseudomonas aeruginosa*. *Gene* 1995, 158(1):15-22.
30. Kamoun S, Tola E, Kamdar H, Kado C I: Rapid generation of directed and unmarked deletions in *Xanthomonas*. *Mol Microbiol* 1992, 6(6):809-816.
31. Stagg R M, Tang S S, Carlin N I, Talukder K A, Cam P D, Verma N K: A novel glucosyltransferase involved in O-antigen modification of *Shigella flexneri* serotype 1c. *JOURNAL OF BACTERIOLOGY* 2009, 191(21):6612-6617.
32. Lehane A M, Korres H, Verma N K: Bacteriophage-encoded glucosyltransferase GtrII of *Shigella flexneri*: membrane topology and identification of critical residues. *The Biochemical journal* 2005, 389(Pt 1):137-143.
33. Clark C A, Beltrame J, Manning P A: The oac gene encoding a lipopolysaccharide O-antigen acetylase maps adjacent to the integrase-encoding gene on the genome of *Shigella flexneri* bacteriophage Sf6. *Gene* 1991, 107(1):43-52.
34. Turan S, Galla M, Ernst E, Qiao J, Voelkel C, Schiedlmeier B, Zehe C, Bode J: Recombinase-mediated cassette exchange (RMCE): traditional concepts and current challenges. *Journal of molecular biology* 2011, 407(2):193-221.
35. Cherepanov P P, Wackernagel W: Gene disruption in *Escherichia coli*: TcR and KmR cassettes with the option of Flp-catalyzed excision of the antibiotic-resistance determinant. *Gene* 1995, 158(1):9-14.
36. Sauer B: Functional expression of the cre-lox site-specific recombination system in the yeast *Saccharomyces cerevisiae*. *Molecular and cellular biology* 1987, 7(6):2087-2096.
37. Grimont P, Weill F: ANTIGENIC FORMULAE OF THE SALMONELLA SEROVARS. In., 9th edition edn. Geneva: WHO Collaborating Centre for Reference and Research on *Salmonella*; 2007.
38. Rocchetta H L, Burrows L L, Lam J S: Genetics of O-antigen biosynthesis in *Pseudomonas aeruginosa*. *Microbiology and molecular biology reviews: MMBR* 1999, 63(3):523-553.
39. Trautmann M, Held T K, Cross A S: O antigen seroepidemiology of *Klebsiella* clinical isolates and implications for immunoprophylaxis of *Klebsiella* infections. *Vaccine* 2004, 22(7):818-821.

40. Pantophlet R, Nemec A, Brade L, Brade H, Dijkshoorn L: O-antigen diversity among *Acinetobacter baumannii* strains from the Czech Republic and Northwestern Europe, as determined by lipopolysaccharide-specific monoclonal antibodies. *Journal of clinical microbiology* 2001, 39(7):2576-2580.
41. Hossain H, Wellensiek H J, Geyer R, Lochnit G: Structural analysis of glycolipids from *Borrelia burgdorferi*. *Biochimie* 2001, 83(7):683-692.
42. Borud B, Aas F E, Vik A, Winther-Larsen H C, Egge-Jacobsen W, Koomey M: Genetic, structural, and antigenic analyses of glycan diversity in the O-linked protein glycosylation systems of human *Neisseria* species. *JOURNAL OF BACTERIOLOGY* 2010, 192(11):2816-2829.
43. Borud B, Viburiene R, Hartley M D, Paulsen B S, Egge-Jacobsen W, Imperiali B, Koomey M: Genetic and molecular analyses reveal an evolutionary trajectory for glycan synthesis in a bacterial protein glycosylation system. *Proceedings of the National Academy of Sciences of the United States of America* 2011, 108(23):9643-9648.
44. McConville M J, Bacic A, Mitchell G F, Handman E: Lipophosphoglycan of *Leishmania major* that vaccinates against cutaneous leishmaniasis contains an alkylglycerophosphoinositol lipid anchor. *Proceedings of the National Academy of Sciences of the United States of America* 1987, 84(24):8941-8945.
45. McConville M J, Ferguson M A: The structure, biosynthesis and function of glycosylated phosphatidylinositols in the parasitic protozoa and higher eukaryotes. *The Biochemical journal* 1993, 294 (Pt 2):305-324.
46. Astronomo R D, Burton D R: Carbohydrate vaccines: developing sweet solutions to sticky situations? *Nature reviews Drug discovery* 2010, 9(4):308-324.
47. Lemuth K, Steuer K, Albermann C: Engineering of a plasmid-free *Escherichia coli* strain for improved in vivo biosynthesis of astaxanthin. *Microbial cell factories* 2011, 10:29.
48. Bigge J C, Patel T P, Bruce J A, Goulding P N, Charles S M, Parekh R B: Nonselective and efficient fluorescent labeling of glycans using 2-amino benzamide and anthranilic acid. *Anal Biochem* 1995, 230(2):229-238.
49. Royle L, Mattu T S, Hart E, Langridge J I, Merry A H, Murphy N, Harvey D J, Dwek R A, Rudd P M: An analytical and structural database provides a strategy for sequencing O-glycans from microgram quantities of glycoproteins. *Anal Biochem* 2002, 304(1):70-90.
50. Leyva A, Quintana A, Sanchez M, Rodriguez E N, Cremata J, Sanchez J C: Rapid and sensitive anthrone-sulfuric acid assay in microplate format to quantify carbohydrate in biopharmaceutical products: method development and validation. *Biologicals: journal of the International Association of Biological Standardization* 2008, 36(2):134-141.
51. Li D, Liu B, Chen M, Guo D, Guo X, Liu F, Feng L, Wang L: A multiplex PCR method to detect 14 *Escherichia coli* serogroups associated with urinary tract infections. *J Microbiol Methods*, 82(1):71-77.
52. Ikeda H, Tomizawa J I: Transducing fragments in generalized transduction by phage P1. L Molecular origin of the fragments. *Journal of molecular biology* 1965, 14(1):85-109.
53. Merry A H, Neville D C, Royle L, Matthews B, Harvey D J, Dwek R A, Rudd P M: Recovery of intact 2-aminobenzamide-labeled O-glycans released from glycoproteins by hydrazinolysis. *Anal Biochem* 2002, 304(1):91-99.
54. Baumann H, Jansson P E, Kenne L, Widmalm G: Structural studies of the *Escherichia coli* O1A O-polysaccharide, using the computer program CASPER. *Carbohydrate Research* 1991, 211(1):183-190.
55. Kowarik M, Young N M, Numao S, Schulz B L, Hug I, Callewaert N, Mills D C, Watson D C, Hernandez M, Kelly J F et al: Definition of the bacterial N-glycosylation site consensus sequence. *The EMBO journal* 2006, 25(9): 1957-1966.
56. Levine M M, Kotloff K L, Barry E M, Pasetti M F, Sztein M B: Clinical trials of *Shigella* vaccines: two steps forward and one step back on a long, hard road. *Nat Rev Microbiol* 2007, 5(7):540-553.
57. Mavris M, Manning P A, Morona R: Mechanism of bacteriophage SfII-mediated serotype conversion in *Shigella flexneri*. *Mol Microbiol* 1997, 26(5):939-950.
58. Perepelov A V, L'Vov V L, Liu B, Senchenkova S N, Shekht M E, Shashkov A S, Feng L, Aparin P G, Wang L, Knirel Y A: A similarity in the O-acetylation pattern of the O-antigens of *Shigella flexneri* types 1a, 1b, and 2a. *Carbohydr Res* 2009, 344(5):687-692.

EQUIVALENTS

The methods, host cells, and compositions disclosed herein are not to be limited in scope by the specific embodiments described herein. Indeed, various modifications of the methods, host cells, and compositions in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A method of producing an N-glycosylated protein, wherein the method comprises culturing an *Escherichia coli* (*E. coli*) host cell under conditions suitable for production of proteins, wherein the *E. coli* host cell genome comprises:
   (i) a heterologous DNA sequence that encodes an oligosaccharyl transferase;
   (ii) a heterologous DNA sequence of at least 12 kb that encodes a glycosyltransferase from *Candida albicans* wherein the glycosyltransferase from *Candida albicans* is capable of making a *Candida albicans* polysaccharide; and
   wherein the *E. coli* host cell further comprises a gene that encodes a carrier protein containing at least SEQ ID NO: 72 having the sequence D/E-X-N-Z-S/T, wherein X and Z are independently selected from any amino acid except proline.

2. The method of claim 1, wherein the carrier protein is detoxified Exoprotein A from *Pseudomonas aeruginosa* (EPA).

3. The method of claim 1, wherein the heterologous DNA sequence that encodes an oligosaccharyl transferase comprises a pglB gene.

4. The method of claim 3, wherein the pglB gene is from *C. jejuni*.

5. The method of claim 1, wherein the glycosyltransferase from *Candida albicans* is capable of making a polysaccharide from *Candida albicans*.

* * * * *